United States Patent
Vaka et al.

(10) Patent No.: US 10,588,863 B2
(45) Date of Patent: *Mar. 17, 2020

(54) EXTENDED RELEASE COMPOSITIONS COMPRISING PYRIDOSTIGMINE

(71) Applicant: KASHIV BIOSCIENCES, LLC, Bridgewater, NJ (US)

(72) Inventors: Siva Ram Kiran Vaka, Piscataway, NJ (US); Namdev B. Shelke, Somerville, NJ (US); Dipen Desai, Whippany, NJ (US); Wantanee Phuapradit, Montville, NJ (US); Navnit H. Shah, Clifton, NJ (US)

(73) Assignee: KASHIV BIOSCIENCES, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/556,092

(22) Filed: Aug. 29, 2019

(65) Prior Publication Data

US 2019/0388351 A1   Dec. 26, 2019

Related U.S. Application Data

(63) Continuation-in-part of application No. 16/445,110, filed on Jun. 18, 2019, which is a continuation-in-part (Continued)

(51) Int. Cl.
   *A61K 9/20* (2006.01)
   *A61K 31/4425* (2006.01)

(52) U.S. Cl.
   CPC .......... *A61K 9/2013* (2013.01); *A61K 9/2009* (2013.01); *A61K 9/2027* (2013.01); *A61K 9/2054* (2013.01); *A61K 31/4425* (2013.01)

(58) Field of Classification Search
   None
   See application file for complete search history.

(56) References Cited

U.S. PATENT DOCUMENTS

| 4,101,650 A | 7/1978 | Umezawa |
| 4,777,033 A | 10/1988 | Ikura et al. |

(Continued)

FOREIGN PATENT DOCUMENTS

| WO | WO 00/015198 A1 | 3/2000 |
| WO | WO 01/010419 A1 | 2/2001 |

(Continued)

OTHER PUBLICATIONS

Deshpande et al., "Development of a Novel Controlled-Release System for Gastric Retention," Pharmaceutical Research, 14(6):815-819 (1997).

(Continued)

*Primary Examiner* — Bong-Sook Baek
(74) *Attorney, Agent, or Firm* — Baker Botts L.L.P.

(57) ABSTRACT

Extended release pyridostigmine dosage forms, suitable for maintaining stable plasma concentrations with reduced or minimized initial burst release/dose dumping of pyridostigmine, are provided. The dosage forms include matrix tablets, gastroretentive tablets, and pellets, the latter being suitable for dosing in capsules, tablets, and sachets, as well as for sprinkling on foodstuffs. The disclosure also provides methods for improving patient compliance by administering once-a-day extended release pyridostigmine bromide dosage forms that provide a superior controlled drug release.

19 Claims, 26 Drawing Sheets

Figure 1A:
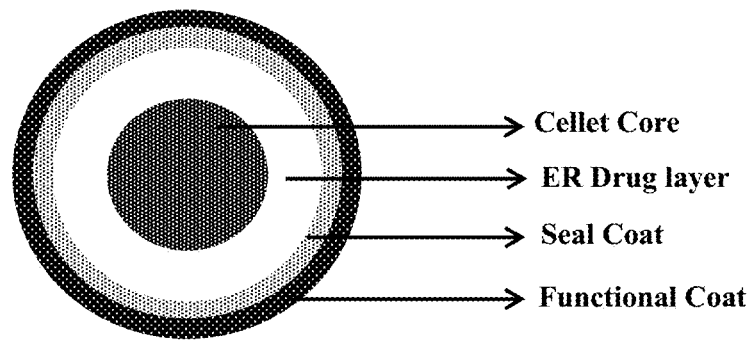

Related U.S. Application Data of application No. PCT/US2018/038118, filed on Jun. 18, 2018.

(60) Provisional application No. 62/725,024, filed on Aug. 30, 2018, provisional application No. 62/826,402, filed on Mar. 29, 2019, provisional application No. 62/520,796, filed on Jun. 16, 2017.

(56) References Cited

U.S. PATENT DOCUMENTS

| | | | |
|---|---|---|---|
| 4,844,905 | A | 7/1989 | Ichikawa et al. |
| 6,340,475 | B2 | 1/2002 | Shell et al. |
| 6,488,962 | B1 | 12/2002 | Berner et al. |
| 6,531,153 | B2 | 3/2003 | Seth et al. |
| 6,635,280 | B2 | 10/2003 | Shell et al. |
| 6,682,759 | B2 | 1/2004 | Lim et al. |
| 6,723,340 | B2 | 4/2004 | Gusler et al. |
| 7,094,427 | B2 | 8/2006 | Han et al. |
| 7,776,345 | B2 * | 8/2010 | Dudhara ............ A61K 9/0007 424/400 |
| 7,976,870 | B2 | 7/2011 | Berner et al. |
| 8,043,630 | B2 | 10/2011 | Berner et al. |
| 8,329,215 | B2 | 12/2012 | Berner et al. |
| 8,685,450 | B2 | 4/2014 | Lim et al. |
| 8,945,619 | B2 | 2/2015 | Berner et al. |
| 8,999,388 | B2 | 4/2015 | Lim et al. |
| 9,161,911 | B2 | 10/2015 | Hou et al. |
| 9,439,851 | B2 | 9/2016 | Dharmadhkari et al. |
| 9,566,258 | B2 | 2/2017 | Hou et al. |
| 9,572,780 | B2 | 2/2017 | Lim et al. |
| 9,597,338 | B2 | 3/2017 | Berner et al. |
| 9,937,142 | B2 | 4/2018 | Hou et al. |
| 9,980,903 | B2 | 5/2018 | Berner et al. |
| 2002/0051820 | A1 | 5/2002 | Shell et al. |
| 2004/0180086 | A1 | 9/2004 | Ramtoola et al. |
| 2005/0013863 | A1 | 1/2005 | Lim et al. |
| 2009/0028941 | A1 | 1/2009 | Cowles et al. |
| 2010/0112053 | A1 | 5/2010 | Momose et al. |
| 2013/0217777 | A1 | 8/2013 | Kirkorian et al. |
| 2014/0242168 | A1 | 8/2014 | Schiller et al. |
| 2014/0348936 | A1 | 11/2014 | Reyes et al. |
| 2015/0231078 | A1 | 8/2015 | Gerard et al. |
| 2016/0038411 | A1 | 2/2016 | Cowles et al. |
| 2016/0193155 | A1 | 7/2016 | Sharma et al. |
| 2016/0256393 | A1 | 9/2016 | Gerard et al. |
| 2017/0172930 | A1 | 6/2017 | Berner et al. |
| 2017/0319698 | A1 | 11/2017 | Vergnault et al. |

FOREIGN PATENT DOCUMENTS

| | | |
|---|---|---|
| WO | WO 02/000213 A1 | 1/2002 |
| WO | WO 2004/066981 A1 | 8/2004 |
| WO | WO 2008/068731 A1 | 6/2008 |

OTHER PUBLICATIONS

Deshpande et al., "Evaluation of films used in development of a novel controlled-release system for gastric retention," International Journal of Pharmaceutics, 159:255-258 (1997).

Huang et al., "An investigation of acetylcholine released in skeletal muscle and protein unbound drug released in blood based on the pyridostigmine bromide (pretreatment drug) sustained-release pellets by microdialysis technique in the rabbit model," Neuroscience Letters 416:302-306 (2007).

International Search Report and Written Opinion dated Oct. 2, 2019 in International Application No. PCT/US2019/037795.

U.S. Appl. No. 16/319,086, filed Jan. 18, 2019.

U.S. Appl. No. 16/445,110, filed Jun. 18, 2019.

International Search Report and Written Opinion dated Aug. 27, 2018 in International Application No. PCT/US2018/038118.

* cited by examiner

EXTENDED RELEASE COMPOSITIONS COMPRISING PYRIDOSTIGMINE

1. RELATED APPLICATIONS

This application is a continuation-in-part of U.S. patent application Ser. No. 16/445,110 (the '110 application), filed Jun. 18, 2019, which is continuation-in-part of International Application No. PCT/US2018/038118, filed Jun. 18, 2018, which claims priority to U.S. Provisional Patent Application No. 62/520,796, filed Jun. 16, 2017. The '110 application also claims priority to U.S. Provisional Patent Application No. 62/725,024, filed Aug. 30, 2018, and U.S. Provisional Patent Application No. 62/826,402, filed Mar. 29, 2019. The disclosures of all applications noted above are hereby incorporated by reference herein in their entireties.

2. TECHNICAL FIELD

The present disclosure provides extended release pyridostigmine compositions suitable for once-daily administration. The compositions are administered as a single dosage unit/day (QD) to provide extended release of pyridostigmine bromide for at least about 14 hours (e.g., at least about 18 hours). Such extended release compositions are particularly beneficial in overcoming the gastrointestinal (GI) side effects experienced with currently pyridostigmine products by providing and maintaining therapeutic plasma concentrations for extended time periods, e.g., at least about 14 hours. The extended release pyridostigmine compositions of the disclosure include matrix tablets, gastroretentive tablets, and pellets, the latter being suitable for dosing in capsules, tablets, and sachets, and for sprinkling on foodstuffs. In certain embodiments, the gastroretentive compositions of the disclosure include an immediate release (IR) layer (containing pyridostigmine bromide) and an extended release (ER) component. The immediate release layer minimizes the lag time associated with the presence of an extended release component alone. The compositions provide therapeutic drug plasma concentrations for extended periods of time; and the reduction/elimination of the initial burst release/dose dumping seen with marketed pyridostigmine products aids in reducing GI side effects. The extended release component provides and maintains therapeutic plasma concentrations of the drug for a period of at least about 14 hours.

3. BACKGROUND

Pyridostigmine bromide is an active cholinesterase inhibitor that does not cross the blood-brain barrier. It works by increasing levels of acetylcholine, a chemical released by motor neurons to activate muscles. It is commonly used in muscle tone recovery in myasthenia gravis (MG), postoperative functional bowel bloating, and urinary retention. It has also been approved for combat use by United States military personnel, i.e., pyridostigmine bromide has been approved by the U.S. Food and Drug Administration (FDA) to increase survival after exposure to Soman "nerve gas" poisoning.

The time-to-maximum peak plasma concentration of oral pyridostigmine is 1-2 hours and its elimination half-life is about 3-5 hours. Pyridostigmine undergoes hydrolysis by the enzyme cholinesterase and is metabolized in the liver. It is excreted in the urine as a combination of unchanged drug and pyridostigmine metabolites. The bioavailability of pyridostigmine is reported to be about 10-20% (NDA #020414).

Due to suboptimal pharmacokinetics of pyridostigmine, including a short duration of action, MG patients must take multiple tablets, occasionally multiple times a day. The patients experience "wearing off" of the drug and worsening of symptoms prior to the next dose, suffer from poor tolerability at higher dose levels, and experience difficulty adhering to the required frequent dosing regimen.

The FDA has approved Valeant Pharmaceutical's MESTINON® (pyridostigmine bromide injection, suspension, tablets, and extended release (ER) tablets) for the treatment of MG. The MESTINON® injection contains 5 mg/ml pyridostigmine bromide; MESTINON® suspension contains 60 mg/teaspoon pyridostigmine bromide; MESTINON® tablets contain 60 mg pyridostigmine bromide; and ER MESTINON® TIMESPAN® tablets contain 180 mg pyridostigmine bromide. The average daily dose of pyridostigmine is ten 60 mg tablets, ten teaspoons of suspension, or between one and three 180 mg ER tablets, spaced to provide maximum relief. The ER 180 mg tablets are administered, as 1-3 tablets, depending upon severity of the condition, once- or twice-daily with an interval of at least 6 hours between doses.

The currently approved ER pyridostigmine products provide an initial burst release/dose dumping, followed by extended release of the remaining dose of pyridostigmine bromide. The approved ER formulations release about 35-55% of pyridostigmine after one hour, about 65-85% after four hours, and about 85% after eight hours (in vitro dissolution). As approximately 40-50% of the drug can be released during first hour with the approved/marketed ER product, it has limited clinical utility. Presently marketed pyridostigmine products are plagued by a spike in concentration, or dose dumping, while attempting to maintain therapeutic plasma concentrations of the drug for extended periods of time. Initial burst release/dose dumping of the drug is associated with various side effects, e.g., nausea, vomiting, diarrhea, abdominal cramps, fasciculations, weakness, increased peristalsis, increased salivation, increased bronchial secretions, miosis, and diaphoresis. Such an initial spike in vivo, causing unwanted side effects, can be compared with in vitro release of at least about 50% of the pyridostigmine bromide within two hours of dissolution into a dissolution medium mimicking gastric fluid conditions.

It is particularly desirable for MG patients to have a constant level of pyridostigmine to improve therapeutic outcome and quality of life, and to reduce side effects. There remains a need for ER pyridostigmine compositions that are designed to prolong and maintain therapeutic plasma concentration of pyridostigmine, and minimize side effects, by controlling the initial burst release/dose dumping of the drug. There remains a need in the art for ER pyridostigmine compositions that provide a minimal lag time, provide extended release with minimal initial burst release/dose dumping, and maintain a stable therapeutic plasma concentration of the drug for extended periods of time. There remains a need in the art for extended release pyridostigmine compositions containing an immediate release layer containing pyridostigmine bromide to eliminate the lag time, and an extended release component to provide extended release with minimal initial burst release/dose dumping of the drug; for extended release pyridostigmine compositions that will allow for reduced frequency of administration of the composition, improve patient compliance, and reduce side effects associated with an unwanted initial burst in drug release/dose dumping; and for development of a once-a-day extended release pyridostigmine compositions that can provide an extended release for at least about 16 hours (preferably about 24 hours), and reduce side effects associated with dose dumping of the drug.

4. SUMMARY

In certain embodiments, the present disclosure provides for a gastroretentive dosage form comprising an immediate release layer and an extended release component, wherein the immediate release layer comprises between about 10 mg and about 60 mg pyridostigmine bromide, and the extended release component comprises a core and a permeable elastic membrane surrounding the core. The core comprises between about 50 mg and about 400 mg pyridostigmine bromide; hypromellose in an amount of between about 5 wt % and about 35 wt %, based on the total weight of the core; succinic acid; a carbonate salt; and a bicarbonate salt. The permeable elastic membrane comprises a plasticizer in an amount of between about 5 wt % and about 25 wt % of the membrane composition, and a copolymer based on ethyl acrylate, methyl methacrylate, and trimethylammonioethyl methacrylate chloride in powder form (1:2:0.2), in an amount of between about 75 wt % and about 95 wt % of the membrane composition, and wherein the dosage form provides an extended release of pyridostigmine bromide for at least about 14 hours.

In certain other embodiments, the dosage form of the present disclosure provides an in vitro release of between about 20% and about 35% of the pyridostigmine bromide within about 2 hours of dissolution in a dissolution medium comprising pH 4.5 acetate buffer with 100 mM NaCl.

In certain embodiments, the dosage form of the present disclosure floats in about 40 minutes or less in a dissolution medium comprising pH 4.5 acetate buffer with 100 mM NaCl.

In certain embodiments, the dosage form of the present disclosure, when in contact with gastric fluid, swells in about 60 minutes or less to a size that prevents its passage through pyloric sphincter.

In certain embodiments, the dosage form of the present disclosure maintains its integrity in a swollen state for a period of at least about 14 hours.

In certain embodiments, the dosage form of the present disclosure further includes crospovidone as a wicking agent.

In certain embodiments, the carbonate and bicarbonate salts comprise $CaCO_3$ and $NaHCO_3$, respectively.

In certain embodiments, the plasticizer is triethyl citrate.

In certain embodiments, the dosage form further includes a seal coat between the permeable elastic membrane and the immediate release layer.

In certain embodiments, the dosage form does not include a seal coat between the core and the permeable elastic membrane.

In certain embodiments, the dosage form further includes an orifice passing through the permeable elastic membrane and the seal coat.

In certain embodiments, the dosage form is a tablet.

In certain embodiments, the dosage form is a tablet that is suitable for once daily administration and is administered as a single tablet/day.

In certain embodiments, the hypromellose is a mixture of a low viscosity hypromellose and a high viscosity hypromellose. In certain embodiments, the low viscosity hypromellose has a viscosity of between about 80 mPa·s and about 120 mPa·s. In certain embodiments, the high viscosity hypromellose has a viscosity of between about, 2,700 mPa·s and about 5,040 mPa·s.

In certain embodiments, the present disclosure provides for a gastroretentive dosage form comprising an immediate release layer and an extended release component, wherein the immediate release layer comprises between about 10 mg and about 60 mg pyridostigmine bromide, and the extended release component comprises a core and a permeable elastic membrane surrounding the core. The core comprises between about 50 mg and about 400 mg pyridostigmine bromide; a high viscosity hypromellose in an amount of between about 5 wt % and about 35 wt %, based on the total weight of the core; succinic acid; a carbonate salt; and a bicarbonate salt, wherein the high viscosity hypromellose has a viscosity of between about, 2,700 mPa·s and about 5,040 mPa·s; wherein each of sodium bicarbonate and calcium carbonate is present in equimolar amounts with respect to succinic acid; and wherein each of sodium bicarbonate, calcium carbonate, and succinic acid is present in an amount of between about 1 wt % and about 10 wt %, based on the total weight of the core. The permeable elastic membrane comprises a plasticizer in an amount of between about 5 wt % and about 25 wt % of the membrane composition, and a copolymer based on ethyl acrylate, methyl methacrylate, and trimethylammonioethyl methacrylate chloride in powder form (1:2:0.2), in an amount of between about 75 wt % and about 95 wt % of the membrane composition. The dosage form floats in about 40 minutes or less in pH 4.5 acetate buffer with 100 mM NaCl.

In certain embodiments, the disclosure provides for a gastroretentive dosage form comprising a core and a permeable elastic membrane surrounding the core, wherein the core comprises between about 50 mg and about 400 mg pyridostigmine bromide, hypromellose in an amount of between about 5 wt % and about 35 wt %, based on the total weight of the core, succinic acid, a carbonate salt, and a bicarbonate salt, wherein the hypromellose has a viscosity of between about, 2,700 mPa·s and about 5,040 mPa·s; each of sodium bicarbonate and calcium carbonate is present in equimolar amounts with respect to succinic acid; and each of sodium bicarbonate, calcium carbonate, and succinic acid is present in an amount of between about 1 wt % and about 10 wt %, based on the total weight of the core. The permeable elastic membrane comprises a plasticizer in an amount of between about 5 wt % and about 25 wt % of the membrane composition, and a copolymer based on ethyl acrylate, methyl methacrylate, and trimethylammonioethyl methacrylate chloride in powder form (1:2:0.2), in an amount of between about 75 wt % and about 95 wt % of the membrane composition. The dosage form floats in about 40 minutes or less in pH 4.5 acetate buffer with 100 mM NaCl, and the dosage form provides an extended release of pyridostigmine bromide for at least about 14 hours.

5. BRIEF DESCRIPTION OF THE DRAWINGS

Figure 1B:
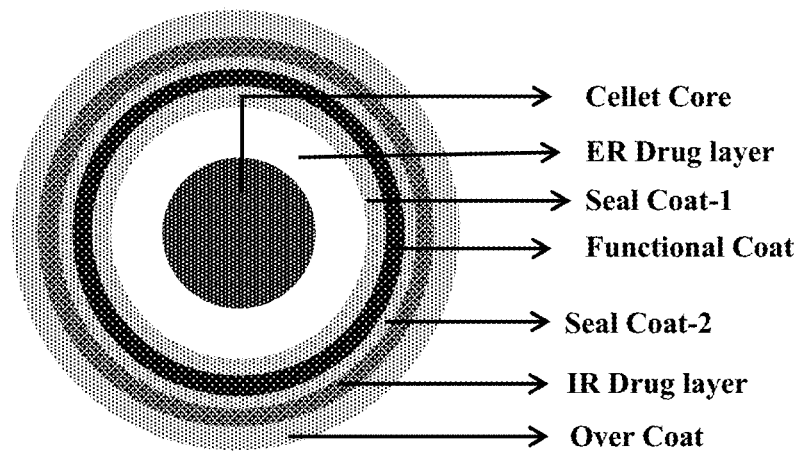

FIGS. 1A and 1B depict schematic representations of pyridostigmine pellets, with and without an immediate release drug layer. FIG. 1A depicts a schematic representation of a pyridostigmine pellet containing a cellet core, an extended release drug layer, a seal coat and a functional coat. FIG. 1B depicts a schematic representation of a pyridostigmine pellet containing a cellet core, an extended release drug layer, a seal coat, a functional coat, a second seal coat, an immediate release drug layer, and an over coat.

Figure 2A:
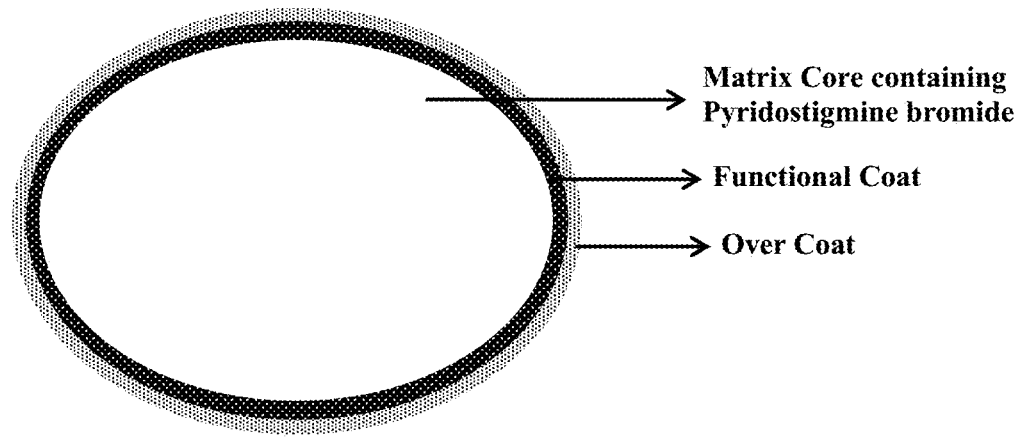
Figure 2B:
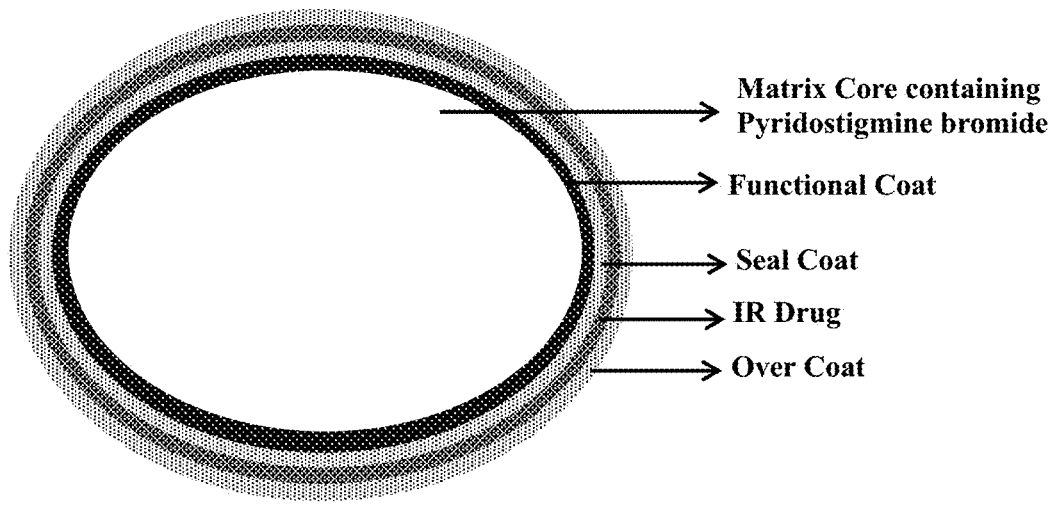

FIGS. 2A and 2B depict schematic representations of pyridostigmine matrix tablets. FIG. 2A depicts a schematic representation of a pyridostigmine matrix tablets containing a matrix core containing pyridostigmine bromide, a functional coat and an over coat. FIG. 2B depicts a schematic representation of a pyridostigmine matrix tablets containing a matrix core containing pyridostigmine bromide, a functional coat, an immediate release drug layer containing pyridostigmine bromide, and an over coat.

Figure 3A:
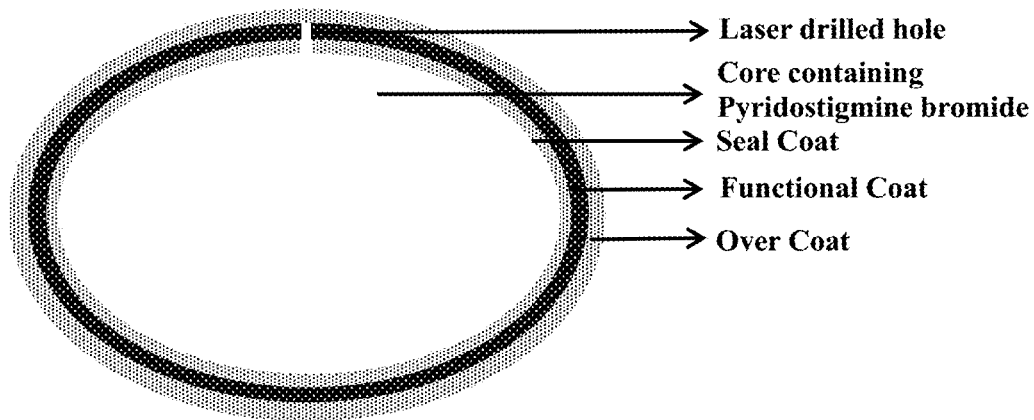
Figure 3B:
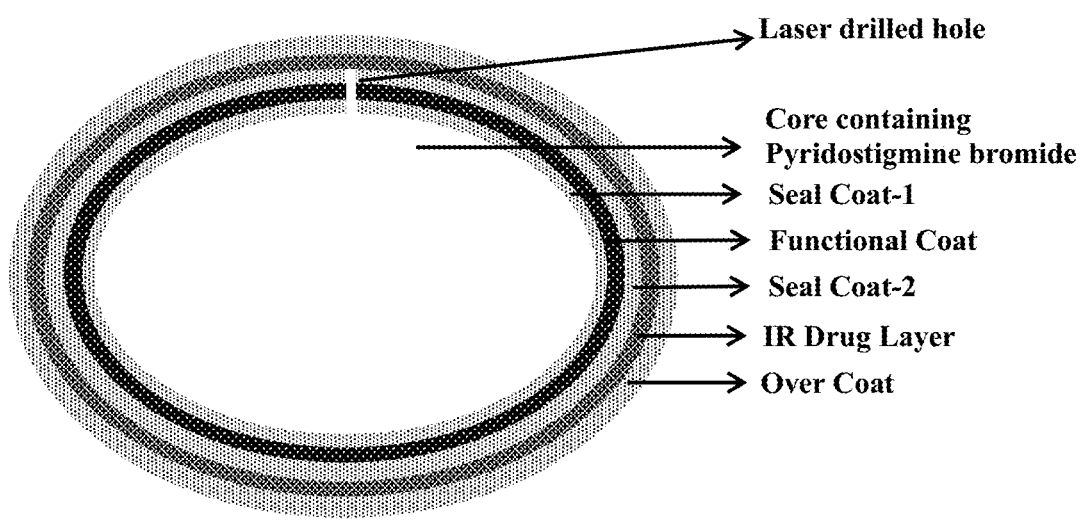

FIGS. 3A and 3B depict schematic representations of pyridostigmine gastroretentive tablets. FIG. 3A depicts a schematic representation of a pyridostigmine gastroretentive tablet containing a core containing pyridostigmine bromide, a seal coat, a functional coat and an over coat. FIG. 3B depicts a schematic representation of a pyridostigmine gastroretentive tablet containing a core containing pyridostigmine bromide, a seal coat, a functional coat, an immediate release drug layer containing pyridostigmine bromide, and an over coat.

Figure 4:
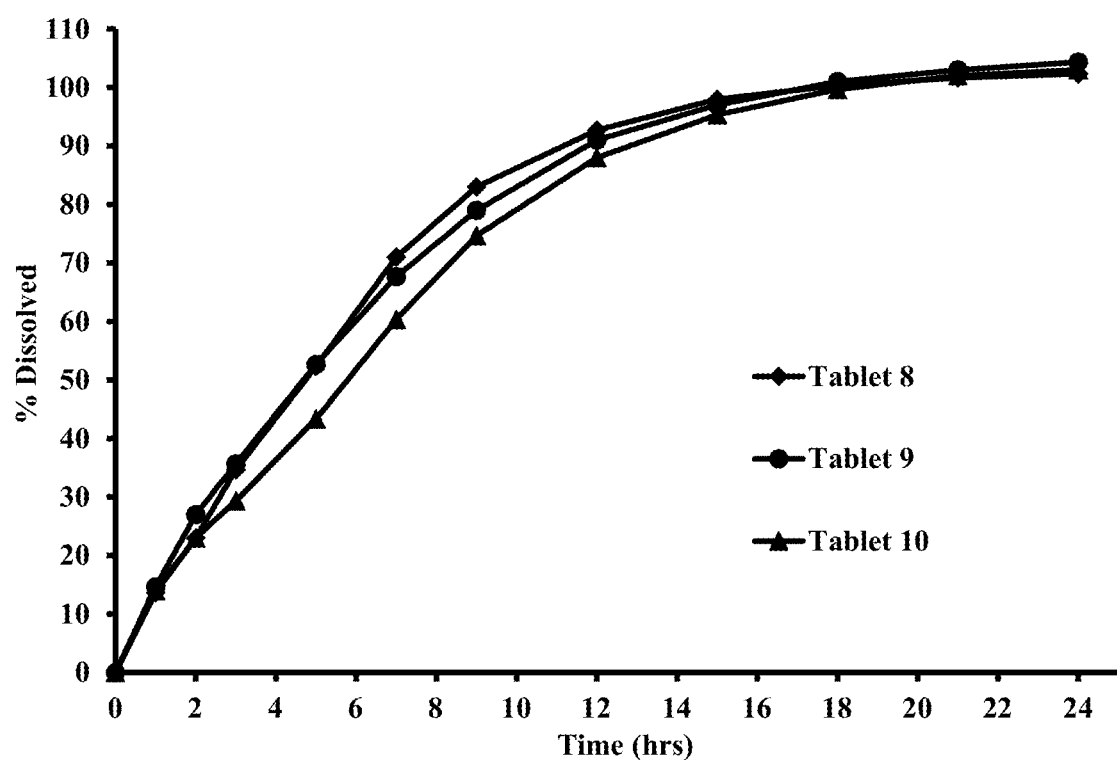

FIG. 4 compares dissolution profiles of pyridostigmine bromide from Tablets 8, 9, and 10, in about 900 ml of pH 4.5 acetate buffer, using USP Apparatus I—Custom basket, at about 100 rpm and about 37° C.

Figure 5:
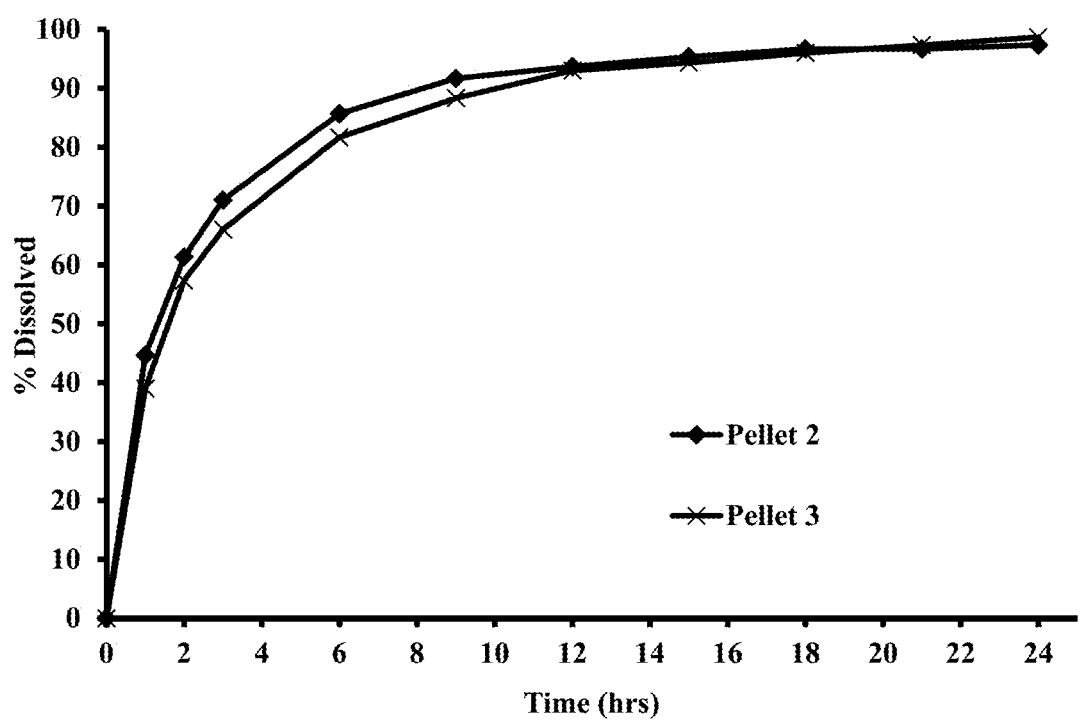

FIG. 5 compares dissolution profiles of pyridostigmine bromide from Pellets 2 and 3, in 200 ml of 50 mM phosphate buffer at pH 6.8, using USP Apparatus II (Paddle), at about 50 rpm and about 37° C.

Figure 6:
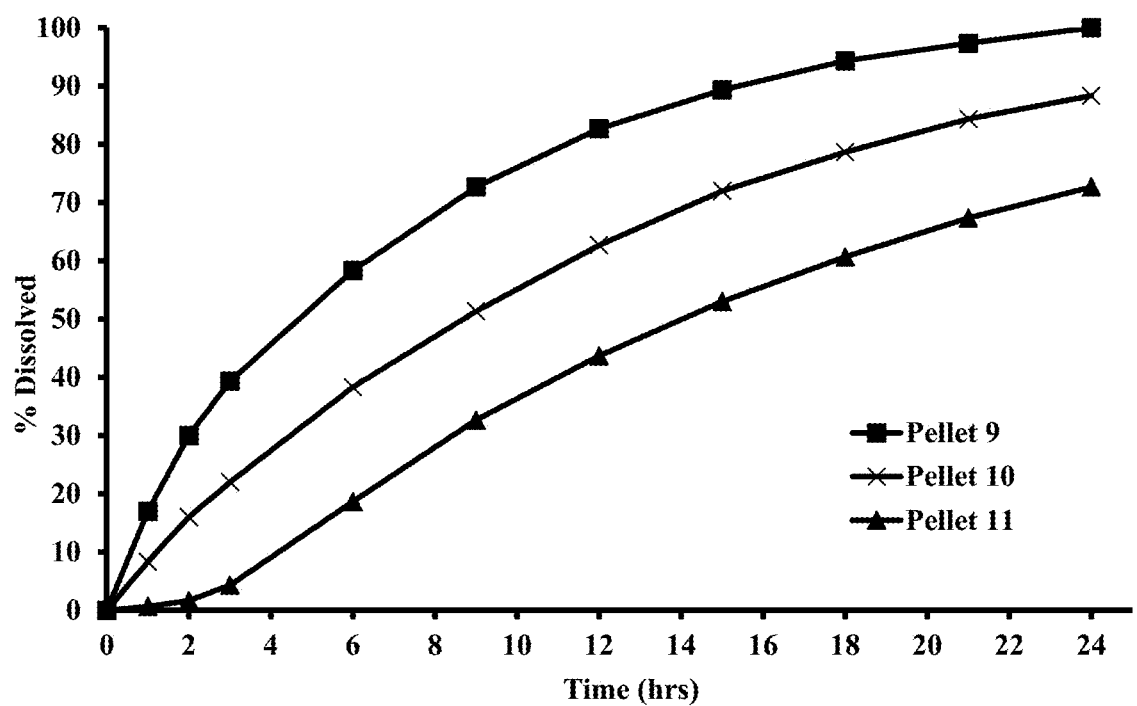

FIG. 6 compares dissolution profiles of pyridostigmine bromide from Pellets 9, 10, and 11, in 200 ml of 50 mM phosphate buffer at about pH 6.8, using USP Apparatus II (Paddle), at about 50 rpm and about 37° C.

Figure 7:
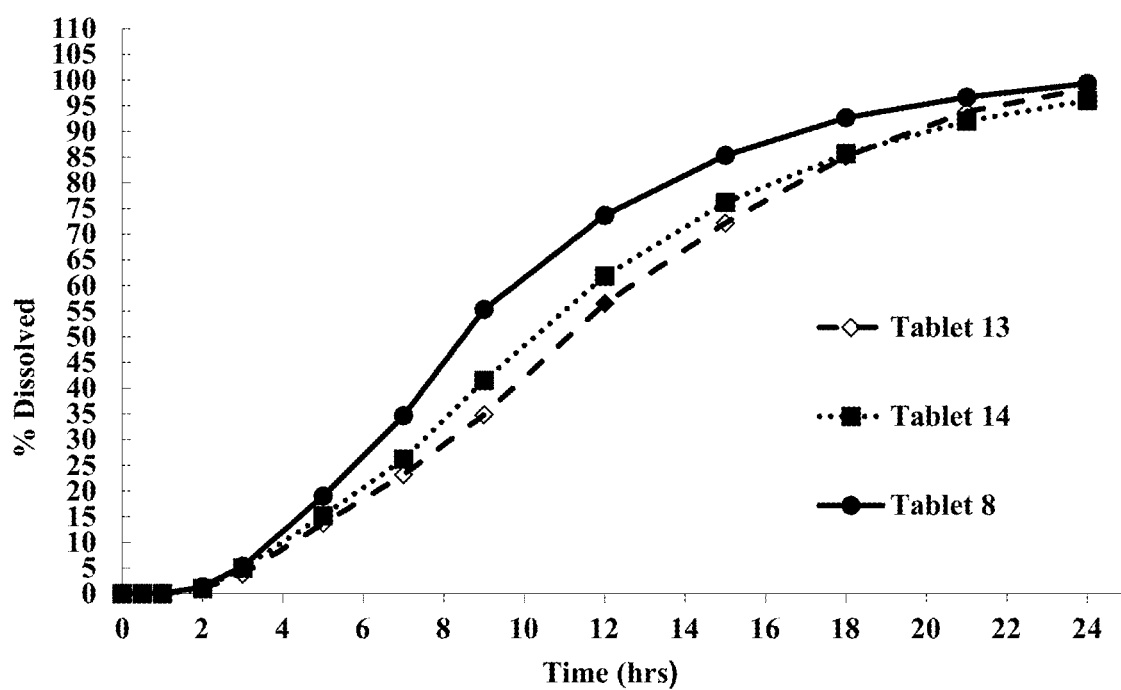

FIG. 7 compares dissolution profiles of Tablets 8, 13, and 14 in about 900 ml of pH 5.0 acetate buffer containing 150 mM NaCl, using USP Apparatus I (Custom Basket), at about 100 rpm and about 37° C. FIG. 7 shows that Tablets 13 and 14 (containing hydroxypropyl methylcellulose in an amount of about 30% w/w of the tablet core; and equimolar amounts of succinic acid and each of the two gas-generating agents) exhibit about 10-15% slower drug release compared to Tablet 8 (containing hydroxypropyl methylcellulose in an amount of about 20% w/w of the tablet core; and non-equimolar amounts of succinic acid and each of the two gas-generating agents).

Figure 8:
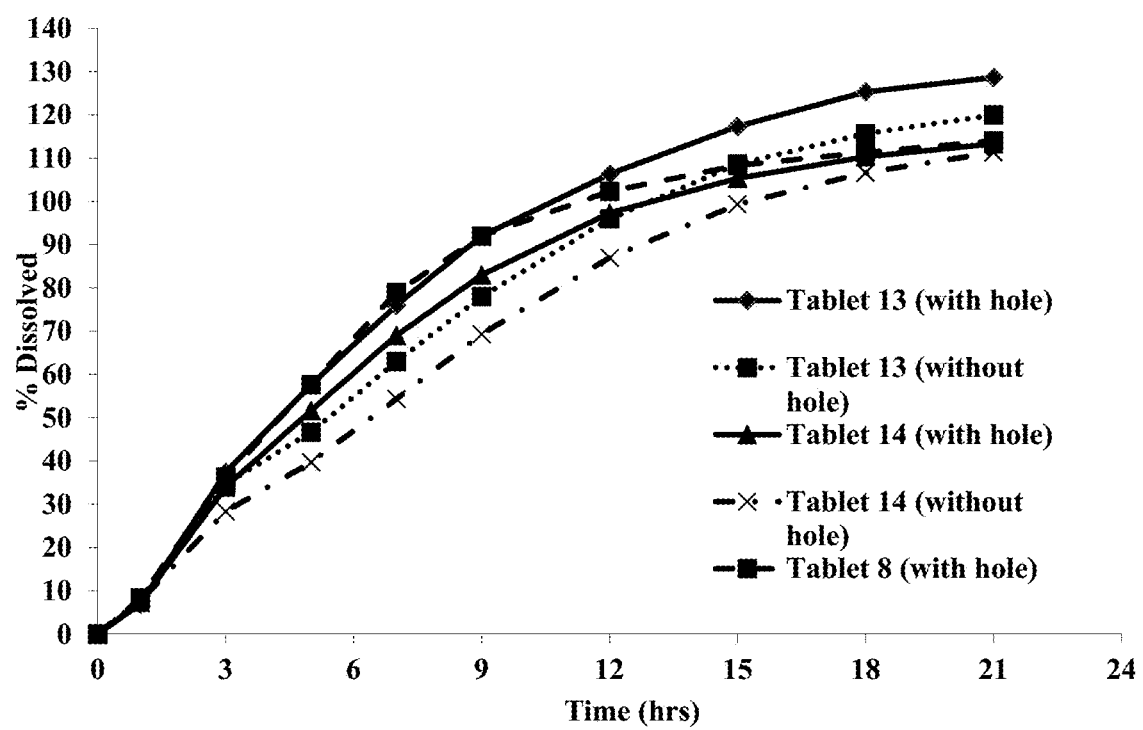

FIG. 8 compares dissolution profiles of Tablets 13 and 14, each with and without a hole in the membrane/functional coat, and Tablet 8 (with a hole). The dissolution testing was conducted in about 250 ml of pH 3.0 media containing about 100 mM NaCl, using USP Apparatus III (BIO-DIS), at about 25 dpm and about 37° C.

Figure 9:
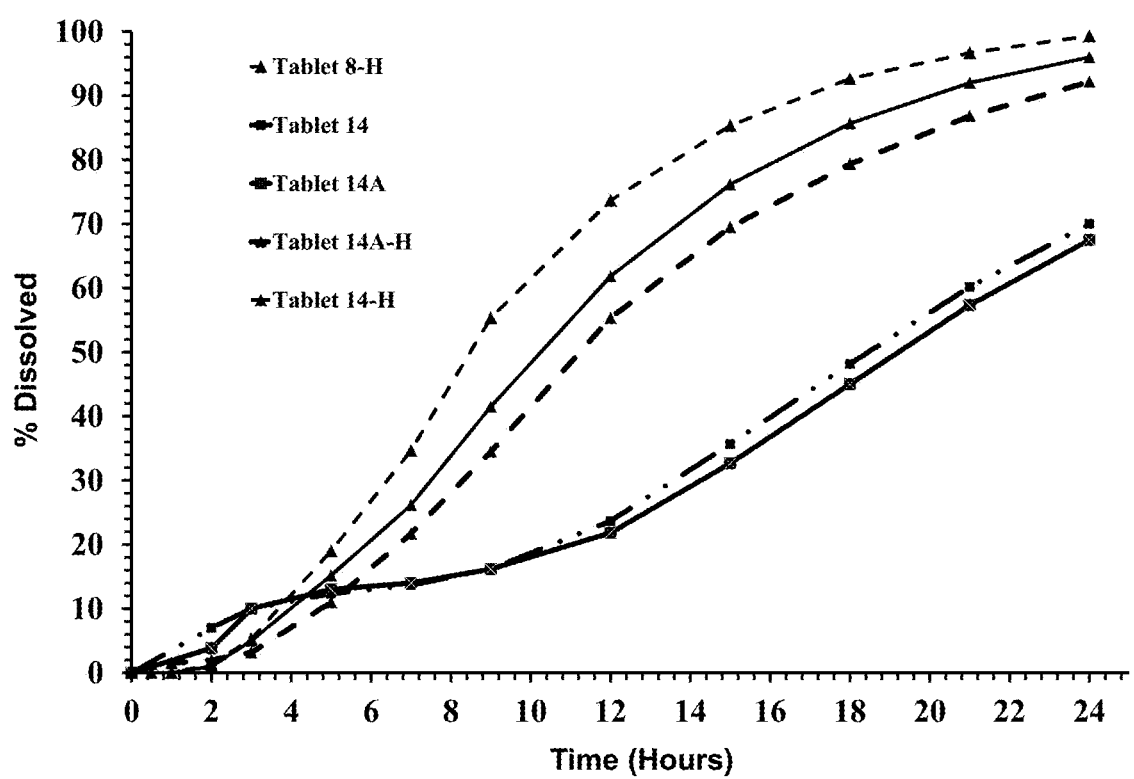

FIG. 9 compares dissolution profiles of Tablet 8 (with a hole; "8-H"), and Tablets 14 and 14A, each with a hole ("H") and without a hole in the membrane. The dissolution testing was conducted in about 900 ml of pH 5.0 acetate buffer containing about 150 mM NaCl, using USP Apparatus I (Custom Basket), at about 100 rpm and about 37° C.

Figure 10:
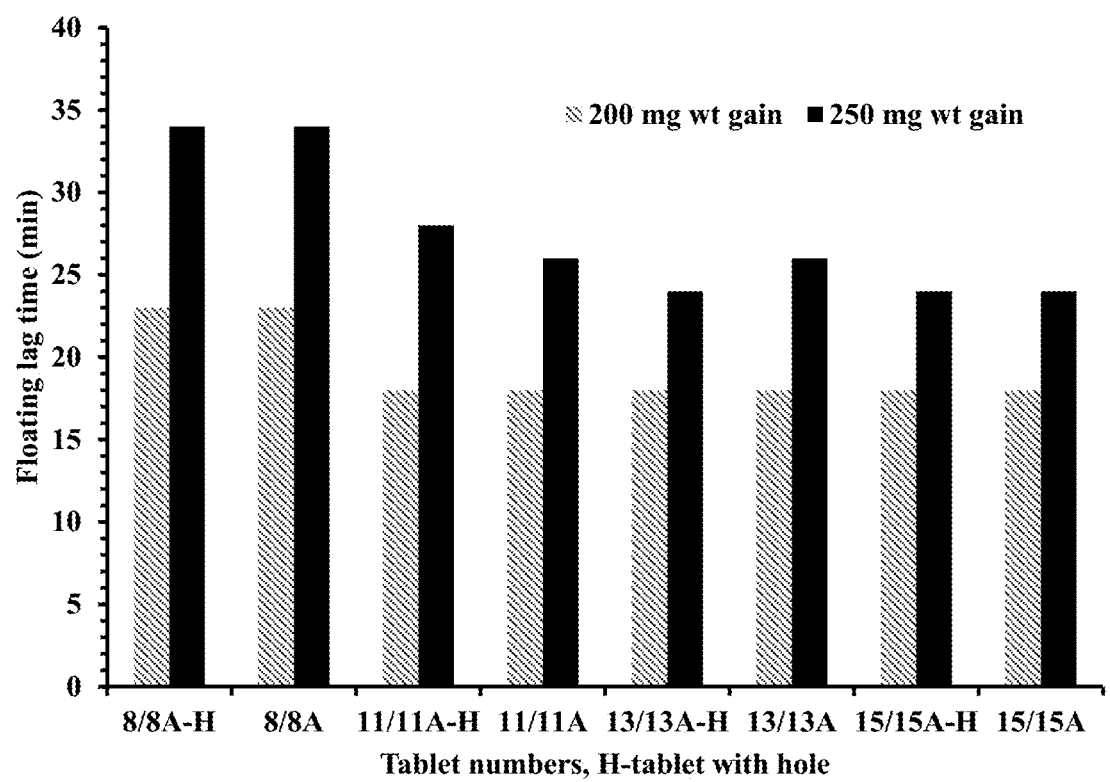

FIG. 10 compares floating lag times of Tablets 8, 11, 13, and 15, with ("H") and without a hole, at 200 mg functional coating weight gain, and Tablets 8A, 11A, 13A, and 15A, with and without a hole, at 250 mg functional coating weight gain. The flotation studies were performed using a Rotating Bottle method at about 5 rpm and about 37° C., in 200 ml of a dissolution medium at about pH 4.5 comprising about 100 mM NaCl.

Figure 11:
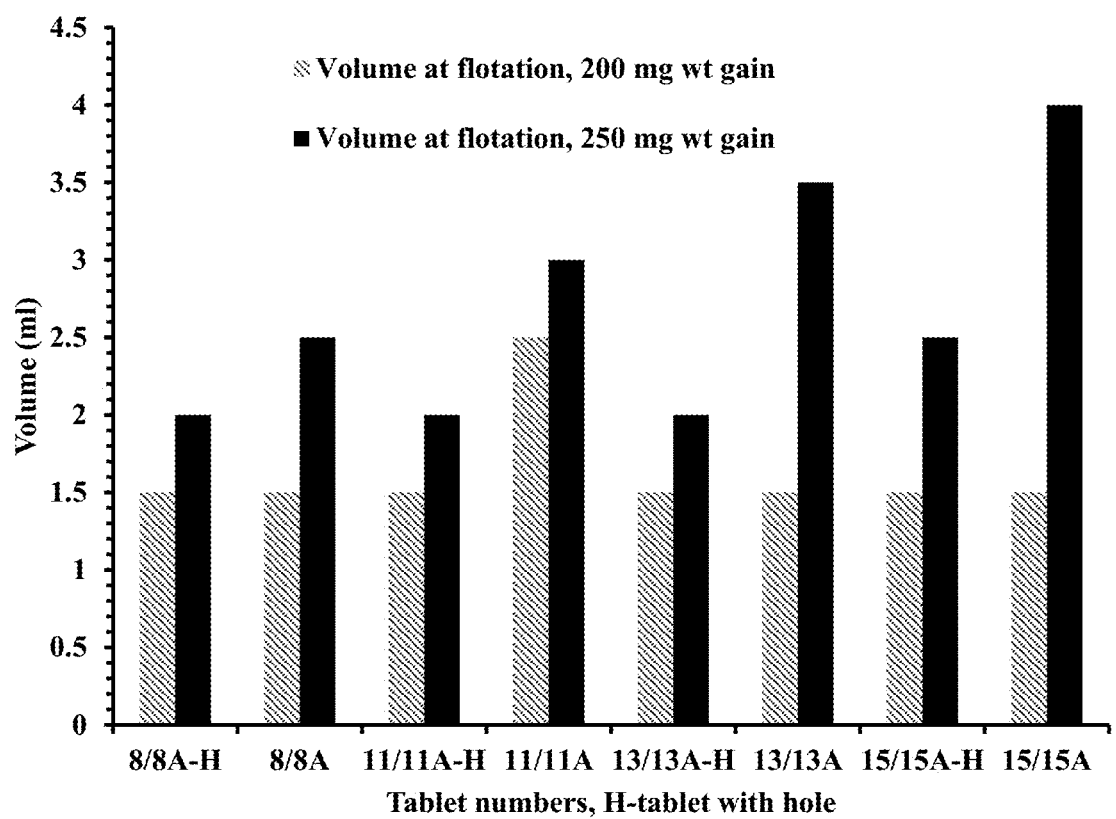

FIG. 11 compares volumetric expansion at flotation of Tablets 8, 11, 13, and 15, with ("H") and without a hole, at 200 mg functional coating weight gain, and Tablets 8A, 11A, 13A, and 15A, with and without a hole, at 250 mg functional coating weight gain. FIG. 11 demonstrates that tablets without a hole exhibit higher volume expansion compared to tablets with a hole at flotation. The volume expansion studies were performed, using a Rotating Bottle method at about 5 rpm and about 37° C., in 200 ml of pH 4.5 dissolution medium containing about 100 mM NaCl.

Figure 12:
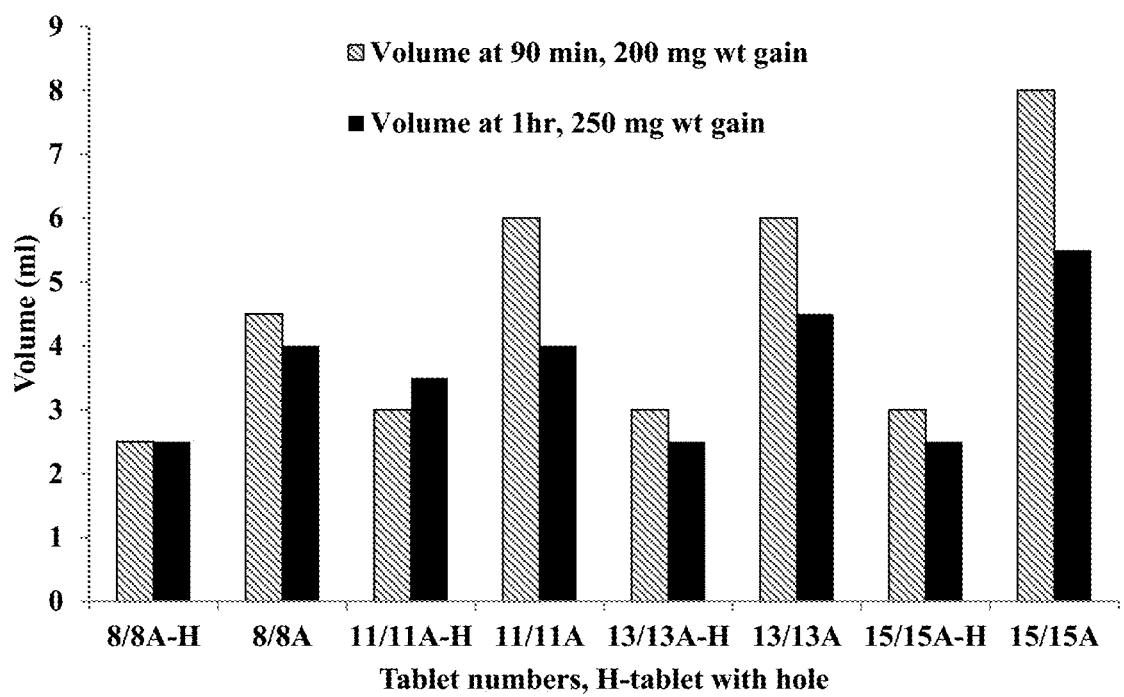

FIG. 12 compares volumetric expansion, at 90 minutes, of Tablets 8, 11, 13, and 15, with ("H") and without a hole, at 200 mg functional coating weight gain, and volumetric expansion, at one hour, of Tablets 8A, 11A, 13A, and 15A, with and without a hole, at 250 mg functional coating weight gain. FIG. 12 demonstrates that tablets without a hole exhibit higher volume expansion compared to tablets with a hole at both 90 minutes and one hour. The volume expansion studies were performed, using a Rotating Bottle method at about 5 rpm and about 37° C., in 200 ml of pH 4.5 acetate buffer containing about 100 mM NaCl.

Figure 13:
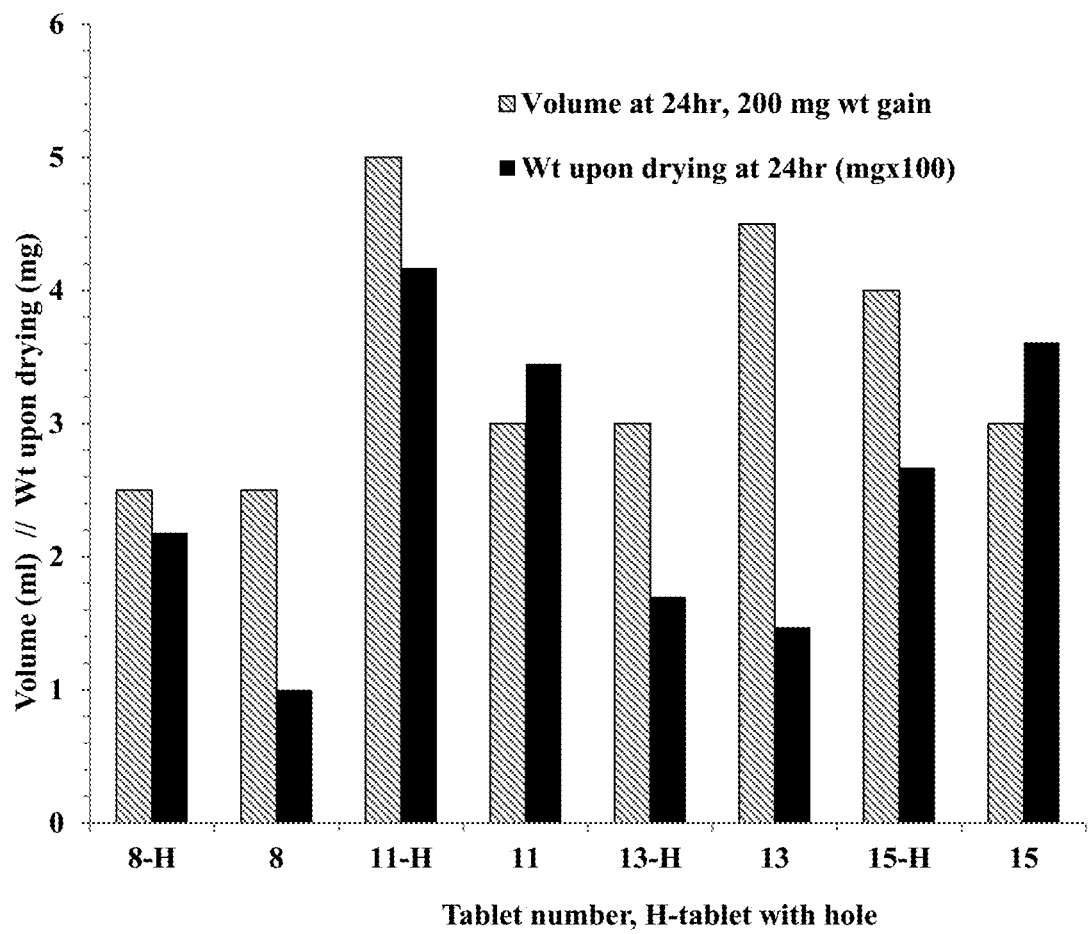

FIG. 13 compares volumetric expansion, and weight gain at 24 hours, of Tablets 8, 11, 13, and 15, with ("H") and without a hole, at 200 mg functional coating weight gain. The volume expansion studies were performed, using a Rotating Bottle method at about 5 rpm and about 37° C., in 200 ml of pH 4.5 acetate buffer containing about 100 mM NaCl. FIG. 13 demonstrates that tablets containing 200 mg of crospovidone (e.g., Tablets 11/11-H and 15/15-H) exhibit higher weight upon drying compared with tablets containing 100 mg of crospovidone (e.g., Tablets 8/8-H and 13/13-H).

Figure 14:
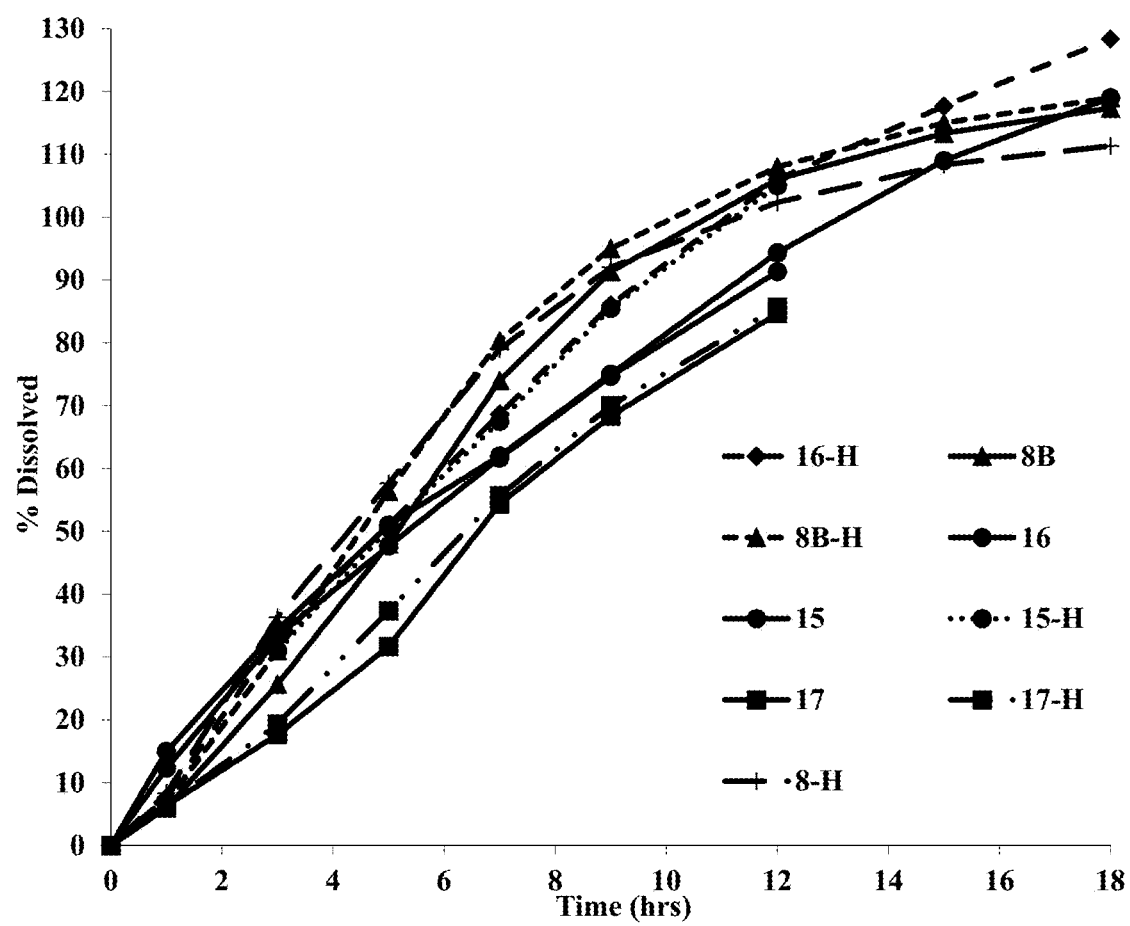

FIG. 14 compares dissolution profiles of Tablets 8B, 15, 16, and 17 without a hole, and Tablets 8, 8B, 15, 16, and 17 with a hole ("H"), using BIO-DIS method at about 20 dpm and about 37° C., in 250 ml of pH 3.0 dissolution medium containing about 100 mM NaCl. FIG. 14 demonstrates that tablets without a hole exhibit slower drug release rates compared to tablets with a hole.

Figure 15:
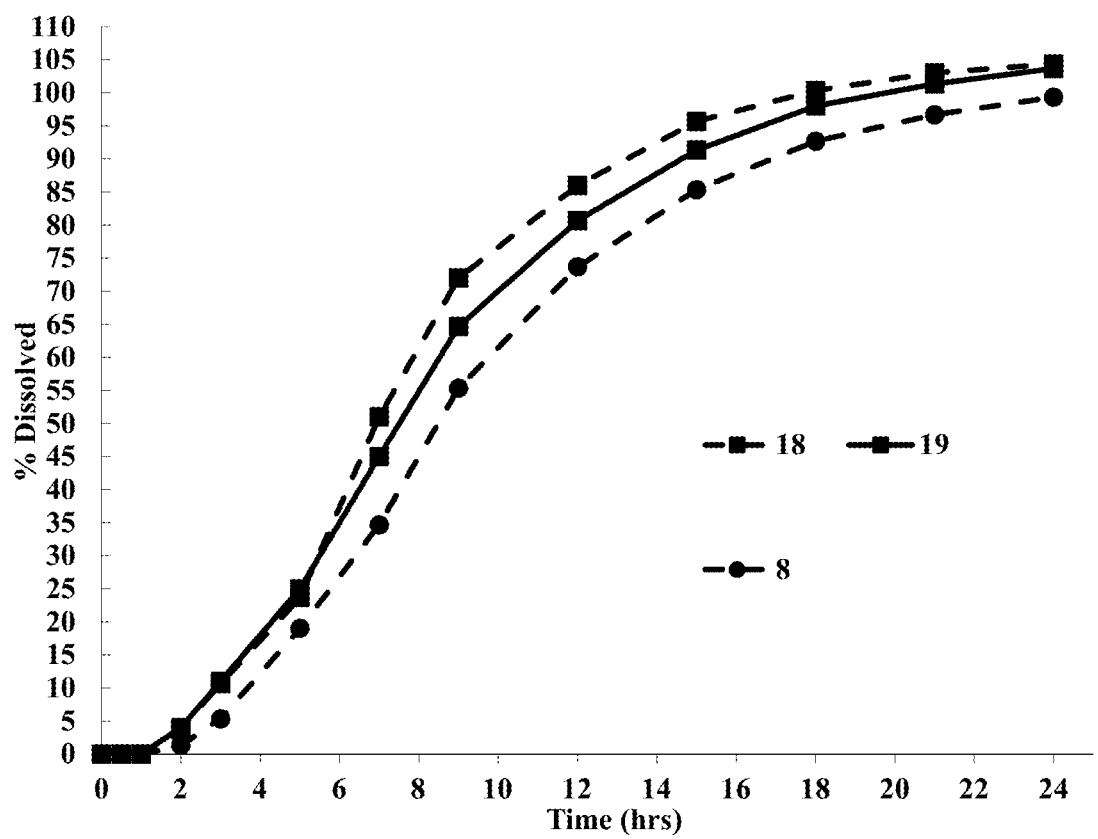

FIG. 15 shows the effect of crospovidone on release rates of pyridostigmine from the gastroretentive compositions of the disclosure. FIG. 15 compares dissolution profiles of Tablets 8, 18, and 19 in about 900 ml of pH 5.0 dissolution medium containing about 150 mM NaCl, 30 mM sodium acetate, and 17 mM acetic acid, using USP Apparatus I (Custom Basket), at about 100 rpm and about 37° C. FIG. 15 demonstrates that tablets containing 200 mg of crospovidone (Tablets 18 and 19) exhibit faster drug release compared to a tablet containing 100 mg of crospovidone (Tablet 8).

Figure 16:
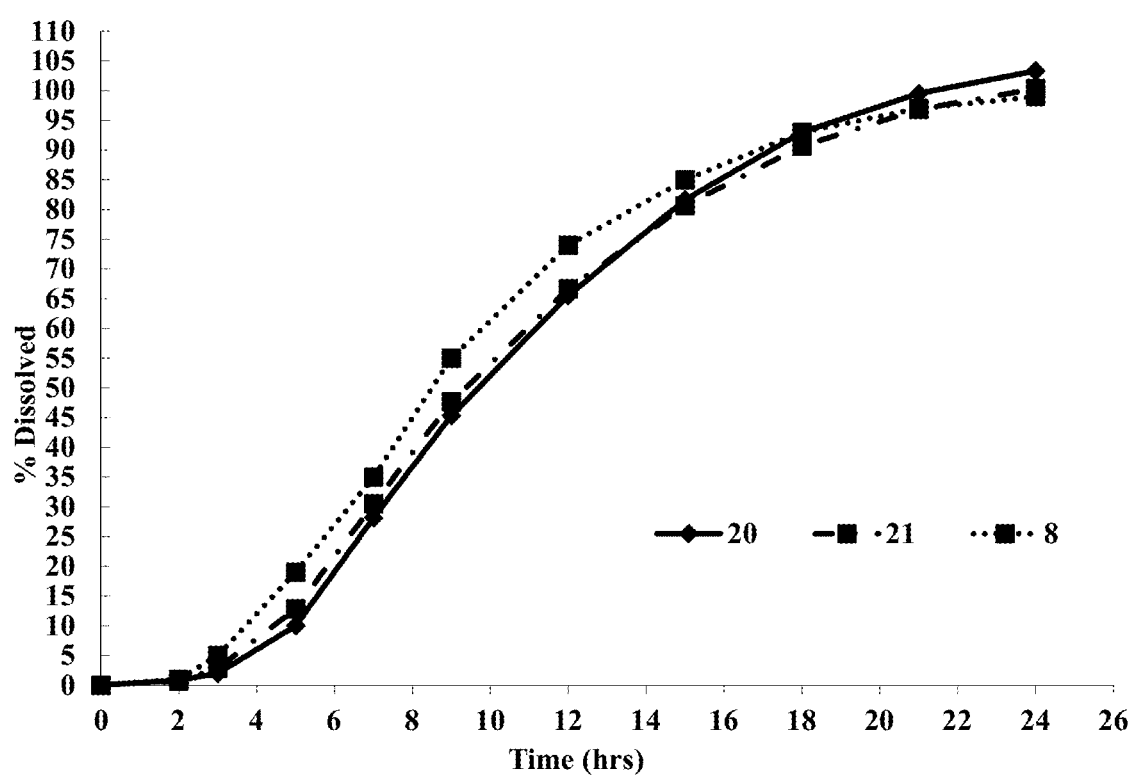

FIG. 16 compares dissolution profiles of tablets containing a mixture of BENECEL™ K4M PH DC and METHOCEL™ K100 Premium DC (Tablets 20 and 21) and a tablet containing BENECEL™ K4M PH DC only (Tablet 8) in about 900 ml of pH 5.0 acetate buffer containing about 150 mM NaCl, using USP Apparatus I (Custom Basket), at about 100 rpm and about 37° C. FIG. 16 demonstrates that tablets containing the mixture (Tablets 20 and 21) provide more controlled release compared to a tablet containing BENECEL™ K4M PH DC only (Tablet 8).

Figure 17:
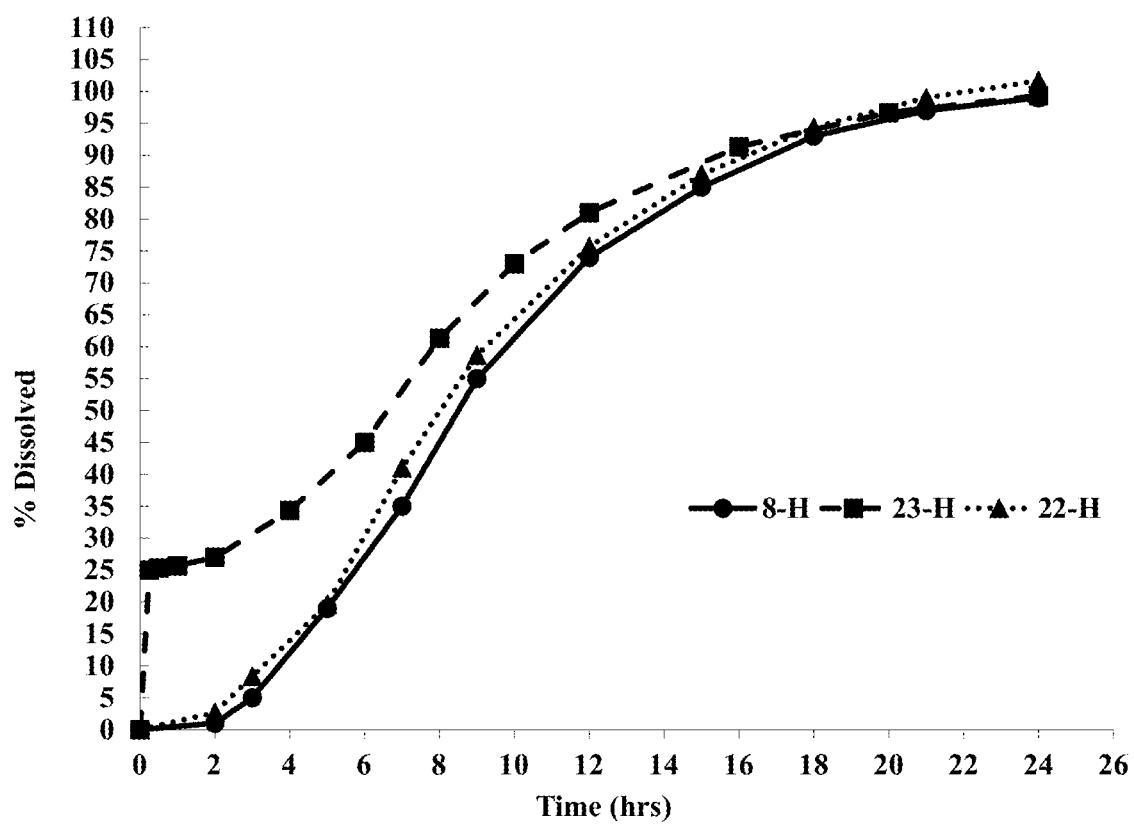

FIG. 17 compares dissolution profiles of tablets (all with a hole ("H")) containing an immediate release drug layer (Tablet 23) and tablets with no immediate release drug layer (Tablets 8 and 22) in about 900 ml of pH 5.0 acetate buffer containing about 150 mM NaCl, using USP Apparatus I (Custom Basket), at about 100 rpm and about 37° C. FIG. 17 demonstrates that the tablet containing an immediate release drug layer (Tablet 23) eliminates lag time compared to those that do not contain an immediate release drug layer (Tablets 8 and 22).

Figure 18:
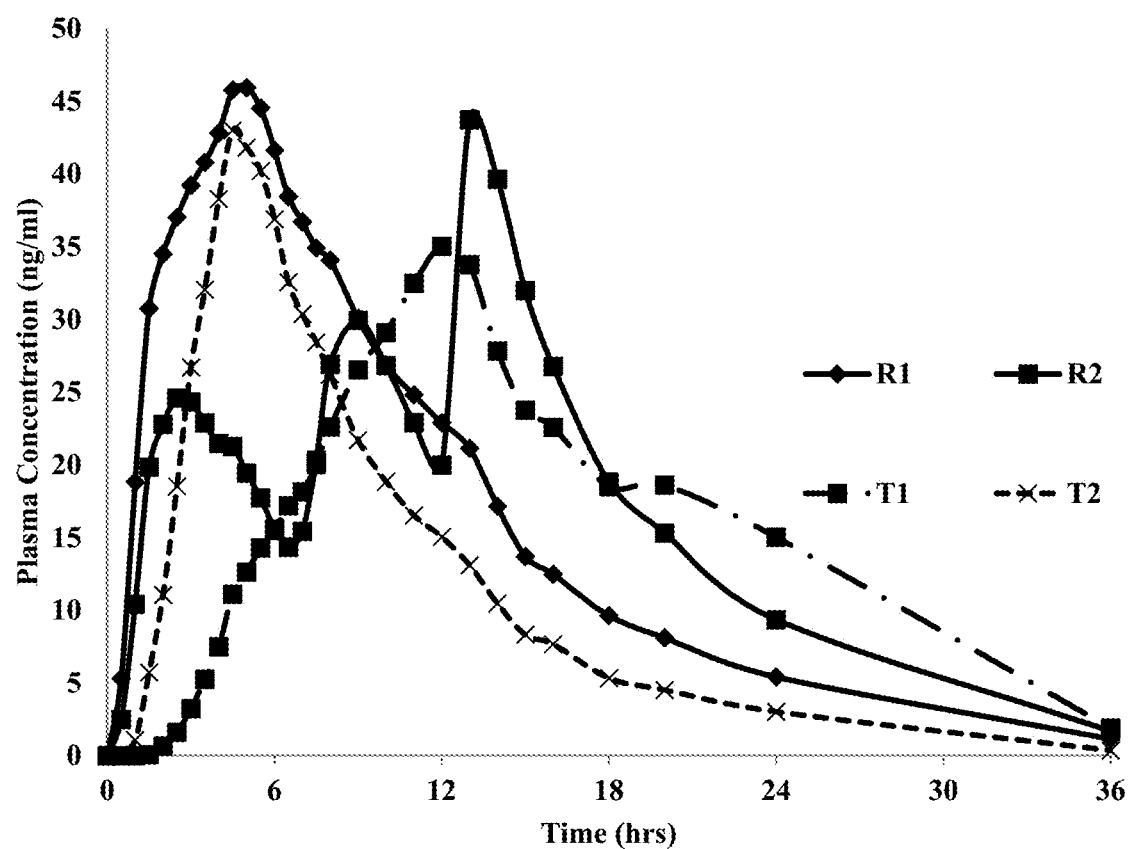

FIG. 18 compares pharmacokinetic data for gastroretentive Tablet 8 ($T_1$), pellet composition ($T_2$), and marketed pyridostigmine products, e.g., MESTINON® tablets ($R_2$) and ER MESTINON® (i.e., TIMESPAN)® tablets ($R_1$).

Figure 19:
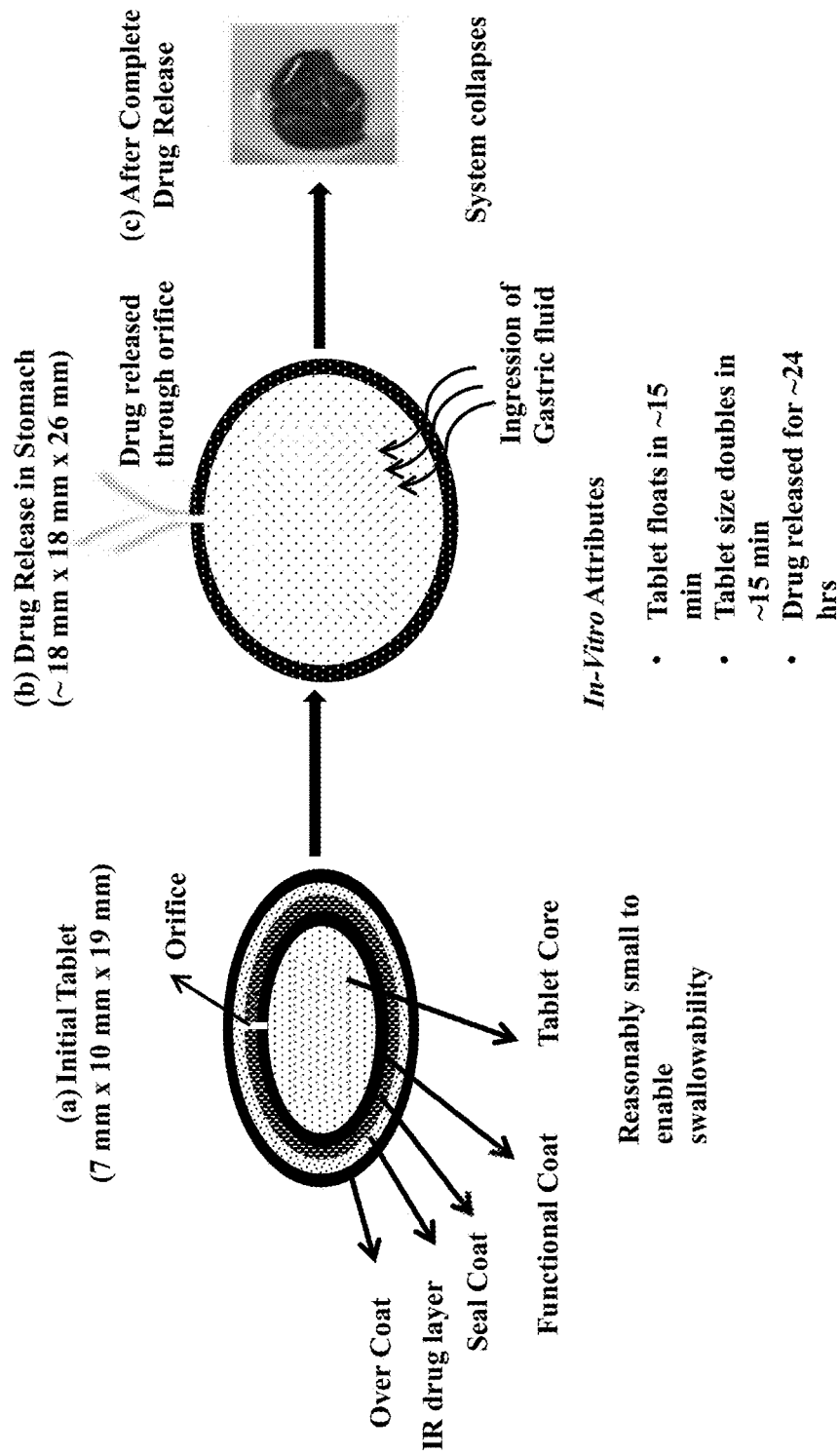

FIG. 19 provides schematic and photographic representations of the gastroretentive dosage form of the disclosure from its initial tablet form to its residue after drug release.

Figure 20:
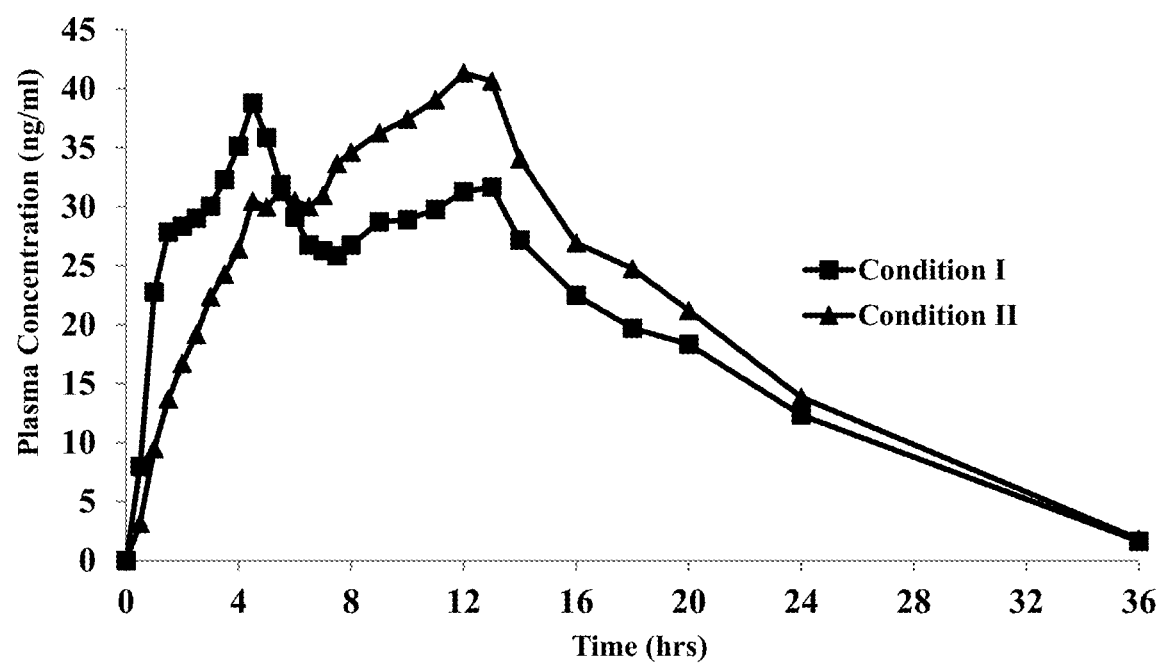

FIG. 20 compares pharmacokinetic data for gastroretentive Tablet 34, with a hole in the functional coat, under low fat-low calorie (LF-LC) breakfast conditions (Condition I) and high fat-high calorie (HF-HC) breakfast conditions (Condition II). FIG. 20 demonstrates that Tablet 34 provides a therapeutic plasma concentration of pyridostigmine for at least about 22 hours.

Figure 21:
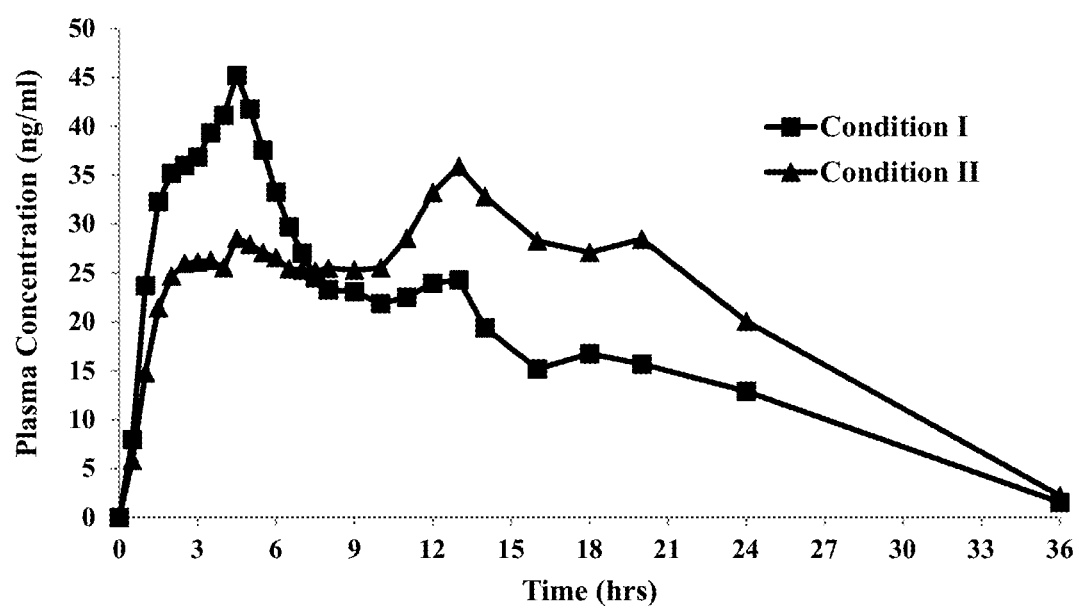

FIG. 21 compares pharmacokinetic data for gastroretentive Tablet 35, without a hole, under LF-LC breakfast conditions (Condition I) and HF-HC breakfast conditions (Condition II). FIG. 21 demonstrates that Tablet 35 provides a therapeutic plasma concentration of pyridostigmine for at least about 22 hours.

Figure 22:
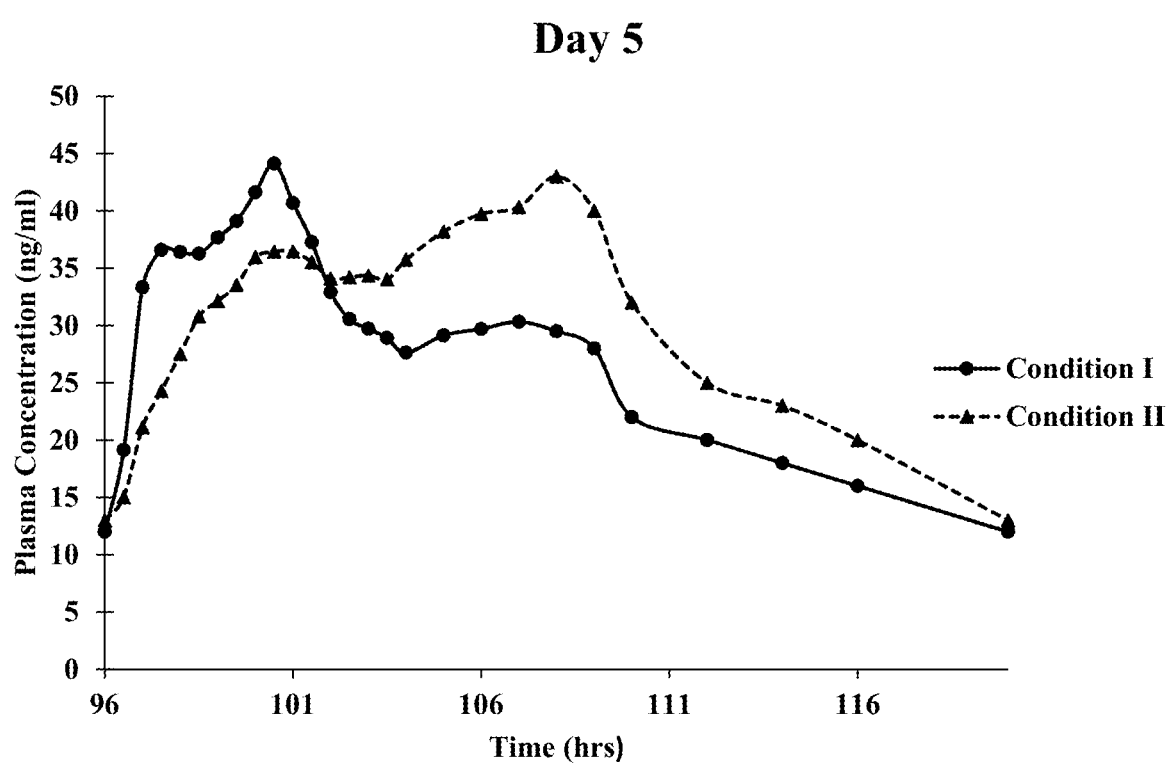

FIG. 22 provides a steady state plasma concentration of pyridostigmine bromide from Tablet 34, day 5, based on a steady state simulation for Tablet 34 over a 5-day period. FIG. 22 demonstrates that Tablet 34 can provide and maintain therapeutic plasma concentrations of pyridostigmine, e.g., about 20 ng/ml, for a period of at least about 14 hours.

Figure 23:
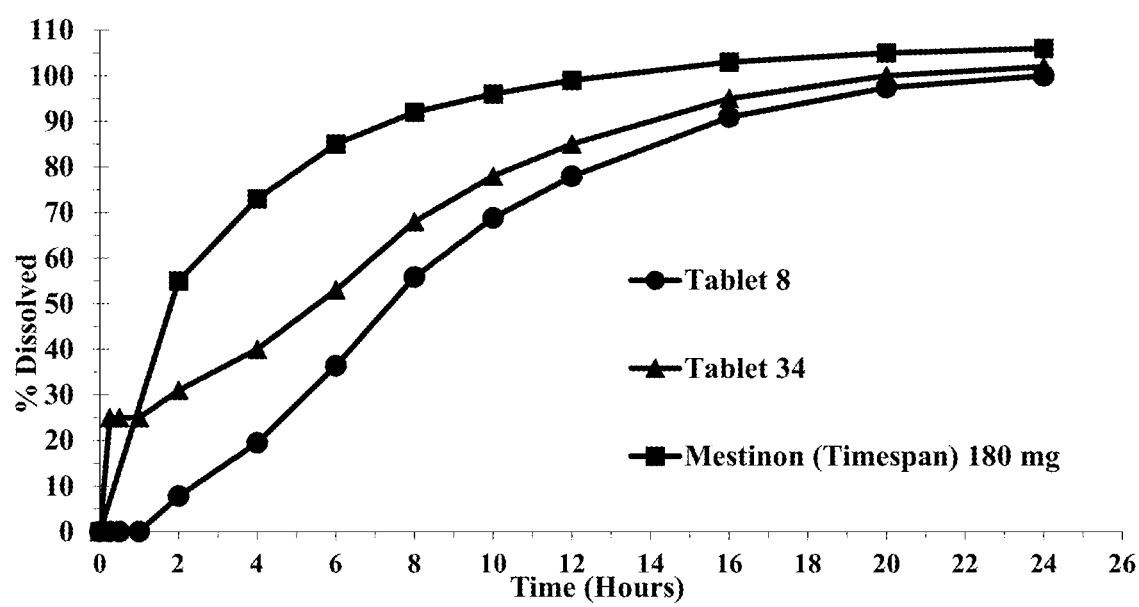

FIG. 23 compares in vitro dissolution profiles of a tablet containing an immediate release drug layer (Tablet 34), tablet with no immediate release drug layer (Tablet 8), and MESTINON® TIMESPAN, in 50 mM 900 ml of pH 4.5 acetate buffer with 100 mM NaCl, using USP Apparatus I (Custom Basket), at about 100 rpm and about 37° C. FIG. 23 demonstrates that Tablet 34 exhibits a substantial decrease in (e.g., elimination of) lag time compared to Tablet 8. FIG. 23 further demonstrates that Tablet 8 (without IR drug layer) exhibits minimized initial burst release; and Tablet 34 (with IR drug layer) provides an immediate release of a therapeutic amount of pyridostigmine bromide, with reduced initial burst release (less than about 35% drug release in about 2 hours) of the drug, compared to MESTINON® TIMESPAN.

Figure 24:
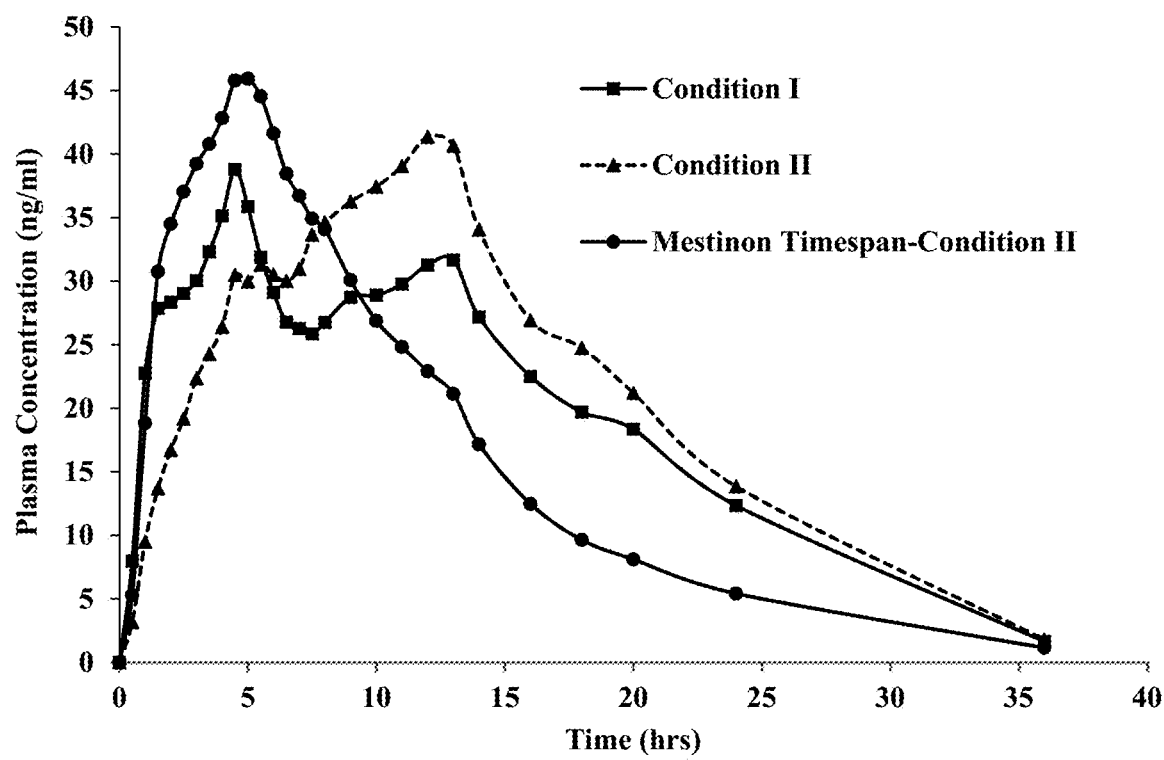

FIG. 24 compares pharmacokinetic data for gastroretentive Tablet 34, with a hole in the functional coat, under LF-LC breakfast conditions (Condition I) and HF-HC breakfast conditions (Condition II), and MESTINON® TIMESPAN, under HF-HC breakfast conditions (Condition II). FIG. 24 demonstrates that MESTINON® TIMESPAN provides higher drug plasma concentrations between about 0 and 5 hours compared to Tablet 34 under Conditions I and II. FIG. 24 further demonstrates that Tablet 34, under Conditions I and II, provides higher drug plasma concentrations over an extended time period, e.g., about 7 hours or beyond, compared to MESTINON® TIMESPAN.

Figure 25A:
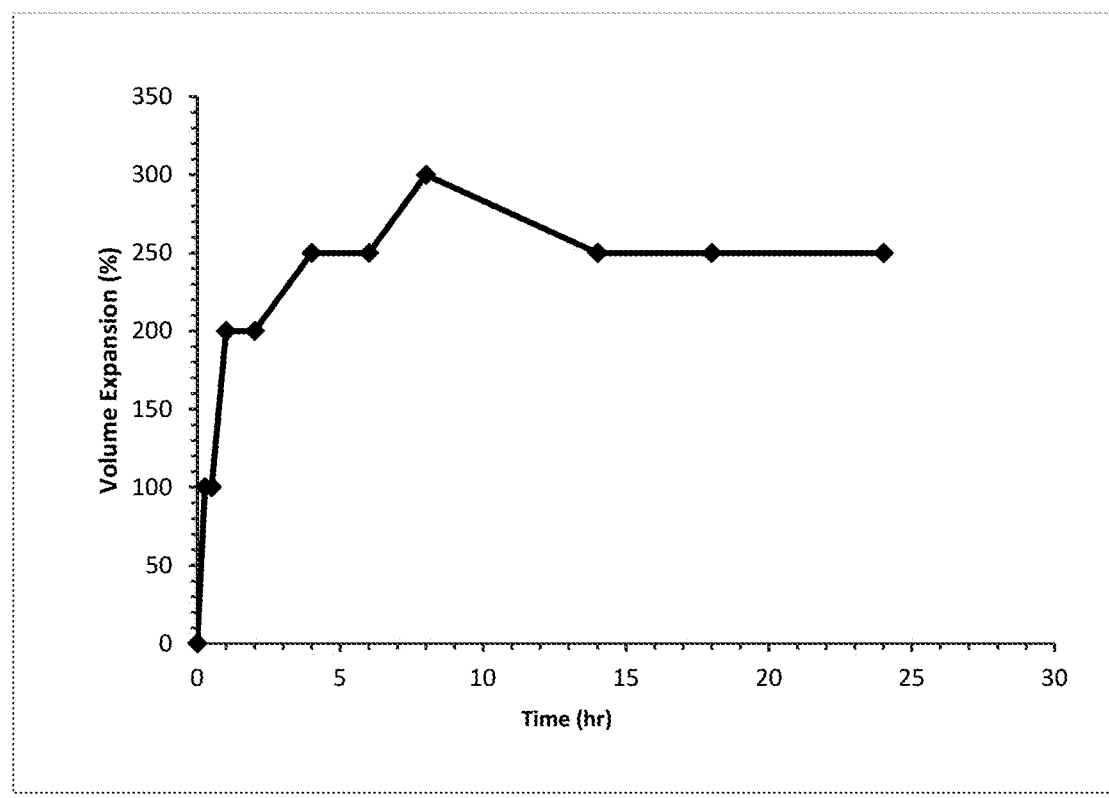

FIG. 25A provides volume expansion of Tablet 34 using Rotating Bottle method, at 5 rpm and 37° C., in 200 ml of 0.001 N HCL containing 10 mM NaCl. FIG. 25A demonstrates that the tablet exhibits 100% volume expansion at about 30 minutes, 200% volume expansion at about 1 hour, and 300% volume expansion at about 8 hours post-administration of the tablet into the dissolution medium.

Figure 25B:
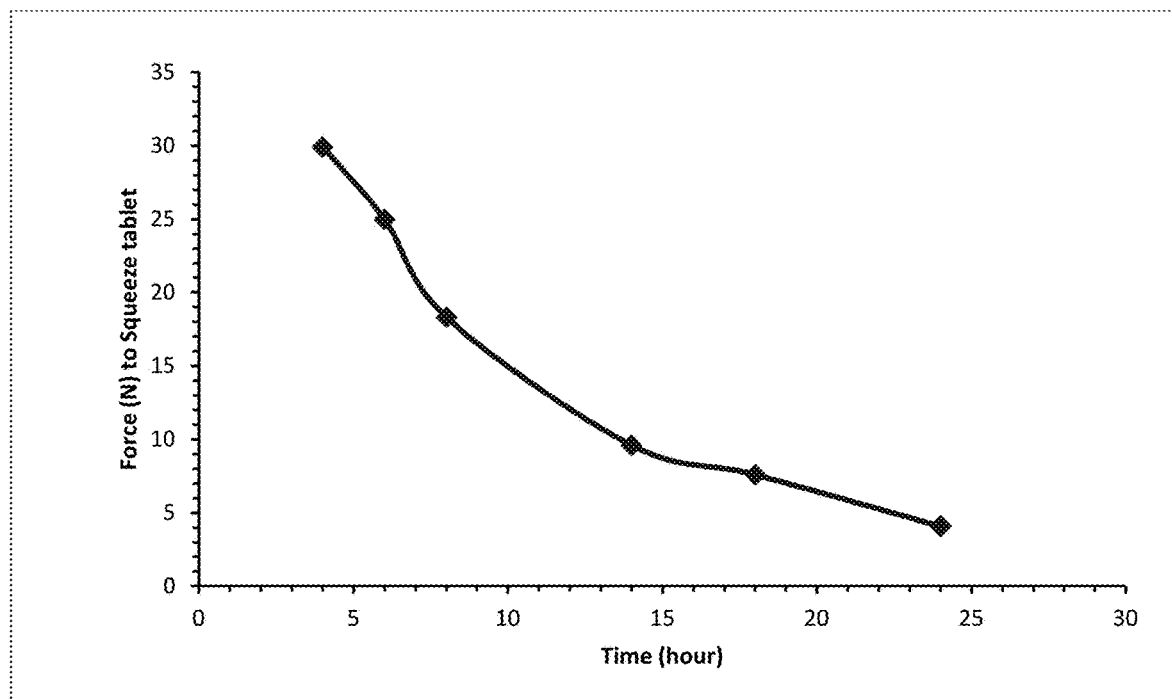

FIG. 25B provides texture/compressibility force for Tablet 34 at various time points and corresponding volume expansions (see FIG. 25A), using TA.XT$^{Plus}$ apparatus. FIG. 25B demonstrates that the compression force required to squeeze out the matrix core at 2 hours post-administration, at about 200% volume gain, was 30 N; at 8 hours post-administration, at about 300% volume gain, was 18.3 N; and at 24 hours post-administration, at about 250% volume gain, was 4.1 N.

6. DETAILED DESCRIPTION

The presently disclosed subject matter provides extended release pyridostigmine compositions suitable for once-daily administration. In certain embodiments, the composition is suitable for twice-daily administration. In certain embodiments, the compositions of the disclosure provide dual-controlled release, e.g., membrane-controlled and matrix-controlled extended release, of pyridostigmine bromide. Such dual-controlled release results in maintaining therapeutic plasma concentration, with minimized dose dumping (minimized initial burst release) of pyridostigmine bromide, and possibly overcome the gastrointestinal side effects associated with the currently marketed extended release pyridostigmine products. In certain embodiments, the lag time associated with the extended release compositions of the disclosure is eliminated with the presence of an immediate release layer containing pyridostigmine bromide. In certain embodiments, the extended release compositions containing an IR layer minimize initial burst release of the drug compared to marketed extended release pyridostigmine products. The extended release pyridostigmine compositions of the disclosure can be formulated as gastroretentive tablets, matrix tablets, and pellets suitable for dosing in capsules, tablets, sachets, and as sprinkled pellets on food. In certain embodiments, the pyridostigmine compositions can be formulated as gastroretentive tablets providing extended release of pyridostigmine bromide. In certain embodiments, the compositions of the disclosure provide extended release of pyridostigmine bromide for at least about 14 hours, at least about 16 hours, at least about 18 hours, or at least about 24 hours. In certain embodiments, the disclosure provides methods for making matrix tablets, pellets, and gastroretentive tablets comprising pyridostigmine bromide.

For clarity and not by way of limitation, this detailed description is divided into the following sections:
6.1. Definitions;
6.2. Pyridostigmine Dosage Forms;
6.3. Methods of Making; and
6.4. Methods of Treatment.

6.1. Definitions

The terminology used in the present disclosure is for the purpose of describing particular embodiments only and is not intended to be limiting. As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing," and "comprising" are interchangeable, and one of skill in the art is cognizant that these terms are open-ended terms.

As used herein, "and/or" refers to and encompasses any and all possible combinations of one or more of the associated listed items. The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 15%, up to 10%, up to 5%, up to 1%, up to 0.5%, or even up to 0.1% of a given value. Unless otherwise defined, all terms, including technical and scientific terms used in the description, have the same meaning as commonly understood by one of ordinary skill in the art to which the present disclosure belongs. As used herein, "about" will be understood by persons of ordinary skill in the art and will vary to some extent on the context in which it is used. If there are uses of the term which are not clear to person of ordinary skill in the art given the context in which it is used, "about" will mean up to about ±10% of the particular term.

As used herein, a "therapeutically effective" or "therapeutically acceptable" amount refers to an amount that will elicit a therapeutically useful response in a subject and includes an additional amount or overage of active ingredient deemed necessary in the formulation to provide the desired amount upon administration. The therapeutically useful response can provide some alleviation, mitigation, and/or decrease in at least one clinical symptom in the subject. Those skilled in the art will appreciate that the therapeutically useful response need not be complete or curative, as long as some benefit is provided to the subject. In some embodiments, the subject is a human.

As used herein, the terms "treatment," "treat," and "treating" refer to reversing, alleviating, delaying the onset of, and/or inhibiting the progress of a disease or disorder as described herein. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example to prevent or delay their recurrence.

As used herein, the term "immediate release" refers to release of at least 70% of a drug in one hour (i.e., one hour post-administration).

As used herein, the terms "extended release" and "sustained release" can be used interchangeably and refer to dosage forms or compositions that are formulated to provide therapeutic drug concentrations over an extended period of time after administration, thereby allowing a reduction in dosing frequency, as compared to a drug presented as an immediate release dosage form.

As used herein, the term "floating" is used in conjunction with a "floating gastroretentive dosage form", which has a bulk density less than gastric fluids. Such dosage forms are "floating" in that they remain buoyant in the gastric fluids of the stomach for a targeted period of time. The floating dosage form then is able to be retained in the stomach, while releasing an active agent.

As used herein, the terms "floating lag time" and "lag time" refer to the time between the addition of a dosage form to a medium and the time when the dosage form begins to float on the medium (e.g., in an in vitro setting), or the time between the consumption of a dosage form by a user and the time when the dosage form begins to float on the surface of the gastric fluid (e.g., in an in vivo setting).

As used herein, the term "gastroretentive dosage form," can be used interchangeably with the term "gastroretentive oral floating drug delivery system". These terms refer to modified release dosage forms providing delayed gastric emptying as compared to food (e.g., retention in the stomach beyond the retention of food).

The term "pyridostigmine," as used herein, refers to the pyridostigmine as well as all pharmaceutically acceptable salts, esters, and functionally equivalent chemical compounds of pyridostigmine.

The terms "initial burst release" and/or "dose dumping," as use herein, refer to an unintended initial spike in concentration of pyridostigmine in extended release dosage forms.

The terms "reduced initial burst release," and the like, as used herein, refer to in vitro release of from about 20% to about 35% of the pyridostigmine within two hours of dissolution in a dissolution medium, measured using USP Apparatus I (Custom Basket), at about 100 rpm and about 37° C.

The terms "minimized initial burst release", and the like, as used herein, refer to in vitro release of not more than 20% of the pyridostigmine within two hours of dissolution in a dissolution medium, measured using USP Apparatus I (Custom Basket), at about 100 rpm and about 37° C.

The terms "pore former" and the like, as used herein, refer to water-soluble polymers and/or water-soluble small molecules that will form pores or channels (i.e., behave as a channeling agent) in the functional coat/membrane, thereby creating a permeable functional coat/membrane. The term "pore former" includes molecules used to create a certain amount of diffusion through an insoluble (or sparingly soluble) coating of a tablet, pellet, or particle to achieve an extended release profile.

The term "simulated gastric fluid," as used herein, refers to medium that is used to mimic the chemical environment of gastric medium in vitro.

The term "gastric fluid," as used herein, refers to medium occurring in stomach of an individual.

The term "dissolution medium," as used herein, refers to a biorelevant medium mimicking gastric fluid conditions. In certain embodiments, the medium includes 50 mM of pH 4.5 acetate buffer; 50 mM of pH 4.5 acetate buffer with 100 mM NaCl; pH 5.0 buffer with 150 mM NaCl; pH 2.0 medium with 100 mM NaCl; 0.01 N HCl; or a mixture of 150 mM NaCl, 30 mM sodium acetate, and 17 mM acetic acid.

The terms "swellable," "swelling," and the like, as used herein with respect to a polymer, refer to a polymer capable of imbibing fluid and swelling when in contact with a fluid environment.

The terms "expanding," "expansion," and the like, as used herein with respect to a permeable elastic membrane, refer to stretching or distention of a membrane due to the membrane elasticity, and an outward pressure, e.g., gas pressure, on the membrane.

The term "permeable," as used herein, refers to a membrane containing sparingly soluble polymers, or insoluble polymers, with or without a pore former, that will allow particles and fluids to pass through membrane by diffusion. As used herein, the terms functional coat and permeable membrane are used interchangeably.

The terms "wicking agent," and "disintegrants," as used interchangeably herein, refer to a material(s) with the ability to draw and spread water into the core of the dosage form. Wicking agents help to increase the contact surface area of the drug with the incoming aqueous fluid, which helps to enhance the rate of drug released from the dosage form. Wicking agents carry water to surfaces inside the core of the tablet to create channels or a network of increased surface area.

The term "low viscosity hydroxypropyl methylcellulose/hypromellose," as used herein, refers to hydroxypropyl methylcellulose/hypromellose 2208 ("K" type) with a viscosity of between about 50 mPa·s and about 2,400 mPa·s, and a weight average molecular weight of between about 150,000 and about 300,000.

The term "high viscosity hydroxypropyl methylcellulose/hypromellose," as used herein, refers to hydroxypropyl methylcellulose/hypromellose 2208 ("K type) or hydroxypropyl methylcellulose/hypromellose 2910 ("E" type) with a viscosity of between about 2,500 mPa·s and about 300,000 mPa·s, and a weight average molecular weight of between about 350,000 and about 1,500,000.

The term "dual-controlled release," as used herein, refers to drug release from a membrane-controlled matrix (also referred to as a membrane-controlled matrix core or membrane-controlled core). The term "dual-controlled release" includes drug release that is controlled by both the matrix and the membrane portions of the dosage form, e.g., matrix-controlled and membrane-controlled release of pyridostigmine bromide.

6.2. Pyridostigmine Dosage Forms

The disclosed subject matter provides for extended release compositions containing pyridostigmine. The presently disclosed subject matter also provides for formulating the extended release compositions containing pyridostigmine into various dosage forms, such as, e.g., matrix tablets, gastroretentive tablets, and pellets. In certain embodiments, the present disclosure provides for dosage forms that contain an IR layer containing pyridostigmine bromide to eliminate the lag time associated with the presence of an extended release component alone. In certain embodiments, the extended release dosage forms without an immediate release layer provide minimized initial burst release, and the extended release dosage forms containing an immediate release layer provide reduced initial burst release of the drug, compared to marketed extended release pyridostigmine products. In certain embodiments, the extended release dosage forms of the present disclosure are formulated to minimize the "dose dumping" drug release (also referred to herein as "minimized initial burst release") during the first one to two hours of dissolution, compared with the currently marketed ER pyridostigmine products. Such dose dumping is believed to be responsible for unwanted GI side effects experienced with the currently marketed ER pyridostigmine products. Thus, the extended release dosage forms of the disclosure minimize the GI side effects, and provide and maintain therapeutic plasma concentrations of pyridostigmine for a period of at least about 14 hours. In certain embodiments, the extended release pyridostigmine dosage forms of the disclosure provide residual plasma levels of the drug in the morning, such that patients wake up feeling more refreshed and more functional before taking the morning dose, as compared with the currently marketed pyridostigmine products. In certain embodiments, the reduced initial drug concentration (e.g., reduced initial burst release) is sufficient to provide a therapeutic effect and avoid GI side effects. In certain embodiments, the extended release dosage forms of the disclosure either (1) contain an IR drug layer containing pyridostigmine bromide or (2) are administered with an IR pyridostigmine dosage form, in order to eliminate the lag time.

In certain embodiments, the gastroretentive dosage forms of the present disclosure provide extended release of pyridostigmine bromide for up to about 24 hours.

In certain embodiments, the gastroretentive dosage form comprising pyridostigmine bromide of the present disclosure comprises an immediate release layer and an extended release component, wherein both the immediate release layer and the extended release component contain pyridostigmine bromide, and wherein the dosage form provides an extended release, with reduced initial burst release, of pyridostigmine bromide, for at least about 14 hours.

The extended release compositions described herein comprise pyridostigmine and/or pharmaceutically acceptable salts thereof. Nonlimiting pharmaceutically acceptable salts include hydrochloride, hydrobromide, hydroiodide, bromide, sulfite, sulfate, bisulfate, nitrate, salicylate, citrate, tartrate, bitartrate, lactate, phosphate, malate, maleate, fumarate, succinate, acetate, and pamoate salts. In certain embodiments, the pharmaceutically acceptable salt is bromide.

In certain embodiments, a pyridostigmine salt is present in amounts of from about 50 mg to about 500 mg per dose, and any other range in between. In certain embodiments, a pyridostigmine salt can be present in amounts from about 60 mg to about 450 mg, 60 mg to about 400 mg, from about 60 mg to about 360 mg, from about 60 mg to about 300 mg, from about 60 mg to about 240 mg, from about 60 mg to about 180 mg, or from about 60 mg to about 120 mg per dose, and any other range in between. In certain embodiments, a pyridostigmine salt can be present in an amount of about 80 mg, about 100 mg, about 150 mg, about 200 mg, about 250 mg, about 300 mg, about 350 mg, about 400 mg, or any intermediate values therein, per dose to provide a wide range of doses depending on the disease severity. In certain embodiments, the pyridostigmine salt is present in an immediate release layer and an extended release component. In certain embodiments, the immediate release layer contains between about 0 mg and about 60 mg of a pyridostigmine salt. In certain embodiments, the immediate release layer contains about 5 mg, about 10 mg, about 15 mg, about 20 mg, about 25 mg, about 30 mg, about 35 mg, about 40 mg, about 45 mg, about 50 mg, about 55 mg, about 60 mg, or any intermediate amounts therein, of a pyridostigmine salt. In certain embodiments, the extended release component contains between about 50 mg and about 400 mg of a pyridostigmine salt. In certain embodiments, the extended release component contains about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, or any intermediate amounts therein, of a pyridostigmine salt. In certain embodiments, the compositions of the disclosure include the following amounts of a pyridostigmine salt in the IR layer/ER component, respectively: about 30 mg/about 70 mg; about 20 mg/about 160 mg; about 20 mg/about 180 mg; about 45 mg/about 155 mg; about 45 mg/about 205 mg; about 45 mg/about 255 mg; about 45 mg/about 305 mg; or about 45 mg/about 355 mg. In certain embodiments, the compositions of the disclosure include the following amounts of a pyridostigmine salt in the IR layer/ER component, respectively: about 10 mg/about 50 mg; about 15 mg/about 85 mg; about 30 mg/about 70 mg; about 37.5 mg/about 212.5 mg; or about 52.5 mg/about 297.5 mg.

In certain embodiments, the pyridostigmine salt is pyridostigmine bromide. In certain embodiments, pyridostigmine bromide is present in amounts of from about 50 mg to about 500 mg per dose, and any other range in between. In certain embodiments, pyridostigmine bromide can be present in amounts from about 60 mg to about 450 mg, 60 mg to about 400 mg, from about 60 mg to about 360 mg, from about 60 mg to about 300 mg, from about 60 mg to about 240 mg, from about 60 mg to about 180 mg, or from about 60 mg to about 120 mg per dose, and any other range in between. In certain embodiments, pyridostigmine bromide can be present in an amount of about 80 mg, about 100 mg, about 150 mg, about 200 mg, about 250 mg, about 300 mg, about 350 mg, about 400 mg, or any intermediate values therein, per dose to provide a wide range of doses depending on the disease severity. In certain embodiments, the pyridostigmine bromide is present in an immediate release layer and an extended release component. In certain embodiments, the immediate release layer contains between about 0 mg and about 60 mg of pyridostigmine bromide. In certain embodiments, the immediate release layer contains about 5 mg, about 10 mg, about 15 mg, about 20 mg, about 25 mg, about 30 mg, about 35 mg, about 40 mg, about 45 mg, about 50 mg, about 55 mg, about 60 mg, or any intermediate amounts therein, of pyridostigmine bromide. In certain embodiments, the extended release component contains between about 50 mg and about 400 mg of pyridostigmine bromide. In certain embodiments, the extended release component contains about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, or any intermediate amounts therein, of pyridostigmine bromide. In certain embodiments, the compositions of the disclosure include the following amounts of pyridostigmine bromide in the IR layer/ER component, respectively: about 30 mg/about 70 mg; about 20 mg/about 160 mg; about 20 mg/about 180 mg; about 45 mg/about 155 mg; about 45 mg/about 205 mg; about 45 mg/about 255 mg; about 45 mg/about 305 mg; or about 45 mg/about 355 mg. In certain embodiments, the compositions of the disclosure include the following amounts of pyridostigmine bromide in the IR layer/ER component, respectively: about 10 mg/about 50 mg; about 15 mg/about 85 mg; about 30 mg/about 70 mg; about 37.5 mg/about 212.5 mg; or about 52.5 mg/about 297.5 mg.

In certain embodiments, the compositions of the disclosure can be administered QD as a single dosage unit. In certain embodiments, the compositions of the disclosure can be administered QD as multiple dosage units (e.g., two, three, or four dosage units).

In certain embodiments, the present disclosure provide for a horizontally compressed, oval-shaped gastroretentive tablet dosage form containing a long axis and a short axis, wherein the long axis is between about 12 mm and about 22 mm, and the short axis is between about 8 mm and about 11 mm, and wherein the tablet, when in contact with media simulating gastric conditions, floats in about 30 minutes or less, and expands in about 60 minutes or less to a size that prevents its passage through a pyloric sphincter of a human.

In certain embodiments, the tablets maintain their GRS attributes of flotation and expansion for at least about 14 hours, at least about 16 hours, at least about 18 hours, or at least about 24 hours, or any intermediate time periods therein. In certain embodiments, the tablets in a fully expanded state can withstand compression forces of about 10 N until about 14 hours, and after about 20 hours the matrix core can be squeezed even with a compression force less than 5 N.

6.2.1. Matrix Tablets

In certain embodiments, the extended release pyridostigmine compositions of the disclosure can be formulated as a matrix tablet comprising a rate controlling matrix core coated with a rate controlling functional coat/membrane, e.g., membrane-controlled matrix.

In certain embodiments, the matrix tablet of the disclosure can comprise a rate-controlling matrix core coated with a rate-controlling functional coat/membrane, e.g., a membrane-controlled matrix core. In certain embodiments, the matrix tablet of the disclosure can comprise a rate-controlling matrix core, a seal coat over the matrix core, a functional coat/membrane over the seal coat, a second seal coat over the functional coat, an immediate release layer over the seal coat, and an over coat/aesthetic coat over the immediate release layer. In certain embodiments, the matrix tablet can exclude an immediate release layer. In particular embodiments, in the absence of an immediate release layer, the over coat is the outermost coat.

In certain embodiments, the matrix core can be made by dry granulation. In certain embodiments, the matrix core can comprise pyridostigmine bromide, and at least one water-insoluble pH-independent lipophilic material. In certain embodiments, the matrix tablets can comprise pyridostigmine bromide and at least one swellable water-soluble hydrophilic polymer. As matrix tablets can be susceptible to sticking and mottling due to the hygroscopic nature of pyridostigmine bromide, the matrix tablets of the present disclosure can include an over coat to reduce the exposure of pyridostigmine bromide to moisture. In certain embodiments, the over coat can be the outermost coat. In certain embodiments, the release rate of pyridostigmine bromide from the matrix tablets of the disclosure can be controlled by varying the amount of lipophilic material in the matrix core and the composition of the functional coat over the matrix core. In certain embodiments, the release rate of pyridostigmine bromide from the compositions of the disclosure can be controlled by adjusting the coating level of the functional coat over the matrix core. In certain embodiments, water-insoluble material in the matrix core reduces drug dissolution and provides extended release of the drug, without initial burst release, for extended periods of time. In certain embodiments, the water-insoluble material can enhance compressibility of the composition. In certain embodiments, the water-insoluble material can include, but is not limited to, ethyl acrylate and methyl methacrylate copolymer (EUIDRAGIT® NE, EUDRAGIT® NM), ammonio methacrylate copolymer (EUDRAGIT® RL 100, EUDRAGIT® RS 100, EUDRAGIT® RL PO, EUDRAGIT® RS PO), carnauba wax, stearic acid, ethylcellulose (ETHOCEL™), cellulose acetate, and silicon dioxide.

In certain embodiments, the matrix core can further comprise glidants, lubricants, compression aids, and fillers.

In certain embodiments, the disclosed matrix tablets can comprise one or more glidant materials to improve the flow of granules, and help to minimize the dosage form from weight variations. In certain embodiments, the glidants include, but are not limited to, silicon dioxide (SYLOID® 244FP), fumed silica (CAB-O-SIL®), talc, kaolin, or any combinations thereof.

In certain embodiments, the disclosed matrix tablets can comprise diluents and/or fillers. In certain embodiments, the diluents and/or fillers include, but are not limited to, lactose monohydrate USP, anhydrous lactose USP, directly compressible starches, hydrolyzed starches, pregelatinized starch, microcrystalline cellulose, silicified microcrystalline cellulose, carboxymethylcellulose and other cellulose polymers, sucrose and sucrose-based materials, dextrose, dibasic calcium phosphate anhydrous, dibasic calcium phosphate dihydrate, tricalcium phosphate, calcium sulfate dihydrate, and other alkaline inorganic salts, sugar alcohols such as mannitol (e.g., PARTECK® M200, MANNOGEM® XL), sorbitol, and xylitol, and confectioner's sugar.

In certain embodiments, diluents and/or fillers can be used as compression aids. In certain embodiments, diluents and/or fillers that can be used as compression aids include, but are not limited to, microcrystalline cellulose, silicified microcrystalline cellulose, and mannitol (e.g., PARTECK® M200, MANNOGEM® XL). In certain embodiments, the diluent and/or filler can be used in an amount of less than about 30% w/w of the tablet core. In certain embodiments, the diluent and/or filler can be present in an amount of from about 10% to about 40% w/w of the tablet. In certain embodiments, the diluent and/or filler can be present in an amount of less than about 25% w/w, less than about 24% w/w, less than about 23% w/w, less than about 22% w/w, less than about 21% w/w, less than about 20% w/w, less than about 15% w/w, less than about 10% w/w, less than about 5% w/w, or less than about 2.5% w/w of the total weight of the tablet core, or intermediate values thereof.

In certain embodiments, the matrix core can also include one or more lubricants. Lubricants are hydrophobic substances that decrease friction at the interface between a tablet's surface and the die wall during ejection and reduce wear on punches and dies. Lubricants enhance product flow by reducing interparticulate friction. In certain embodiments, the one or more lubricants can be, but are not limited to, magnesium stearate, stearic acid, calcium soaps, zinc stearate, polyoxyethylene monostearate, solid polyethylene glycols, calcium silicate, colloidal silicon dioxide, hydrogenated vegetable oils and fats, glyceryl monostearate, palmitic acid, talc, carnauba wax, mineral oil, polyethylene glycol, glyceryl palmitostearate, sodium benzoate, sodium stearyl fumarate, and any combination thereof. In certain embodiments, the lubricant is magnesium stearate. In certain embodiments, the lubricant can be present in an amount of from about 0.1% w/w to about 5% w/w based on the total weight of the matrix core. In certain embodiments, the lubricant can be present in an amount of less than about 4% w/w, less than about 3% w/w, less than about 2% w/w, less than about 1.5% w/w, less than about 1.4% w/w, less than about 1.3% w/w, less than about 1.2% w/w, less than about 1.1% w/w, or less than about 1.0% w/w based on the total weight of the matrix core.

In certain embodiments, the drug release can be controlled by a matrix-controlled membrane, e.g., a matrix core and functional coat over the matrix core. In certain embodiments, the drug release can be controlled by the functional coat/membrane. In certain embodiments, the matrix core can contain rate controlling water-insoluble material selected from a group comprising, but not limited to, ethyl acrylate and methyl methacrylate copolymer (EUDRAGIT® NE, EUDRAGIT® NM), ammonio methacrylate copolymer (EUDRAGIT® RL 100, EUDRAGIT® RS 100, EUDRAGIT® RL PO, EUDRAGIT® RS PO), carnauba wax, stearic acid, ethylcellulose (ETHOCEL™), cellulose acetate, and silicon dioxide. In certain embodiments, the matrix core can contain rate-controlling swellable water-soluble hydrophilic polymer selected from the group comprising, but not limited to, hydroxypropyl methylcellulose (BENECEL™ K4M PH DC), hydroxypropyl methylcellulose (METHOCEL K100 Premium LVCR/LVDC), a polyethylene oxide polymer, a carbomer, sodium alginate, or mixtures thereof. In certain embodiments, the swellable water-soluble hydrophilic polymer can be BENECEL™ K4M PH DC. In certain embodiments, the water-soluble hydrophilic polymer can be METHOCEL K100 Premium LVCR/LVDC. In certain embodiments, the water-soluble hydrophilic polymer can be a mixture of METHOCEL K100 Premium LVCR/LVDC and BENECEL™ K4M PH DC.

In certain embodiments, the functional coat can contain rate controlling water-insoluble material. In certain embodiments, the rate controlling polymers in the functional coat can comprise, but are not limited to, ethyl acrylate and methyl methacrylate copolymer (EUDRAGIT® NE, EUDRAGIT® NM), ammonio methacrylate copolymer (EUDRAGIT® RL 100, EUDRAGIT® RS 100, EUDRAGIT® RL 30D, EUDRAGIT® RS 30D, EUDRAGIT® RL PO, EUDRAGIT® RS PO), carnauba wax, stearic acid, ethylcellulose (ETHOCEL™), cellulose acetate, and polyvinyl acetate dispersion (KOLLICOAT® SR). In certain embodiments, the functional coat can further comprise a water-soluble pore former. In certain embodiments, the water-soluble pore former can include, but is not limited to, polyethylene glycol (PEG 400, PEG 1000, PEG 1450, PEG 3350), hydroxypropyl cellulose, polyvinyl pyrolidone (PVP), KOLLIDON® 30, KOLLICOAT® IR, mannitol, and methylcellulose (METHOCEL™ E3, METHOCEL™ E5, METHOCEL™ E6).

In certain embodiments, the matrix core and the functional coat over the matrix core can include stearic acid, ethylcellulose, cellulose acetate, and/or silicon dioxide to control the release of pyridostigmine bromide. In certain embodiments, the matrix core can be at least partially covered with the functional coat. In certain embodiments, the functional coat can completely surround the matrix core.

In certain embodiments, the matrix tablet can further include a seal coat between the matrix core and the functional coat. In certain embodiments, the seal coat can cover at least a portion of the matrix core. In certain embodiments, the seal coat can comprise a nonionic water-soluble polymer. In certain embodiments, the nonionic water-soluble polymer can be selected from the group consisting of a polyvinyl alcohol-based polymer, methyl cellulose, hydroxyethyl cellulose, hydroxypropyl cellulose, hydroxypropyl methylcellulose, and mixtures thereof.

In certain embodiments, the matrix tablet can further include an over coat. In certain embodiments, the over coat can cover at least a portion of the functional coat. In certain embodiments, the over coat can completely cover the functional coat. In certain embodiments, the over coat can comprise one or more water-soluble hydrophilic polymers selected from the group consisting of water-soluble polymer selected from a group consisting of a polyvinyl alcohol-based polymer (e.g., Opadry® II), methyl cellulose, hydroxyethyl cellulose, hydroxypropyl cellulose, hydroxypropyl methylcellulose, and mixtures thereof. In certain embodiments, the water-soluble hydrophilic polymers in the over coat can include polyvinyl alcohol and polyethylene glycol, e.g., Opadry® White.

In certain embodiments, the matrix core can be further coated with an immediate release drug layer comprising pyridostigmine bromide. In certain embodiments, the dosage form comprises a matrix core, a functional coat covering at least a portion of the matrix core, a seal coat covering at least a portion of the functional coat, an IR drug layer covering at least a portion of the seal coat, and an over coat/aesthetic coat covering at least a portion of the IR drug layer.

In certain embodiments, the matrix tablets can comprise a matrix core and a functional coat. In certain embodiments, the matrix core can comprise one or more of pyridostigmine bromide, stearic acid, carnauba wax, ethylcellulose, silicon dioxide, fumed silica, mannitol, magnesium stearate and combinations thereof. In certain embodiments, the matrix core can comprise from about 100 mg to about 250 mg, from about 150 mg to about 200 mg, or about 180 mg of pyridostigmine bromide. In certain embodiments, the matrix core can further optionally comprise from about 20 mg to about 200 mg, from about 50 mg to about 180, or about 90 mg of stearic acid. In certain embodiments, the matrix core can further optionally comprise from about 50 mg to about 200 mg, or from about 80 mg to about 160 mg of carnauba wax. In certain embodiments, the matrix core can further optionally comprise from about 50 mg to about 150 mg, or about 100 mg of ethylcellulose. In certain embodiments, the matrix core can further optionally comprise from about 20 mg to about 250 mg, from about from about 50 mg to about 200 mg, or about 180 mg of silicon dioxide. In certain embodiments, the matrix core can further optionally comprise from about 5 mg to about 40 mg, from about 10 mg to about 25 mg, or about 20 mg of fumed silica. In certain embodiments, the matrix core can further comprise from about 50 mg to about 200 mg, from about 75 mg to about 150 mg, or about 100 mg of mannitol. In certain embodiments, the matrix core can further comprise from about 1 mg to about 10 mg, from about 3 mg to about 7 mg, or about 5 mg of magnesium stearate. In certain embodiments, the matrix tablet comprises a functional coat. In certain embodiments, the functional coat can comprise one or more of cellulose acetate, polyethylene glycol, methylcellulose, and combinations thereof. In certain embodiments, the functional coat can comprise from about 10 mg to about 70 mg, from about 30 mg to about 65 mg, or from about 40 mg to about 50 mg of cellulose acetate. In certain embodiments, the functional coat can further comprise from about 1 mg to about 10 mg, from about 1.5 mg to about 7 mg, or from about 2 mg to about 5 mg of polyethylene glycol. In certain embodiments, the functional coat can further comprise from about 2 mg to about 10 mg, from about 3 mg to about 7 mg, or from about 3 mg to about 5 mg of methylcellulose.

6.2.2. Gastroretentive Tablets

In embodiments, the extended release pyridostigmine compositions can be formulated as gastroretentive tablets that provide a constant reservoir for continuous absorption of pyridostigmine in the proximal gastrointestinal tract and provide constant levels of pyridostigmine over extended periods of time. The sustained release profile with fewer fluctuations in the plasma concentration is expected to fulfill an unmet need by reducing the frequency of dosing while providing better control of symptoms and improved tolerability (e.g., decreased side effects, including unwanted GI side effects) compared to currently marketed pyridostigmine products. The gastroretentive compositions (e.g., tablets) of the disclosure are particularly suitable for long-term treatment of mild to moderate MG, and as an adjunct therapy in patients who are also receiving steroids and immunotherapy. In certain embodiments, the gastroretentive tablets of the disclosure can provide gastric retention and continuous release of pyridostigmine, without initial dose dumping of pyridostigmine, for at least about 14 hours, e.g., about 24 hours.

In certain embodiments, the gastroretentive tablets of the disclosure can comprise an expanding core and a permeable elastic membrane surrounding the core, wherein the core and the membrane together can provide controlled extended release, with minimized (e.g., eliminated) or reduced dose dumping/initial burst release, of pyridostigmine bromide for at least about 14 hours.

In certain embodiments, the gastroretentive tablets of the disclosure can comprise an immediate release layer and an extended release component. The immediate release layer can comprise pyridostigmine bromide, and the extended release component can comprise a core coated with a permeable elastic membrane. In certain embodiments, the immediate release layer can provide a drug plasma concentration that is sufficient to overcome the lag time in pyridostigmine release seen without application of an IR layer, and sufficient to provide instant therapeutic effects, with possible reduced or eliminated GI side effects, and the extended release component can provide controlled extended release of the drug for a period of at least about 14 hours.

In certain embodiments, the gastroretentive tablets of the disclosure, when in contact with simulated gastric medium, can expand in about 60 minutes or less to a size that would prevent its passage through a pyloric sphincter. In certain embodiments, the gastroretentive tablets of the disclosure can float in about 10 minutes or less, expand in about 60 minutes or less to a size that prevents passage through the pyloric sphincter, and provide extended release of pyridostigmine for at least about 14 hours, e.g., about 24 hours.

6.2.2.1 Permeable Membrane/Functional Coat

The gastroretentive compositions (e.g., tablets) of the disclosure can include a rapidly expanding membrane surrounding a hydrophilic core. In certain embodiments, the membrane can be a water-insoluble, permeable elastic membrane surrounding the core. The permeable membrane can allow the flow of gastric fluid into the composition, which initiates gas generation from gas-generating agents, and the membrane flexibility can allow for rapid expansion and immediate flotation of the composition. In certain embodiments, the membrane can comprise a plasticizer and at least one ammonium polymethacrylate copolymer.

The ammonium polymethacrylate copolymer provides permeability of the membrane and the plasticizer improves elasticity and mechanical strength of the membrane. The plasticizer can provide elasticity to the membrane, ensuring that the membrane does not rupture upon expanding and that the gastroretentive drug delivery system provides the desired characteristics for drug release, hydrodynamic balance, and mechanical strength to withstand variations in pH and shear in the stomach during fed and fasted conditions. In certain embodiments, as dissolution of the active agent in the core proceeds, the plasticizer can leach out of the membrane. In certain embodiments, leaching of the plasticizer can make the membrane brittle, such that the membrane does not remain intact and the dosage form can break into pieces by the end of drug release. Hydrophilic plasticizers suitable for the disclosure include, but are not limited to, glycerin, polyethylene glycols, polyethylene glycol monomethyl ether, propylene glycol, sorbitol sorbitan solution, and mixtures thereof. Hydrophobic plasticizers suitable for the disclosure include, but are not limited to, acetyl tributyl citrate, acetyl triethyl citrate, castor oil, diacetylated monoglycerides, dibutyl sebacate, diethyl phthalate, triacetin, tributyl citrate, triethyl citrate, gelucire 39/01, gelucire 43/01, and mixtures thereof. In certain embodiments, the plasticizers include various polyethylene glycols, glycerin, and/or triethyl citrate. In certain embodiments, the plasticizer is triethyl citrate.

In certain embodiments of the disclosure, the permeable elastic membrane can comprise two (or more) water-insoluble polymers: at least one of EUDRAGIT® RL 30D (copolymer dispersion of ethyl acrylate, methyl methacrylate, and methacrylic acid ester with quaternary ammonium groups, 1:2:0.2) and EUDRAGIT® RS 30D (copolymer dispersion of ethyl acrylate, methyl methacrylate, and methacrylic acid ester with quaternary ammonium groups, 1:2:0.1) to improve permeability; and at least one of KOLLICOAT® SR 30D (dispersion of polyvinyl acetate and polyvinyl pyrolidone), EUDRAGIT® NE 30D (copolymer dispersion of ethyl acrylate, methyl methacrylate), and EUDRAGIT® NM 30D (copolymer dispersion of ethyl acrylate, methyl methacrylate), to improve mechanical strength (tensile strength). The membrane can further include hydrophilic polymer and, optionally, water-soluble nonionic polymer that act as a pore former, to modify its elasticity, permeability, and tensile strength.

In certain embodiments, the permeable elastic membrane can provide desired characteristics for drug release and tensile strength to withstand peristalsis and mechanical contractility of the stomach (shear). The combination of a water-soluble hydrophilic polymer in the core, and the unique permeable elastic membrane formed over the tablet core by the coating of a homogeneous dispersion of at least one of EUDRAGIT® RL 30D and EUDRAGIT® RS 30D (collectively "dispersions of ammonium salts of polymethacrylate copolymers") to improve permeability, and at least one of KOLLICOAT® SR 30D, EUDRAGIT® NE 30D, and EUDRAGIT® NM 30D (collectively "neutral polymethacrylate copolymer dispersions") to improve mechanical strength (tensile strength), can provide the desired extended drug release while maintaining the integrity of the core in an expanded state, thus extending the gastric residence time and preventing the dosage form from being emptied from the stomach until substantial or complete release of the drug, usually after a prolonged period.

In certain embodiments, the water-insoluble polymers in the permeable elastic membrane can comprise at least one of EUDRAGIT® RL PO and/or EUDRAGIT® RS PO (i.e., ammonium polymethacrylate copolymers in powder form). In certain embodiments, the permeable elastic membrane can be formed over the core by coating the core with a solution of EUDRAGIT® RL PO (copolymer of ethyl acrylate, methyl methacrylate, and trimethylammonioethyl methacrylate chloride (1:2:0.2) with a glass transition temperature ($T_g$) of 63) and/or EUDRAGIT® RS PO (copolymer of ethyl acrylate, methyl methacrylate, and trimethylammonioethyl methacrylate chloride (1:2:0.1) with a glass transition temperature ($T_g$) of 65), a plasticizer, and talc.

In certain embodiments, the membrane can include a water-insoluble polymer, a plasticizer, and at least one pore former comprising a water-soluble nonionic polymer. In certain embodiments, the pore formers and plasticizers can modify membrane elasticity, permeability, and tensile strength. In certain embodiments, the membrane can exclude any pore former. In certain embodiments, examples of insoluble permeable components of the permeable elastic membrane include, but are not limited to, copolymers of ethyl acrylate, methyl methacrylate, and trimethylammonioethyl methacrylate chlorides (e.g., EUDRAGIT® RL 30D or EUDRAGIT® RS 30D, EUDRAGIT® RS PO, EUDRAGIT® RL PO); cellulose acetate phthalate; ethyl cellulose; and hypromellose acetate succinate.

In certain embodiments, examples of insoluble components of the permeable elastic membrane that provide elasticity to the membrane include, but are not limited to, copolymers of ethyl acrylate and methyl methacrylate (e.g., EUDRAGIT® NE 30D, EUDRAGIT® NM 30D), polyvinyl acetates (e.g., KOLLICOAT® SR 30D), thermoplastic polyurethanes, ethylene-vinyl acetate, and polydimethyl siloxane.

In certain embodiments, the permeable elastic membrane can be a coating of a solution of EUDRAGIT® RL PO and/or EUDRAGIT® RS PO. In certain embodiments, the core can be coated with a solution of EUDRAGIT® RL PO and/or EUDRAGIT® RS PO in acetone and water mixture.

In certain embodiments, the coating dispersion can include at least one of EUDRAGIT® RL PO and EUDRAGIT® RS PO (collectively "solutions of ammonium polymethacrylate copolymer") to improve permeability, and at least one plasticizer to improve mechanical strength (tensile strength). In certain embodiments, powder forms of EUDRAGIT®, e.g., EUDRAGIT® RL PO and EUDRAGIT® RS PO, are preferred over EUDRAGIT® dispersions, e.g., EUDRAGIT® RS 30D and EUDRAGIT® RL 30D.

In certain embodiments, the permeability of the permeable elastic membrane can be adjusted to provide a floating lag time of less than about 10 minutes and floating time of about 1 hour to about 24 hours. In certain embodiments, the gastroretentive pyridostigmine tablets of the disclosure can comprise a membrane containing ammonium polymethacrylate copolymer, e.g., EUDRAGIT® RL PO or EUDRAGIT® RS PO, and can exhibit a floating lag time of about 30 minutes or less and floating time of about 1 hour to about 24 hours. In certain embodiments, the ammonium polymethacrylate copolymer can be present in an amount of between about 70% and about 95% w/w of the membrane composition to provide desired permeability of the membrane. In certain embodiments, plasticizer can be present in an amount of between about 5 wt % and about 25 wt %, between about 10 wt % and about 20 wt %, between about 10 wt % and about 15 wt %, and any intermediate ranges there in, of the membrane composition to provide desired tensile strength, and elasticity for rapid expansion of the membrane. In certain embodiments, the plasticizer is present in an amount of at least about 10 wt %, at least about 11 wt %, at least about 12 wt %, at least about 13 wt %, at least about 14 wt %, at least about 15 wt %, at least about 16 wt %, at least about 17 wt %, at least about 18 wt %, at least about 19 wt %, at least about 20 wt %, at least about 21 wt %, at least about 22 wt %, at least about 23 wt %, at least about 24 wt %, and at least about 25 wt % of the membrane composition.

In certain embodiments, the membrane can further include an anti-tacking agent selected from the group consisting of talc, colloidal silicon dioxide, magnesium trisilicate, powdered cellulose, starch, and tribasic calcium phosphate. In certain embodiments, the anti-tacking agent can be colloidal silicon dioxide and/or talc. In certain embodiments, the anti-tacking agent can be present in an amount of about 5 wt % to about 30 wt % of the membrane composition. In certain embodiments, the anti-tacking agent is present in an amount of about 5 wt %, about 10 wt %, about 15 wt %, about 20 wt %, about 25 wt %, about 30 wt %, or any intermediate values therein, by weight of the membrane composition.

In certain embodiments, the membrane can expand the dosage form in about 30 minutes to a size that prevents its passage through the pyloric sphincter, and the hydrophilic core, surrounded by the membrane, can swell with imbibition and absorption of fluid and assist the membrane in providing an extended release of the drug. In certain embodiments, the membrane can be highly elastic and flexible due to the presence of at least one plasticizer and/or a copolymer of ethyl acrylate and methyl methacrylate, and can expand rapidly with an outward pressure on the membrane from the generated $CO_2$ gas.

In certain embodiments, the membrane can provide an extended release of the drug for at least about fourteen hours, e.g., about twenty-four hours.

6.2.2.2 Core

In certain embodiments, the core can comprise pyridostigmine or a pharmaceutically acceptable salt thereof (e.g., pyridostigmine bromide), an acid, a gas-generating agent, a disintegrant/wicking agent, and at least one swellable water-soluble hydrophilic polymer.

In certain embodiments, the swellable water-soluble hydrophilic polymer in the core can comprise a high viscosity hydroxypropyl methylcellulose/hypromellose with a viscosity of between about 2,500 mPa·s and about 300,000 mPa·s, and a weight average molecular weight of between about 350,000 and about 1,500,000 (e.g., BENECEL™ K4M PH DC with a viscosity of between about 2,700 mPa·s and 5,040 mPa·s); a low viscosity hydroxypropyl methylcellulose/hypromellose with a viscosity of between about 50 mPa·s and about 2,400 mPa·s, and a weight average molecular weight of between about 150,000 and about 300,000 (e.g., METHOCEL K100 Premium LVCR/LVDC with a viscosity of between about 80 mPa·s and 120 mPa·s), a polyethylene oxide polymer, a carbomer, sodium alginate, or mixtures thereof. In certain embodiments, the water-soluble hydrophilic polymer can be hypromellose 2208 with a viscosity of between about 2,700 mPa·s and 5,040 mPa·s (BENECEL™ K4M PH DC). In certain embodiments, the swellable water-soluble hydrophilic polymer can be hypromellose 2208 with a viscosity of between about 80 mPa·s and 120 mPa·s (METHOCEL K100 Premium LVCR/LVDC). In certain embodiments, the swellable water-soluble hydrophilic polymer can be a mixture of two or more hypromelloses with different viscosities, e.g., METHOCEL K100 Premium LVCR/LVDC and BENECEL™ K4M PH DC. In certain embodiments, the low viscosity hypromellose has a viscosity of between about 80 mPa·s and about 120 mPa·s, between about 200 mPa·s and about 300 mPa·s, between about 562 mPa·s and about 1050 mPa·s, or between about 1,125 mPa·s and about 2,100 mPa·s. In certain embodiments, the low viscosity hypromellose has a weight average molecular weight of about 164,000, about 200,000, about 250,000, or about 300,000. In certain embodiments, the high viscosity hypromellose has a viscosity of between about 2,700 mPa·s and about 5,040 mPa·s, between about 13,500 mPa·s and about 25,200 mPa·s, between about 26,250 mPa·s and about 49,000 mPa·s, between about 75,000 mPa·s and about 140,000 mPa·s, or between about 150,000 mPa·s and about 280,000 mPa·s. In certain embodiments, the high viscosity hypromellose has a weight average molecular weight of about 400,000, about 575,000, about 675,000, about 1,000,000, or about 1,200,000. In certain embodiments, the water-soluble hydrophilic polymer is present in an amount of between about 5 wt % and about 35 wt %, based on the total weight of the core. In certain embodiments, the hypromellose 2208, with a viscosity of between about 2,700 mPa·s and about 5,040 mPa·s, is present in an amount of between about 5 wt % and about 35 wt %, based on the total weight of the core. In certain embodiments, the hypromellose 2208, with a viscosity of between about 2,700 mPa·s and about 5,040 mPa·s, is present in an amount of about 5 wt %, about 10 wt %, about 15 wt %, about 20 wt %, about 25 wt %, about 30 wt %, or about 35 wt %, based on the total weight of the core. In certain embodiments, dosage forms comprising hypromellose 2208, with a viscosity of between about 2,700 mPa·s and about 5,040 mPa·s, present in an amount of about 30 wt %, based on the total weight of the core, provide extended release of pyridostigmine bromide for at least about 14 hours. In certain embodiments, the dosage form comprises a low viscosity hypromellose 2208 with a viscosity of between about 80 mPa·s and about 120 mPa·s (e.g., METHOCEL K100 Premium LVCR/LVDC). In certain embodiments, METHOCEL K100 Premium LVCR/LVDC is present in an amount of about 5 wt %, about 10 wt %, about 15 wt %, about 20 wt %, about 25 wt %, about 30 wt %, or about 35 wt %, based on the total weight of the core. In certain embodiments, the mixture of METHOCEL K100 Premium LVCR/LVDC and BENECEL™ K4M PH DC in the dosage form provides extended release of pyridostigmine bromide for about 14 hours or more. In certain embodiments, the presence of hypromellose 2208 in an amount of between about 20% w/w and about 35% w/w of the core, helps in providing extended release of the drug for at least about 14 hours. In certain embodiments, the presence of METHOCEL K100 Premium LVCR/LVDC in the mixture of two or more hypromellose 2208 aids in the complete emptying of the dosage form at the end of the drug release period.

In certain embodiments, the core comprises gas-generating agents that can generate $CO_2$ on interaction with acid. Examples of gas-generating agents that can be used in the compositions of the present disclosure include, but are not limited to, all organic and inorganic strong and weak bases, e.g., carbonate and bicarbonate salts of alkali and alkaline earth metals, that can interact with stomach acid for in situ gas generation. In certain embodiments, the gas-generating agent can be sodium bicarbonate, sodium carbonate, magnesium carbonate, and/or calcium carbonate. In certain embodiments, a mixture of calcium carbonate and sodium bicarbonate can provide desired sustained release of $CO_2$. In certain embodiments, the gas-generating agent can be present in an amount of at about 5 wt % to about 50 wt % of core. In certain embodiments, the gas-generating agent can be present in an amount of about 5 wt %, about 10 wt %, about 15 wt %, about 20 wt %, about 25 wt %, about 30 wt %, about 35 wt %, about 40 wt %, about 45 wt %, about 50 wt %, or any intermediate values therein, based on the total weight of the core.

In certain embodiments, the core can comprise an acid to achieve rapid floating and expansion of the tablet, regardless of the gastric pH. In certain embodiments, the acids include, but are not limited to, succinic acid, citric acid, acetic acid, malic acid, fumaric acid, stearic acid, tartaric acid, boric acid, benzoic acid, or mixtures thereof. In certain embodiments, the acid can be succinic acid. In certain embodiments, the acid can be present in an amount of between 0 wt % and about 20 wt % of the core. In certain embodiments, the acid can be present in an amount of about 0.5 wt %, about 1 wt %, about 2 wt %, about 3 wt %, about 4 wt %, about 5 wt %, about 6 wt %, about 7 wt %, about 8 wt %, about 9 wt %, about 10 wt %, about 12.5 wt %, about 15 wt %, about 20 wt %, or any intermediate values therein, based on the total weight of the core.

In certain embodiments, the acid is succinic acid and the gas-generating agent is a mixture of sodium bicarbonate and calcium carbonate. In certain embodiments, the gastroretentive dosage forms of the disclosure include equimolar amounts of acid and each of sodium bicarbonate and calcium carbonate (e.g., equimolar amounts of succinic acid and sodium bicarbonate, and equimolar amounts of succinic acid and calcium carbonate).

In certain embodiments, the core can comprise a wicking agent/disintegrant selected from a group comprising, but not limited to, croscarmellose sodium; sodium starch glycolate; low-substituted hydroxypropyl cellulose; a mixture of 90% mannitol, 5% crospovidone, and 5% polyvinyl acetate (LUDIFLASH®); a coprocessed blend of mannitol, starch, crospovidone, croscarmellose sodium, colloidal silica, and silica (PHARMABURST®); microcrystalline cellulose; alginic acid; and mixtures thereof. In certain embodiments, the wicking agent can be crospovidone. In certain embodiments, the wicking agent is present in an amount of about 5 wt % to about 25 wt % of the core. In certain embodiments, the wicking agent is present in amount of about 5 wt %, about 10 wt %, about 15 wt %, about 20 wt %, about 25 wt %, or any intermediate values therein, based on the total weight of the core.

In certain embodiments, the core can further include at least one lubricant selected from the group comprising magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combinations thereof. In certain embodiments, the lubricant is magnesium stearate. In certain embodiments, the lubricant can be present in an amount of about 0.1 wt % to about 2 wt % of the core. In certain embodiments, the lubricant can be present in an amount of about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, or any intermediate values therein, based on the total weight of the core.

In certain embodiments, the core can include at least one glidant selected from the group comprising talc, colloidal silicon dioxide, magnesium trisilicate, powdered cellulose, starch, and tribasic calcium phosphate. In certain embodiments, the glidant can be colloidal silicon dioxide. In certain embodiments, the glidant can be present in an amount of about 0.1 wt % to about 2 wt % based on the total weight of the core. In certain embodiments, the glidant can be present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.5 wt %, about 2 wt %, or any intermediate values therein, based on the total weight of the core.

In certain embodiments, the core can further comprise a filler/compression aid. In certain embodiments, mannitol can be used as a filler/compression aid. In certain embodiments, mannitol can be used as an osmotic agent. In certain embodiments, mannitol can be present in an amount of about 1 wt % to about 40 wt % based on the total weight of the core.

In certain embodiments, the core can further comprise at least one color pigment. In certain embodiments, the core can include at least one pigment comprising iron oxide or lake-based colors. In certain embodiments, the pigment can be a lake-based color. In certain embodiments, the pigment can be an iron oxide pigment, e.g., oxide pigment black or Red blend. In certain embodiments, the pigment can be present in an amount of about 0.5 wt % to about 2 wt % based on the total weight of the core.

6.2.2.3 Immediate Release Drug Layer

In certain embodiments, the gastroretentive pyridostigmine compositions (e.g., tablets) of the disclosure can include an immediate release layer and an extended release component to provide a biphasic release of pyridostigmine or a pharmaceutically acceptable salt thereof. In certain embodiments, the immediate release layer can cover at least a portion of the functional coat/permeable membrane. In certain embodiments, the immediate release layer can comprise pyridostigmine or a pharmaceutically acceptable salt thereof and a binder.

In certain embodiments, the binder(s) can be selected from the group consisting of, but not limited to, povidone K 90, hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide (e.g., POLYOX®), polyethylene glycol, alginates, and pegylated polyvinyl alcohol. In certain embodiments, the binder can be hydroxypropyl cellulose. In certain embodiments, the binders can be present in an amount of about 0.5 wt % to about 30 wt % of the amount of drug in the immediate release drug layer. In certain embodiments, the binders can be present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, about 15 wt %, about 20 wt %, about 25 wt %, about 30 wt %, or any intermediates values therein, of the amount of drug in the immediate release drug layer.

6.2.2.4 Additional Coats

In certain embodiments, the gastroretentive tablets of the disclosure further can include a seal coat between the core and the permeable elastic membrane and/or between the permeable elastic membrane and the immediate release drug layer. In certain embodiments, the seal coat can cover at least a portion of the membrane. In certain embodiments, the seal coat can comprise one or more water-soluble hydrophilic polymers selected from the group consisting of a polyvinyl alcohol-based polymer (OPADRY® white, OPADRY® clear), methyl cellulose, hydroxyethyl cellulose, hydroxypropyl cellulose, hydroxypropyl methylcellulose, and mixtures thereof. In certain embodiments, the seal coat can comprise hydroxypropyl cellulose. In certain embodiments, the seal coat can be present in an amount of about 0.5 wt % to about 5 wt % of the uncoated core, membrane-coated core, or core with drug layer. In certain embodiments, the seal coat can be present in an amount of about 0.5 wt %, about 1 wt %, about 1.5 wt %, about 2 wt %, about 2.5 wt %, about 3 wt %, about 3.5 wt %, about 4 wt %, about 4.5 wt %, about 5 wt %, or any intermediate values therein, of the uncoated core, membrane-coated core, or core with drug layer.

In certain embodiments, the gastroretentive tablets of the disclosure further includes an over coat/aesthetic coat. In certain embodiments, the over coat covers at least a portion of the permeable elastic membrane (in a composition without an IR drug layer) or a portion of drug layer (in a composition with an IR drug layer). In certain embodiments, the over coat can completely cover the permeable elastic membrane or the IR drug layer. In certain embodiments, the over coat can be the outermost coat. In certain embodiments, the over coat can comprise one or more water-soluble hydrophilic polymers selected from the group consisting of methylcellulose, hydroxymethyl cellulose, hydroxypropyl cellulose, hydroxypropyl methylcellulose, and polyvinyl alcohol-based OPADRY® white.

In certain embodiments, the gastroretentive tablets of the disclosure can include at least one laser-drilled orifice/hole that passes through the permeable elastic membrane/functional coat and seal coat. In certain embodiments, the gastroretentive dosage forms of the disclosure include multiple laser-drilled orifices/holes. In certain embodiments, the gastroretentive dosage forms of the disclosure do not include laser-drilled holes in the IR drug layer and the over coat (i.e., laser-drilled holes do not pass through these layers).

6.2.2.5 Compositions

In certain embodiments, the present disclosure provide for a gastroretentive dosage form comprising an immediate release layer containing pyridostigmine bromide, and an extended release component, wherein the extended release component comprises a core comprising pyridostigmine bromide, an acid, a gas-generating agent, and a water-soluble hydrophilic polymer that swells via imbibition of gastric fluid, and a permeable elastic membrane surrounding the core and comprising a plasticizer, and a copolymer based on ethyl acrylate, methyl methacrylate, and trimethylammonioethyl methacrylate chloride, and wherein the dosage form provides an extended release, with reduced initial burst release, of pyridostigmine bromide, for at least about 14 hours. In certain embodiments, the core of the dosage form of the present disclosure includes a wicking agent selected from the group consisting of crospovidone; croscarmellose sodium; sodium starch glycolate; low-substituted hydroxypropyl cellulose; a mixture of mannitol, crospovidone, and polyvinyl acetate; a coprocessed blend of mannitol, starch, crospovidone, croscarmellose sodium, colloidal silica, and silica; microcrystalline cellulose; alginic acid; and mixtures thereof. In certain other embodiments, the core of the dosage form comprises crospovidone as a wicking agent. In certain embodiments, the dosage form of the present disclosure comprises a water-soluble hydrophilic polymer selected from the group consisting of hydroxypropyl methylcellulose, hydroxypropyl cellulose, methyl cellulose, a polyethylene oxide polymer, a carbomer, sodium alginate, and mixtures thereof. In particular embodiments, the water-soluble hydrophilic polymer is hydroxypropyl methylcellulose. In certain other embodiments, the water-soluble hydrophilic polymer is methyl cellulose. In certain other embodiments, the water-soluble hydrophilic polymer is a mixture of hydroxypropyl methylcellulose with an average molecular weight of greater than or equal to 164,000 and less than 400,000, and hydroxypropyl methylcellulose with an average molecular weight of between about 400,000 and about 1,200,000. In certain embodiments, the dosage form of the present disclosure comprises a gas-generating agent selected from the group consisting of $NaHCO_3$, $CaCO_3$, and a mixture thereof. In certain embodiments, the gas-generating agent is a mixture of $NaHCO_3$ and $CaCO_3$. In certain embodiments, the dosage form of the present disclosure comprises a plasticizer selected from the group consisting of triethyl citrate, triacetin, polyethylene glycol, propylene glycol, dibutyl sebacate, and mixtures thereof. In particular embodiments, the plasticizer is triethyl citrate. In certain embodiments, the permeable elastic membrane of the dosage form of the present disclosure is at least partially covered by the immediate release drug layer. In certain embodiments, the present disclosure provides for a dosage form that further includes a seal coat between the immediate release drug layer and the permeable elastic membrane. In certain embodiments, the seal coat of the dosage form or the present disclosure comprises a water-soluble polymer selected from the group consisting of a polyvinyl alcohol-based polymer, methyl cellulose, hydroxyethyl cellulose, hydroxypropyl cellulose, hydroxypropyl methylcellulose, or a mixture thereof. In certain embodiments, the dosage form of the present disclosure further includes an over coat over the immediate release drug layer. In particular embodiments, the over coat comprises a water-soluble polymer selected from a group consisting of a polyvinyl alcohol-based polymer, methyl cellulose, hydroxyethyl cellulose, hydroxypropyl cellulose, hydroxypropyl methylcellulose, or a mixture thereof.

In certain embodiments, the present disclosure provides for an extended release gastroretentive pyridostigmine tablet comprising an immediate release layer containing pyridostigmine bromide, and an extended release component, wherein the extended release component comprises a core comprising pyridostigmine bromide, an acid, a gas-generating agent, and a water-soluble hydrophilic polymer that swells via imbibition of gastric fluid; and a permeable elastic membrane, surrounding the core, comprising a plasticizer, and a copolymer based on ethyl acrylate, methyl methacrylate, and trimethylammonioethyl methacrylate chloride, and wherein the tablet is suitable for once daily administration and is administered as a single tablet/day. In certain embodiments, the tablet of present disclosure comprises 100 mg, 200 mg, 250 mg, 300 mg, or 350 mg of pyridostigmine bromide.

In certain embodiments, the water-soluble hydrophilic polymer of the tablet of the present disclosure is selected from the group consisting of hydroxypropyl methylcellulose, hydroxypropyl cellulose, methyl cellulose, a polyethylene oxide polymer, a carbomer, sodium alginate, and mixtures thereof. In certain embodiments, the gas-generating agent of the tablet of the present disclosure comprises $NaHCO_3$, $CaCO_3$, or a mixture thereof. In certain embodiments, the plasticizer of the tablet of the present disclosure is selected from the group consisting of triethyl citrate, triacetin, polyethylene glycol, propylene glycol, dibutyl sebacate, and mixtures thereof. In certain embodiments, the tablet of the present disclosure further includes a wicking agent selected from the group consisting of crospovidone; croscarmellose sodium; sodium starch glycolate; low-substituted hydroxypropyl cellulose; a mixture of mannitol, crospovidone, and polyvinyl acetate; a coprocessed blend of mannitol, starch, crospovidone, croscarmellose sodium, colloidal silica, and silica; microcrystalline cellulose; alginic acid; and mixtures thereof. In certain embodiments, the permeable elastic membrane of the tablet of the present disclosure is at least partially covered by the immediate release drug layer. In certain embodiments, the tablet of the present disclosure further includes a seal coat between the immediate release drug layer and the permeable elastic membrane. In certain embodiments, the seal coat of the tablet of the present disclosure comprises a water soluble polymer selected from the group consisting of a polyvinyl alcohol-based polymer, methyl cellulose, hydroxyethyl cellulose, hydroxypropyl cellulose, hydroxypropyl methylcellulose, or a mixture thereof. In certain embodiments, the present disclosure provides for a tablet that further includes an over coat over the immediate release drug layer. In certain embodiments, the overcoat of the tablets of the present disclosure comprises a water-soluble polymer selected from a group consisting of a polyvinyl alcohol-based polymer, methyl cellulose, hydroxyethyl cellulose, hydroxypropyl cellulose, hydroxypropyl methylcellulose, and mixtures thereof.

In certain embodiments, the pyridostigmine bromide gastroretentive tablets can comprise a core, a functional coat, and an overcoat. In certain embodiment, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, methylcellulose, fumed silica, magnesium stearate, and combinations thereof.

In certain embodiments, the core of the pyridostigmine bromide gastroretentive tablets can comprise from about 100 mg to about 250 mg, from about 150 mg to about 200 mg, or about 180 mg of pyridostigmine bromide. In certain embodiments, the core can further comprise from about 20 mg to about 100 mg, from about 40 mg to about 80 mg, or from about 50 mg to about 60 mg of succinic acid. In certain embodiments, the core can further comprise from about 20 mg to about 80 mg, from about 30 mg to about 65 mg, or from about 45 mg to about 55 mg of sodium bicarbonate. In certain embodiments, the core can further comprise from about 40 mg to about 200 mg, from about 50 mg to about 150 mg, or from about 60 mg to about 130 mg of calcium carbonate. In certain embodiments, the core can further comprise from about 50 mg to about 200 mg, or about 100 mg of crospovidone. In certain embodiments, the core can further comprise from about 100 mg to about 300 mg, from about 150 mg to about 250 mg, or about 230 mg of mannitol. In certain embodiments, the core can further optionally comprise from about 50 mg to about 350 mg, from about 100 mg to about 300 mg, or about 200 mg of hydroxypropyl methylcellulose with an average molecular weight of about 400,000. In certain embodiments, the core can further optionally comprise from about 150 mg to about 350 mg, or from about 200 mg to about 300 mg of hydroxypropyl methylcellulose with an average molecular weight of about 164,000. In certain embodiments, the core can further comprise from about 1 mg to about 10 mg, from about 2 mg to about 7 mg, or about 4 mg of fumed silica. In certain embodiments, the core can further comprise from about 1 mg to about 15 mg, from about 5 mg to about 10 mg, or about 8 mg of magnesium stearate. In certain embodiments, the pyridostigmine bromide gastroretentive tablets can further comprise a seal coat. In certain embodiments, the seal coat can comprise one or more of triethyl citrate, talc, hydroxypropyl cellulose, and combinations thereof. In certain embodiments, the pyridostigmine bromide gastroretentive tablets can further comprise a functional coat over the seal coat. In certain embodiments, the functional coat of the pyridostigmine bromide gastroretentive tablets can comprise from about 100 mg to about 200 mg, from about 125 mg to about 175 mg, or from about 145 mg to about 150 mg of ammonio methacrylate copolymer. In certain embodiments, the functional coat of the pyridostigmine bromide gastroretentive tablets can further comprise from about 10 mg to about 50 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 20 mg to about 40 mg, or from about 25 mg to about 35 mg of talc. In certain embodiments, the pyridostigmine bromide gastroretentive tablets can comprise an over coat. In certain embodiments, the over coat can comprise from about 5 mg to about 30 mg, from about 10 mg to about 20 mg, or about 15 mg of polyvinyl alcohol-based polymer.

In certain embodiments, the pyridostigmine bromide gastroretentive tablets can comprise a core, and a functional coat. In certain embodiment, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, methylcellulose, fumed silica, magnesium stearate, and combinations thereof. In certain embodiments, the core of the pyridostigmine bromide gastroretentive tablets can comprise from about 50 mg to about 200 mg, from about 100 mg to about 150 mg, or about 135 mg of pyridostigmine bromide. In certain embodiments, the core can further comprise from about 40 mg to about 150 mg, from about 60 mg to about 100 mg, or from about 75 mg to about 85 mg of succinic acid. In certain embodiments, the core can further comprise from about 20 mg to about 80 mg, from about 30 mg to about 65 mg, or from about 45 mg to about 55 mg of sodium bicarbonate. In certain embodiments, the core can further comprise from about 10 mg to about 100 mg, from about 25 mg to about 75 mg, or from about 60 mg to 70 mg of calcium carbonate.

In certain embodiments, the core can further comprise from about 50 mg to about 200 mg, or about 100 mg of crospovidone. In certain embodiments, the core can further comprise from about 100 mg to about 300 mg, from about 150 mg to about 275 mg, or from about 200 mg to about 255 mg of mannitol. In certain embodiments, the core can further optionally comprise from about 50 mg to about 250 mg, from about 100 mg to about 20 mg, or about 150 mg of hydroxypropyl methylcellulose with an average molecular weight of about 400,000. In certain embodiments, the core can further comprise from about 100 mg to about 450 mg, from about 150 mg to about 350 mg, or from about 150 mg to about 300 mg of hydroxypropyl methylcellulose with an average molecular weight of about 164,000. In certain embodiments, the core can further comprise from about 1 mg to about 10 mg, from about 2 mg to about 8 mg, or from about 3 mg to about 5 mg of fumed silica. In certain embodiments, the core can further comprise from about 1 mg to about 15 mg, from about 5 mg to about 10 mg, or about 8 mg of magnesium stearate. In certain embodiments, the pyridostigmine bromide gastroretentive tablets can further comprise a functional coat. In certain embodiments, the functional coat can comprise ammonio methacrylate copolymer, triethyl citrate, talc, and combinations thereof. In certain embodiments, the functional coat of the pyridostigmine bromide gastroretentive tablets can comprise from about 100 mg to about 250 mg, from about 125 mg to about 200 mg, or from about 145 mg to about 190 mg of ammonio methacrylate copolymer. In certain embodiments, the functional coat of the pyridostigmine bromide gastroretentive tablets can further comprise from about 10 mg to about 50 mg, from about 15 mg to about 35 mg, from about 20 mg to about 30 mg of triethyl citrate. In certain embodiments, the functional coat of the pyridostigmine bromide gastroretentive tablets can further comprise from about 10 mg to about 50 mg, from about 20 mg to about 40 mg, or from about 25 mg to about 30 mg of talc.

In certain embodiments, the pyridostigmine bromide gastroretentive tablets can comprise a core, and a functional coat. In certain embodiments, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, fumed silica, magnesium stearate, and combinations thereof. In certain embodiments, the core of the pyridostigmine bromide gastroretentive tablets can comprise from about 50 mg to about 200 mg, from about 100 mg to about 150 mg, or about 135 mg of pyridostigmine bromide. In certain embodiments, the core can further comprise from about 50 mg to about 150 mg, from about 80 mg to about 30 mg, or about 125 mg of succinic acid. In certain embodiments, the core can further comprise from about 30 mg to about 100 mg, or from about 50 mg to about 75 mg of sodium bicarbonate. In certain embodiments, the core can further comprise from about 25 mg to about 150 mg, from about 50 mg to about 100 mg, or from about 60 mg to about 75 mg of calcium carbonate. In certain embodiments, the core can further comprise from about 100 mg to about 300 mg, from about 150 mg to about 250 mg, or about 200 mg of crospovidone. In certain embodiments, the core can further comprise from about 10 mg to about 200 mg, from about 25 mg to about 50 mg, from about 100 mg to about 200 mg, or from about 150 mg to about 175 mg of mannitol. In certain embodiments, the core can further optionally comprise from about 25 mg to about 150 mg, from about 50 mg to about 125 mg, or about 100 mg of hydroxypropyl methylcellulose with an average molecular weight of about 400,000. In certain embodiments, the core can further comprise from about 50 mg to about 450 mg, or from about 100 mg to about 200 mg of hydroxypropyl methylcellulose with an average molecular weight of about 164,000. In certain embodiments, the core can further comprise from about 1 mg to about 10 mg, from about 2 mg to about 8 mg, or from about 3 mg to about 5 mg of fumed silica. In certain embodiments, the core can further comprise from about 1 mg to about 15 mg, from about 5 mg to about 10 mg, or about 8 mg of magnesium stearate. In certain embodiments, the pyridostigmine bromide gastroretentive tablets can further comprise a functional coat. In certain embodiments, the functional coat can comprise one or more of ammonio methacrylate copolymer, triethyl citrate, talc, and combinations thereof. In certain embodiments, the functional coat of the pyridostigmine bromide gastroretentive tablets can comprise from about 50 mg to about 250 mg, from about 100 mg to about 200 mg, or from about 125 mg to about 150 mg of ammonio methacrylate copolymer. In certain embodiments, the functional coat of the pyridostigmine bromide gastroretentive tablets can further comprise from about 10 mg to about 40 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 20 mg to about 40 mg, or from about 25 mg to about 35 mg of talc.

In certain embodiments, the pyridostigmine bromide gastroretentive tablets can comprise a core, and a functional coat. In certain embodiments, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose fumed silica, magnesium stearate, and combinations thereof. In certain embodiments, the core of the pyridostigmine bromide gastroretentive tablets can comprise from about 100 mg to about 250 mg, from about 150 mg to about 200 mg, or about 180 mg of pyridostigmine bromide. In certain embodiments, the core can further comprise from about 50 mg to about 150 mg, from about 80 mg to about 30 mg, or about 125 mg of succinic acid. In certain embodiments, the core can further comprise from about 30 mg to about 100 mg, or from about 50 mg to about 75 mg of sodium bicarbonate. In certain embodiments, the core can further comprise from about 25 mg to about 150 mg, from about 70 mg to about 125 mg, or about 100 mg of calcium carbonate. In certain embodiments, the core can further comprise from about 100 mg to about 300 mg, from about 150 mg to about 250 mg, or about 200 mg of crospovidone. In certain embodiments, the core can further comprise from about 50 mg to about 200 mg, from about 75 mg to about 150 mg, or from about 100 mg to about 125 mg of mannitol. In certain embodiments, the core can further optionally comprise from about 25 mg to about 150 mg, from about 50 mg to about 125 mg, or about 100 mg of hydroxypropyl methylcellulose with an average molecular weight of about 400,000. In certain embodiments, the core can further comprise from about 50 mg to about 300 mg, or from about 100 mg to about 200 mg of hydroxypropyl methylcellulose with an average molecular weight of about 164,000. In certain embodiments, the core can further comprise from about 1 mg to about 10 mg, from about 2 mg to about 8 mg, or from about 3 mg to about 5 mg of fumed silica. In certain embodiments, the core can further comprise from about 1 mg to about 15 mg, from about 5 mg to about 10 mg, or about 8 mg of magnesium stearate. In certain embodiments, the pyridostigmine bromide gastroretentive tablets can further comprise a functional coat. In certain embodiments, the functional coat can comprise one or more of ammonio methacrylate copolymer, triethyl citrate, talc, and combinations thereof. In certain embodiments, the functional coat of the pyridostigmine bromide gastroretentive tablets can comprise from about 50 mg to about 200 mg, from about 75 mg to about 150 mg, or from about 100 mg to about 125 mg of ammonio methacrylate copolymer. In certain embodiments, the functional coat of the pyridostigmine bromide gastroretentive tablets can further comprise from about 10 mg to about 40 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 15 mg to about 40 mg, or from about 20 mg to about 30 mg of talc.

In certain embodiments, the pyridostigmine bromide gastroretentive tablets can comprise a core, and a functional coat. In certain embodiments, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, fumed silica, magnesium stearate, and combinations thereof. In certain embodiments, the core of the pyridostigmine bromide gastroretentive tablets can comprise from about 150 mg to about 400 mg, from about 200 mg to about 450 mg, or from about 250 to about 310 mg of pyridostigmine bromide. In certain embodiments, the core can further comprise from about 25 mg to about 125 mg, from about 50 mg to about 100 mg, or from about 75 mg to about 90 mg of succinic acid. In certain embodiments, the core can further comprise from about 30 mg to about 100 mg, or from about 50 mg to about 75 mg of sodium bicarbonate. In certain embodiments, the core can further comprise from about 20 mg to about 100 mg, from about 40 mg to about 80 mg, or from about 60 mg to about 75 mg of calcium carbonate. In certain embodiments, the core can further comprise from about 50 mg to about 150 mg, from about 75 mg to about 125 mg, or about 100 mg of crospovidone. In certain embodiments, the core can further comprise from about 25 mg to about 175 mg, from about 50 mg to about 150 mg, or from about 70 mg to about 125 mg of mannitol. In certain embodiments, the core can further optionally comprise from about 50 mg to about 200 mg, from about 100 mg to about 175 mg, or about 150 mg of hydroxypropyl methylcellulose with an average molecular weight of about 400,000. In certain embodiments, the core can further comprise from about 50 mg to about 200 mg, from about 100 mg to about 175 mg, or about 150 mg of hydroxypropyl methylcellulose with an average molecular weight of about 164,000. In certain embodiment, the core can further comprise from about 1 mg to about 20 mg, from about 5 mg to about 15 mg, or about 10 mg of fumed silica. In certain embodiment, the core can further comprise from about 5 mg to about 20 mg, from about 10 mg to about 15 mg, or about 12 mg of magnesium stearate. In certain embodiments, the pyridostigmine bromide gastroretentive tablets can further comprise a functional coat. In certain embodiments, the functional coat can comprise one or more of ammonio methacrylate copolymer, triethyl citrate, talc, and combinations thereof. In certain embodiments, the functional coat of the pyridostigmine bromide gastroretentive tablets can comprise from about 50 mg to about 200 mg, from about 75 mg to about 175 mg, or from about 125 mg to about 150 mg of ammonio methacrylate copolymer. In certain embodiments, the functional coat of the pyridostigmine bromide gastroretentive tablets can further comprise from about 10 mg to about 40 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 15 mg to about 40 mg, or from about 25 mg to about 30 mg of talc.

In certain embodiments, the pyridostigmine bromide gastroretentive tablets can comprise a core, a functional coat, a seal coat, a drug layer and an over coat. In certain embodiments, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, fumed silica, magnesium stearate, oxide pigment black, and combinations thereof. In certain embodiments, the core of the pyridostigmine bromide gastroretentive tablets can comprise from about 50 mg to about 200 mg, from about 100 mg to about 150 mg, or about 135 mg of pyridostigmine bromide. In certain embodiments, the core can further comprise from about 25 mg to about 125 mg, from about 50 mg to about 100 mg, or from about 75 mg to about 90 mg of succinic acid. In certain embodiments, the core can further comprise from about 30 mg to about 100 mg, from about 50 mg to about 75 mg, or about 55 mg of sodium bicarbonate. In certain embodiments, the core can further comprise from about 20 mg to about 100 mg, from about 40 mg to about 80 mg, or from about 60 mg to about 70 mg of calcium carbonate. In certain embodiments, the core can further comprise from about 50 mg to about 150 mg, from about 75 mg to about 125 mg, or about 100 mg of crospovidone. In certain embodiments, the core can further comprise from about 150 mg to about 400 mg, from about 200 mg to about 350 mg, or from about 250 mg to about 300 mg of mannitol. In certain embodiments, the core can further optionally comprise from about 50 mg to about 200 mg, from about 100 mg to about 175 mg, or about 150 mg of hydroxypropyl methylcellulose with an average molecular weight of about 400,000. In certain embodiments, the core can further comprise from about 50 mg to about 200 mg, from about 100 mg to about 175 mg, or about 150 mg of hydroxypropyl methylcellulose with an average molecular weight of about 164,000. In certain embodiments, the core can further comprise from about 1 mg to about 20 mg, from about 5 mg to about 15 mg, or about 10 mg of fumed silica. In certain embodiments, the core can further comprise from about 5 mg to about 20 mg, from about 10 mg to about 15 mg, or about 12 mg of magnesium stearate. In certain embodiments, the core can further optionally comprise from about 5 mg to about 20 mg, or from about 10 mg to about 15 mg, or about 12 mg of oxide pigment black. In certain embodiments, the pyridostigmine bromide gastroretentive tablets can further comprise a functional coat. In certain embodiments, the functional coat can comprise one or more of ammonio methacrylate copolymer, triethyl citrate, talc, and combinations thereof. In certain embodiments, the functional coat of the pyridostigmine bromide gastroretentive tablets can comprise from about 50 mg to about 200 mg, from about 75 mg to about 175 mg, or from about 125 mg to about 150 mg of ammonio methacrylate copolymer. In certain embodiments, the functional coat of the pyridostigmine bromide gastroretentive tablets can further comprise from about 10 mg to about 40 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 15 mg to about 40 mg, or from about 25 mg to about 30 mg of talc. In certain embodiments, the pyridostigmine bromide gastroretentive tablets can further comprise a seal coat. In certain embodiments the seal coat can comprise from about 1 mg to about 20 mg, from about 5 mg to about 15 mg, or about 10 mg of polyvinyl alcohol-based polymer. In certain embodiments, the pyridostigmine bromide gastroretentive tablets can further comprise a drug layer. In certain embodiments, the drug layer can comprise pyridostigmine bromide, hydroxypropyl cellulose, and combinations thereof. In certain embodiments, the drug layer can comprise from about 10 mg to about 100 mg, from about 25 mg to about 75 mg, or from about 40 mg to about 50 mg of pyridostigmine bromide. In certain embodiments, the drug layer can comprise from about 1 mg to about 20 mg, from about 5 mg to about 15 mg, or from about 8 mg to about 12 mg of hydroxypropyl cellulose. In certain embodiments, the pyridostigmine bromide gastroretentive tablets can further comprise an over coat. In certain embodiments, the over coat can comprise from about 20 mg to about 60 mg, from about 30 mg to about 50 mg, or about 40 mg of polyvinyl alcohol-based polymer.

In certain embodiments, the pyridostigmine bromide gastroretentive tablets can comprise a core, and a functional coat. In certain embodiments, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, fumed silica, magnesium stearate, and combinations thereof. In certain embodiments, the core of the pyridostigmine bromide gastroretentive tablets can comprise from about 200 mg to about 400 mg, from about 250 mg to about 350 mg, or from about 285 mg, to about 315 mg of pyridostigmine bromide. In certain embodiments, the core can further comprise from about 25 mg to about 125 mg, from about 50 mg to about 100 mg, or from about 75 mg to about 90 mg of succinic acid. In certain embodiments, the core can further comprise from about 30 mg to about 100 mg, or from about 50 mg to about 75 mg of sodium bicarbonate. In certain embodiments, the core can further comprise from about 20 mg to about 100 mg, from about 40 mg to about 80 mg, or from about 60 mg to about 75 mg of calcium carbonate. In certain embodiments, the core can further comprise from about 50 mg to about 150 mg, from about 75 mg to about 125 mg, or about 100 mg of crospovidone. In certain embodiments, the core can further optionally comprise from about 25 mg to about 175 mg, from about 50 mg to about 150 mg, from about 60 mg to about 100 mg, or from about 70 mg to about 85 mg of mannitol. In certain embodiments, the core can further comprise from about 100 mg to about 300 mg, from about 125 mg to about 250 mg, or from about 150 mg to about 200 mg of hydroxypropyl methylcellulose with an average molecular weight of about 400,000. In certain embodiments, the core can further comprise from about 100 mg to about 300 mg, from about 125 mg to about 250 mg, or from about 150 mg to about 200 mg of hydroxypropyl methylcellulose with an average molecular weight of about 164,000. In certain embodiments, the core can further comprise from about 1 mg to about 20 mg, from about 5 mg to about 15 mg, or about 10 mg of fumed silica. In certain embodiments, the core can further comprise from about 5 mg to about 20 mg, from about 10 mg to about 15 mg, or about 12 mg of magnesium stearate. In certain embodiments, the pyridostigmine bromide gastroretentive tablets can further comprise a functional coat. In certain embodiments, the functional coat can comprise one or more of ammonio methacrylate copolymer, triethyl citrate, talc, and combinations thereof. In certain embodiments, the functional coat of the pyridostigmine bromide gastroretentive tablets can comprise from about 50 mg to about 200 mg, from about 75 mg to about 175 mg, or from about 125 mg to about 150 mg of ammonio methacrylate copolymer. In certain embodiments, the functional coat of the pyridostigmine bromide gastroretentive tablets can further comprise from about 10 mg to about 40 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 15 mg to about 40 mg, or from about 25 mg to about 30 mg of talc.

In certain embodiments, the pyridostigmine bromide gastroretentive tablets can comprise a core, and a functional coat. In certain embodiments, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, fumed silica, magnesium stearate, and combinations thereof. In certain embodiments, the core of the pyridostigmine bromide gastroretentive tablets can comprise from about 100 mg to about 300 mg, from about 175 mg to about 275 mg, from about 195 mg to about 210 mg, or from about 225 mg to about 260 mg of pyridostigmine bromide. In certain embodiments, the core can further comprise from about 25 mg to about 125 mg, from about 50 mg to about 100 mg, or from about 75 mg to about 90 mg of succinic acid. In certain embodiments, the core can further comprise from about 30 mg to about 100 mg, or from about 50 mg to about 75 mg of sodium bicarbonate. In certain embodiments, the core can further comprise from about 20 mg to about 100 mg, from about 40 mg to about 80 mg, or from about 60 mg to about 75 mg of calcium carbonate. In certain embodiments, the core can further comprise from about 50 mg to about 150 mg, from about 75 mg to about 125 mg, or about 100 mg of crospovidone. In certain embodiments, the core can further optionally comprise from about 50 mg to about 200 mg, from about 100 mg to about 175 mg, from about 120 mg to about 125 mg, or from about 120 mg to about 175 mg of mannitol. In certain embodiments, the core can further comprise from about 100 mg to about 300 mg, from about 125 mg to about 250 mg, or from about 150 mg to about 215 mg of hydroxypropyl methylcellulose with an average molecular weight of about 400,000. In certain embodiments, the core can further comprise from about 100 mg to about 300 mg, from about 125 mg to about 250 mg, or from about 150 mg to about 215 mg of hydroxypropyl methylcellulose with an average molecular weight of about 164,000. In certain embodiments, the core can further comprise from about 1 mg to about 20 mg, from about 5 mg to about 15 mg, or about 10 mg of fumed silica. In certain embodiments, the core can further comprise from about 5 mg to about 20 mg, from about 10 mg to about 15 mg, or about 12 mg of magnesium stearate. In certain embodiments, the pyridostigmine bromide gastroretentive tablets can further comprise a functional coat. In certain embodiments, the functional coat can comprise one or more of ammonio methacrylate copolymer, triethyl citrate, talc, and combinations thereof. In certain embodiments, the functional coat of the pyridostigmine bromide gastroretentive tablets can comprise from about 50 mg to about 200 mg, from about 75 mg to about 175 mg, or from about 125 mg to about 150 mg of ammonio methacrylate copolymer. In certain embodiments, the functional coat of the pyridostigmine bromide gastroretentive tablets can further comprise from about 10 mg to about 40 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 15 mg to about 40 mg, or from about 25 mg to about 30 mg of talc.

In certain embodiments, the pyridostigmine bromide gastroretentive tablets can comprise a core, and a functional coat. In certain embodiments, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, fumed silica, magnesium stearate, and combinations thereof. In certain embodiments, the core of the pyridostigmine bromide gastroretentive tablets can comprise from about 50 mg to about 200 mg, from about 70 mg to about 170 mg, or from about 100 mg to about 160 mg of pyridostigmine bromide. In certain embodiments, the core can further comprise from about 25 mg to about 125 mg, from about 50 mg to about 100 mg, or from about 75 mg to about 90 mg of succinic acid. In certain embodiments, the core can further comprise from about 30 mg to about 100 mg, or from about 50 mg to about 75 mg of sodium bicarbonate. In certain embodiments, the core can further comprise from about 20 mg to about 100 mg, from about 40 mg to about 80 mg, or from about 60 mg to about 75 mg of calcium carbonate. In certain embodiments, the core can further comprise from about 50 mg to about 150 mg, from about 75 mg to about 125 mg, or about 100 mg of crospovidone. In certain embodiments, the core can further optionally comprise from about 200 mg to about 350 mg, from about 210 mg to about 310 mg, or from about 220 to about 280 mg of mannitol. In certain embodiments, the core can further comprise from about 100 mg to about 300 mg, from about 125 mg to about 250 mg, or from about 150 mg to about 200 mg of hydroxypropyl methylcellulose with an average molecular weight of about 400,000. In certain embodiments, the core can further comprise from about 100 mg to about 300 mg, from about 125 mg to about 250 mg, or from about 150 mg to about 200 mg of hydroxypropyl methylcellulose with an average molecular weight of about 164,000. In certain embodiments, the core can further comprise from about 1 mg to about 20 mg, from about 5 mg to about 15 mg, or about 10 mg of fumed silica. In certain embodiments, the core can further comprise from about 5 mg to about 20 mg, from about 10 mg to about 15 mg, or about 12 mg of magnesium stearate. In certain embodiments, the pyridostigmine bromide gastroretentive tablets can further comprise a functional coat. In certain embodiments, the functional coat can comprise one or more of ammonio methacrylate copolymer, triethyl citrate, talc, and combinations thereof. In certain embodiments, the functional coat of the pyridostigmine bromide gastroretentive tablets can comprise from about 50 mg to about 200 mg, from about 75 mg to about 175 mg, or from about 125 mg to about 150 mg of ammonio methacrylate copolymer. In certain embodiments, the functional coat of the pyridostigmine bromide gastroretentive tablets can further comprise from about 10 mg to about 40 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 15 mg to about 40 mg, or from about 25 mg to about 30 mg of talc.

In certain embodiments, the pyridostigmine bromide gastroretentive tablets can comprise a core, a functional coat, a seal coat, a drug layer, and an over coat. In certain embodiments, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, fumed silica, magnesium stearate, and combinations thereof. In certain embodiments, the core of the pyridostigmine bromide gastroretentive tablets can comprise from about 50 mg, to about 200 mg, from about 100 mg to about 150 mg, or about 135 mg of pyridostigmine bromide. In certain embodiments, the core can further comprise from about 25 mg to about 125 mg, from about 50 mg to about 100 mg, or from about 75 mg to about 90 mg of succinic acid. In certain embodiments, the core can further comprise from about 30 mg to about 100 mg, from about 50 mg to about 75 mg, or about 55 mg of sodium bicarbonate. In certain embodiments, the core can further comprise from about 20 mg to about 100 mg, from about 40 mg to about 80 mg, or from about 60 mg to about 70 mg of calcium carbonate. In certain embodiments, the core can further comprise from about 50 mg to about 150 mg, from about 75 mg to about 125 mg, or about 100 mg of crospovidone. In certain embodiments, the core can further comprise from about 175 mg to about 300 mg, from about 200 mg to about 275 mg, or from about 230 mg to 240 mg of mannitol. In certain embodiments, the core can further optionally comprise from about 50 mg to about 200 mg, from about 100 mg to about 175 mg, or about 150 mg of hydroxypropyl methylcellulose with an average molecular weight of about 400,000. In certain embodiments, the core can further comprise from about 50 mg to about 200 mg, from about 100 mg to about 175 mg, or about 150 mg of hydroxypropyl methylcellulose with an average molecular weight of about 164,000. In certain embodiments, the core can further comprise from about 1 mg to about 20 mg, from about 5 mg to about 15 mg, or about 10 mg of fumed silica. In certain embodiments, the core can further comprise from about 5 mg to about 20 mg, from about 10 mg to about 15 mg, or about 12 mg of magnesium stearate. In certain embodiments, the core can further comprise from about 1 mg to about 20 mg, from about 5 mg to about 15 mg, or from about 7 mg to about 12 mg of oxide pigment black. In certain embodiments, the pyridostigmine bromide gastroretentive tablets can further comprise a functional coat. In certain embodiments, the functional coat can comprise one or more of ammonio methacrylate copolymer, triethyl citrate, talc, and combinations thereof. In certain embodiments, the functional coat of the pyridostigmine bromide gastroretentive tablets can comprise from about 50 mg to about 200 mg, from about 75 mg to about 175 mg, or from about 125 mg to about 150 mg of ammonio methacrylate copolymer. In certain embodiments, the functional coat of the pyridostigmine bromide gastroretentive tablets can further comprise from about 10 mg to about 40 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 15 mg to about 40 mg, or from about 25 mg to about 30 mg of talc. In certain embodiments, the pyridostigmine bromide gastroretentive tablets can further comprise a seal coat. In certain embodiments, the seal coat can comprise polyvinyl alcohol-based polymer. In certain embodiments, the seal coat can comprise from about 1 mg to about 20 mg, from about 5 mg to about 15 mg, or about 10 mg of polyvinyl alcohol-based polymer. In certain embodiments, the pyridostigmine bromide gastroretentive tablets can further comprise a drug layer. In certain embodiments, the drug layer can comprise pyridostigmine bromide, and hydroxypropyl cellulose. In certain embodiments, the drug layer can comprise from about 20 mg to about 75 mg, from about 30 mg to about 60 mg, or from about 40 mg to about 50 mg of pyridostigmine bromide. In certain embodiments, the drug layer can further comprise from about 1 mg to about 20 mg, from about 5 mg to about 15 mg, or about 9 mg of hydroxypropyl cellulose. In certain embodiments, the pyridostigmine bromide gastroretentive tablets can further comprise an over coat. In certain embodiments, the overcoat can comprise polyvinyl alcohol-based polymer. In certain embodiments, the over coat can comprise from about 10 mg to about 60 mg, from about 20 mg to about 50 mg, or about 40 mg of polyvinyl alcohol-based polymer.

In certain embodiments, the pyridostigmine bromide gastroretentive tablets can comprise a core, a functional coat, a seal coat, a drug layer, and an over coat. In certain embodiments, the core of the pyridostigmine bromide gastroretentive tablets can comprise one or more of pyridostigmine bromide, succinic acid, sodium bicarbonate, calcium carbonate, crospovidone, mannitol, hydroxypropyl methylcellulose, fumed silica, magnesium stearate, and combinations thereof. In certain embodiments, the core of the pyridostigmine bromide gastroretentive tablets can comprise from about 25 mg to about 125 mg, from about 50 mg to about 100 mg, or about 75 mg of pyridostigmine bromide. In certain embodiments, the core can further comprise from about 25 mg to about 125 mg, from about 50 mg to about 100 mg, or from about 75 mg to about 90 mg of succinic acid. In certain embodiments, the core can further comprise from about 30 mg to about 100 mg, from about 50 mg to about 75 mg, or about 55 mg of sodium bicarbonate. In certain embodiments, the core can further comprise from about 20 mg to about 100 mg, from about 40 mg to about 80 mg, or from about 60 mg to about 70 mg of calcium carbonate. In certain embodiments, the core can further comprise from about 50 mg to about 150 mg, from about 75 mg to about 125 mg, or about 100 mg of crospovidone. In certain embodiments, the core can further comprise from about 200 mg to about 350 mg, from about 250 mg to about 300 mg, or from about 270 mg to about 280 mg of mannitol. In certain embodiments, the core can further optionally comprise from about 50 mg to about 200 mg, from about 100 mg to about 175 mg, or about 150 mg of hydroxypropyl methylcellulose with an average molecular weight of about 400,000. In certain embodiments, the core can further comprise from about 50 mg to about 200 mg, from about 100 mg to about 175 mg, or about 150 mg of hydroxypropyl methylcellulose with an average molecular weight of about 164,000. In certain embodiments, the core can further comprise from about 1 mg to about 20 mg, from about 5 mg to about 15 mg, or about 10 mg of fumed silica. In certain embodiments, the core can further comprise from about 5 mg to about 20 mg, from about 10 mg to about 15 mg, or about 12 mg of magnesium stearate. In certain embodiments, the core can further comprise from about 1 mg to about 20 mg, from about 5 mg to about 15 mg, or from about 7 mg to about 12 mg of oxide pigment black. In certain embodiments, the pyridostigmine bromide gastroretentive tablets can further comprise a functional coat. In certain embodiments, the functional coat can comprise one or more of ammonio methacrylate copolymer, triethyl citrate, talc, and combinations thereof. In certain embodiments, the functional coat of the pyridostigmine bromide gastroretentive tablets can comprise from about 50 mg to about 200 mg, from about 75 mg to about 175 mg, or from about 125 mg to about 150 mg of ammonio methacrylate copolymer. In certain embodiments, the functional coat of the pyridostigmine bromide gastroretentive tablets can further comprise from about 10 mg to about 40 mg, from about 15 mg to about 30 mg, or from about 20 mg to about 25 mg of triethyl citrate. In certain embodiments, the functional coat of the pyridostigmine bromide gastroretentive tablets can further comprise from about 10 mg to about 50 mg, from about 15 mg to about 40 mg, or from about 25 mg to about 30 mg of talc. In certain embodiments, the pyridostigmine bromide gastroretentive tablets can further comprise a seal coat. In certain embodiments, the seal coat can comprise polyvinyl alcohol-based polymer. In certain embodiments, the seal coat can comprise from about 1 mg to about 20 mg, from about 5 mg to about 15 mg, or about 10 mg of polyvinyl alcohol-based polymer. In certain embodiments, the pyridostigmine bromide gastroretentive tablets can further comprise a drug layer. In certain embodiments, the drug layer can comprise one of more of pyridostigmine bromide, and hydroxypropyl cellulose and combinations thereof. In certain embodiments, the drug layer can comprise from about 10 mg to about 50 mg, from about 20 mg to about 40 mg, or about 30 mg of pyridostigmine bromide. In certain embodiments, the drug layer can further comprise from about 1 mg to about 20 mg, from about 5 mg to about 15 mg, or about 9 mg of hydroxypropyl cellulose. In certain embodiments, the pyridostigmine bromide gastroretentive tablets can further comprise an over coat. In certain embodiments, the overcoat can comprise polyvinyl alcohol-based polymer. In certain embodiments, the over coat can comprise from about 10 mg to about 60 mg, from about 20 mg to about 50 mg, or about 40 mg of polyvinyl alcohol-based polymer.

6.2.2.6 Features of Gastroretentive Dosage Forms

The gastroretentive tablets of the disclosure combine the following two key attributes: gastric retention and continuous controlled drug delivery for up to about 24 hours. In certain embodiments, the disclosure provides gastroretentive tablets of pyridostigmine that are suitable for providing stable pyridostigmine levels, with minimized initial burst release/dose dumping of the drug, for an extended period of time. This is particularly desirable for myasthenia gravis (MG) patients, as the constant level of pyridostigmine has been shown to improve therapeutic outcome and quality of life. Quality of life and compliance are also enhanced with the reduction or elimination of dose dumping of pyridostigmine, as experienced with the currently marketed ER formulation, and the concomitant reduction in undesirable side effects. FIG. 18 compares pharmacokinetic data for gastroretentive Tablet 8 ($T_1$), pellet compositions $T_2$, and marketed pyridostigmine products, e.g., MESTINON® tablets (60 mg/TID) ($R_2$) and MESTINON® TIMESPAN tablets (180 mg/QD) ($R_1$). FIG. 18 demonstrates that bioavailability of gastroretentive Tablet 8 ($T_1$) is comparable to MESTINON® ($R_2$) and MESTINON® TIMESPAN tablets ($R_1$) in the fed state. Pharmacokinetic data from FIG. 18 demonstrates that gastroretentive tablets of the disclosure (T1), by releasing the drug in the upper GI tract, provide comparable bioavailability to marketed pyridostigmine products (R1), and provide extended plasma concentration profiles for 24 hours. In certain embodiments, the gastroretentive tablets of the present disclosure provide for reduced initial burst release, of pyridostigmine bromide of at least 14 hours. In particular embodiments, the reduced initial burst release comprises an in vitro release of between about 20% and about 35% of the pyridostigmine bromide within 2 hours of dissolution in a dissolution medium.

The gastroretentive pyridostigmine tablets of the disclosure provide significant therapeutic advantages over the currently marketed pyridostigmine products with respect to the following attributes: 1) enhanced control of symptoms associated with MG with once-a-day dosing, 2) rapid onset of effect/reduced lag time and consistent blood levels during the daytime to treat progressive muscle weakness and fatigue known to build up by the evening, 3) reduced initial drug concentration (e.g., reduced initial burst release; minimized initial burst release) sufficient to provide therapeutic effect without GI side effects, 4) lower, but still therapeutic, blood levels during the night for treating nighttime symptoms and providing uninterrupted sleep, 5) improved tolerability of the drug with reduced adverse events compared to fluctuating blood levels from an IR formulation, 6) reduced treatment burden and improved adherence/compliance due to less frequent dosing, and 7) better patient satisfaction and quality of life with improved functionality throughout the day and reduced reliance on caregivers.

In certain embodiments, the gastroretentive compositions of the disclosure can comprise an immediate release layer and an extended release component. The immediate release layer comprises pyridostigmine bromide, and the extended release component can comprise a core coated with a permeable elastic membrane. In certain embodiments, the core can comprise pyridostigmine bromide, at least one gas-generating agent (e.g., sodium bicarbonate, calcium carbonate), at least one acid (e.g., succinic acid), and at least one swellable water-soluble hydrophilic polymer. In certain embodiments, the gastroretentive tablets of the disclosure can include an orifice in the functional coat.

In certain embodiments, amounts of succinic acid and the gas-generating agent(s) are optimized to minimize the floating lag time.

In certain embodiments, compositions of the disclosure include a seal coat between the core and the functional coat. In certain other embodiments, the compositions of the disclosure do not include a seal coat between the core and the functional coat. Surprisingly, it was observed that absence of a seal coat between the tablet core and the functional coat resulted in minimizing the floating lag time. Tablets 8 and 8A contained a seal coat between the tablet core and the functional coat; and Tablets 11/11A, 13/13A, and 15/15A did not include a seal coat between the tablet core and the functional coat. FIG. 10 compares floating lag times of Tablets 8, 11, 13, and 15, with and without orifice/hole, at 200 mg functional coating weight gain, and Tablets 8A, 11A, 13A, and 15A, with and without orifice/hole, at 250 mg functional coating weight gain. The flotation studies were performed, using Rotating Bottle method at 5 rpm and 37° C., in 200 ml of a dissolution medium with pH 4.5 comprising 100 mM NaCl. FIG. 10 demonstrates that Tablets 8/8A, containing a seal coat, exhibit longer floating lag times compared to tablets without a seal coat (Tablets 11/11A, 13/13A, and 15/15A).

In certain embodiments, it was observed that tablets containing a mixture of BENECEL® K4M PH DC (2700-5040 mPa·s) and METHOCEL® K100 Prem LVCR(80-120 mPa·s) (Tablets 22, 23, and 34) provided a better controlled release compared to tablets containing BENECEL® K4M PH DC (Tablet 8) alone. FIGS. 17 and 23 compare in vitro dissolution profiles of Tablets 8, 22, and 23; and Tablets 8 and 34, respectively. FIGS. 17 and 23 demonstrate that Tablets 22, 23, and 34 (all containing a mixture of BENECEL® K4M PH DC and METHOCEL® K100 Prem LVCR) provided better controlled release compared to Tablet 8 (containing BENECEL® K4M PH DC alone).

FIGS. 20 and 21 compare pharmacokinetic data for gastroretentive Tablet 34 (gastroretentive tablet with hole) and Tablet 35 (gastroretentive tablet without hole), respectively. FIGS. 20 and 21 demonstrate that Tablets 34 and 35 provide therapeutic plasma concentrations of pyridostigmine bromide for between about 14 hours and about 20 hours.

In certain embodiments, the gastroretentive tablets of the disclosure can include an immediate release layer and an extended release component. FIG. 23 compares in vitro dissolution profiles of a tablet containing an immediate release drug layer (Tablet 34), a tablet with no immediate release drug layer (Tablet 8), and a tablet of MESTINON® TIMESPAN. The figure demonstrates that Tablet 8 (without IR drug layer) exhibits minimized initial burst release; and Tablet 34 (with IR drug layer) provides an immediate release of a therapeutic amount of pyridostigmine bromide, with reduced initial burst release (between about 20% and about 35% drug release in about 2 hours) of the drug, compared to MESTINON® TIMESPAN.

FIG. 24 compares pharmacokinetic data for gastroretentive Tablet 34, a tablet with a hole in the functional coat, under LF-LC breakfast conditions (Condition I) and HF-HC breakfast conditions (Condition II), and MESTINON® TIMESPAN (Condition II). FIG. 24 demonstrates that MESTINON® TIMESPAN provides higher drug plasma concentrations between about 0 and 5 hours compared to Tablet 34 under Conditions I and II. FIG. 24 further demonstrates that Tablet 34, under Conditions I and II, provides higher drug plasma concentrations of pyridostigmine bromide over an extended time period, e.g., about 7 hours or beyond, compared to MESTINON® TIMESPAN.

In certain embodiments, the compositions of the disclosure can comprise horizontally compressed oval, modified oval, or capsule shapes for easy swallowing. In certain embodiments, the tablets can be compressed using oval, modified oval, capsule shaped, or any other shaping tool. In certain embodiments, the horizontally compressed tablets can comprise a long axis having a length of between about 12 mm and about 22 mm, and a short axis having a length of between about 8 mm and about 11 mm. In certain embodiments, the tablets can have a long axis of about 12 mm, about 13 mm, about 14 mm, about 15 mm, about 16 mm, about 17 mm, about 18 mm, about 19 mm, about 20 mm, about 21 mm, about 22 mm, or any intermediate lengths therein. In certain embodiments, the tablets can have a short axis of about 8 mm, about 9 mm, about 10 mm, about 11 mm, or any intermediate lengths therein. In certain embodiments, the compressed multilayered tablets can comprise a long axis having a length of about 20±2 mm, and a short axis having a length of between about 10±2 mm. In certain embodiments, the initial tablet size (10 mm×19 mm) can be reasonably small for swallowability, and once swallowed, the tablet is designed for rapid generation of carbon dioxide ($CO_2$) within the core to increase its buoyancy. Within 30 minutes of coming into contact with simulated gastric medium, the tablet starts floating and transforms into an oblong shape with major and minor axes having lengths of about 26 and 18 mm respectively, which can be maintained for at least about 14 hours.

The gastroretentive tablets of the disclosure can comprise an expanding hydrophilic core and a rate-controlling membrane surrounding the core. The membrane can expand rapidly and provide a protective shell that stretches upon hydration to accommodate the rapidly expanding hydrophilic core, and then acts as a rate-controlling membrane that controls the release rate of the drug. In certain embodiments, the gastroretentive tablets of the disclosure, when in contact with simulated gastric medium, can expand in about 60 minutes or less, to a size that prevents its passage through a pyloric sphincter. In certain embodiments, the gastroretentive tablets of the disclosure can float in about 40 minutes or less, expand in about 60 minutes or less to a size that prevents its passage through pyloric sphincter, and provide extended release of pyridostigmine for about 24 hours. In certain embodiments, the gastroretentive tablets of the disclosure can float in about 40 minutes or less in 50 mM pH 4.5 buffer containing 100 mM NaCl. In certain embodiments, the gastroretentive tablets of the disclosure can float in about 35 minutes, about 34 minutes, about 33 minutes, about 32 minutes, about 31 minutes, about 30 minutes, about 29 minutes, about 28 minutes, about 27 minutes, about 26 minutes, about 25 minutes, about 24 minutes, about 23 minutes, about 22 minutes, about 21 minutes, about 20 minutes, about 19 minutes, about 18 minutes, about 17 minutes, about 16 minutes, about 15 minutes or less, or any intermediate time periods, in 50 mM pH 4.5 buffer containing 100 mM NaCl. FIG. 10 provides flotation lag times of the compositions of the disclosure containing 200 mg and 250 mg coating weight gains of the functional coat. In certain embodiments, the gastroretentive tablets of the disclosure can expand in less than about 60 minutes to a size that prevents their passage through the pyloric sphincter. In certain embodiments, the gastroretentive tablets of the disclosure can exhibit at least about 200% to about 800% volume gain from its original volume at 60 minutes, measured using a Rotating Bottle method at about 5 rpm and about 37° C., in 200 ml of pH 4.5 dissolution medium, containing about 100 mM NaCl. In certain embodiments, the gastroretentive tablets can exhibit about 200%, about 250%, about 300%, about 350%, about 400%, about 450%, about 500%, about 550%, about 600%, about 650%, about 700%, about 750%, about 800%, or any intermediate values therein, volume gain from its original volume at 60 minutes FIGS. 11-13 show volume expansions of the gastroretentive tablets of the disclosure, in pH 4.5 buffer containing about 100 mM NaCl. In certain embodiments, rapid expansion of the gastroretentive tablet can result from an initial expansion of the permeable elastic membrane and a simultaneous swelling of the hydrophilic core to support the expanded membrane.

In certain embodiments, the hydrophilic core can swell to a size that can support the expanded permeable elastic membrane. In certain embodiments, the permeable elastic membrane can keep the core intact in a swollen condition for a sufficient period of time, and provides the desired characteristics of drug release.

In certain embodiments, the gastroretentive tablets of the disclosure markedly improve absorption and bioavailability of pyridostigmine bromide.

In certain embodiments, the gastroretentive tablets of the disclosure can provide gastric retention of pyridostigmine bromide for up to about 24 hours. In certain embodiments, the gastroretentive tablets of the disclosure can provide gastric retention of pyridostigmine bromide for between, e.g., about 10 to about 24 hours, about 12 to about 24 hours, and about 14 to about 24 hours. In certain embodiments, the gastroretentive tablets of the disclosure can provide gastric retention of pyridostigmine bromide for at least about 14 hours. In certain embodiments, the gastroretentive tablets of the disclosure can maintain its integrity in a swollen state for a period of at least about 14 hours. In certain embodiments, the gastroretentive tablets of the disclosure can provide gastric retention of pyridostigmine bromide for about 24 hours. Furthermore, as the drug diffuses out of the core and the polymeric excipients in the core continue to swell, the plasticizer can leach out and the permeable elastic membrane can lose its integrity and starts to break, thereby allowing remnants of the drug formulation and the remaining contents to be expelled from the stomach at an appropriate time, e.g., after a prolonged period of drug release. FIG. 19 provides schematic and photographic representations of the gastroretentive tablets of the disclosure from its initial tablet form to its residue after complete drug release.

6.2.3. Pellets

In certain embodiments, compositions of the disclosure can be formulated as granules or pellets. In certain embodiments, the compositions of the disclosure can be formulated as pyridostigmine bromide pellets. In certain embodiments, the pellets can comprise a pyridostigmine bromide containing core coated with a functional coat/membrane. In certain embodiments, the pyridostigmine bromide containing core can be further drug-layered with a pyridostigmine bromide layer.

In certain embodiments, there can be a seal coat between the pyridostigmine bromide containing core and the functional coat/membrane, and/or between the pyridostigmine bromide layer and the functional coat/membrane. In certain embodiments, the functional coat can be further coated with an immediate release drug layer comprising pyridostigmine bromide. In certain embodiments, the immediate release drug layer is further coated with an overcoat. In certain embodiments, there is a seal coat between the immediate release drug layer and the functional coat, and/or between the immediate release drug layer and the overcoat.

In certain embodiments, the pellets can comprise a microcrystalline cellulose core (MCC), also known as a cellet. In certain embodiments, the MCC core or cellet is drug-layered with a pyridostigmine bromide layer. In certain embodiments, the drug layer can be further coated with a functional coat. In certain embodiments, there can be a seal coat between the drug layer and the functional coat.

In certain embodiments, the drug layer over the pyridostigmine containing core or the cellet core can comprise pyridostigmine bromide, a water-insoluble polymer, a plasticizer, and/or an anti-tacking agent.

In certain embodiments, the water-insoluble polymer can be ethylcellulose.

In certain embodiments, the anti-tacking agent can be one or more of silicon dioxide (SYLOID® 244FP), fumed silica (CAB-O-SIL®), talc, kaolin, or combinations thereof. In certain embodiments, the plasticizer comprises triethyl citrate, triacetin, polyethylene glycol, propylene glycol, dibutyl sebacate, or combinations thereof. In certain embodiments, the plasticizer can be triethyl citrate. In certain embodiments, the plasticizer can be dibutyl sebacate.

In certain embodiments, the drug layer can comprise pyridostigmine bromide, ethylcellulose, dibutyl sebacate, and talc. In certain embodiments, the drug layer can comprise pyridostigmine bromide, hypromellose, and talc.

In certain embodiments, the seal coat can comprise at least one water-soluble polymer comprising hypromellose and/or hydroxypropyl cellulose.

In certain embodiments, the functional coat can comprise at least one water-insoluble lipophilic material and, optionally, at least one water-soluble hydrophilic polymer. In certain embodiments, the functional coat can comprise at least one water-insoluble lipophilic polymer and at least one water-soluble hydrophilic polymer (i.e., a pore former).

In certain embodiments, the water-insoluble lipophilic material in the functional coat/membrane can be selected from the group comprising, but not limited to, ethyl acrylate and methyl methacrylate copolymer (EUDRAGIT® NE, EUDRAGIT® NM), ammonio methacrylate copolymer (EUDRAGIT® RL PO, EUDRAGIT® RS PO), carnauba wax, stearic acid, ethylcellulose (ETHOCEL™), cellulose acetate, and polyvinyl acetate dispersion (KOLLICOAT® SR). In certain embodiments, the water-soluble hydrophilic polymer comprises, but is not limited to, polyethylene glycol (PEG 400, PEG 1000, PEG 1450, PEG 3350), hydroxypropyl cellulose, polyvinyl pyrolidone (PVP), KOLLIDON® 30, KOLLICOAT® IR, mannitol, and methylcellulose (METHOCEL™ E3, METHOCEL™ E5, METHOCEL™ E6).

In certain embodiments, the functional coat further can comprise at least one plasticizer and at least one anti-tacking agent. Useful anti-tacking agents can include, but are not limited to, silicon dioxide (SYLOID® 244FP), fumed silica (CAB-O-SIL®), talc, kaolin, and combinations thereof. Useful plasticizers include, but are not limited to, triethyl citrate, triacetin, polyethylene glycol, propylene glycol, and dibutyl sebacate. In certain embodiments, the plasticizer can be triethyl citrate. In certain embodiments, the plasticizer can be dibutyl sebacate.

In certain embodiments, the pellets can be retained in capsules. In certain embodiments, a composition can consist of pellets consolidated into a packed mass for ingestion, even though the packed mass will separate into individual pellets after ingestion. Conventional methods can be used for consolidating the pellets in this manner. For example, the pellets can be placed in gelatin capsules known in the art as "hard-filled" capsules and "soft-elastic" capsules. The compositions of these capsules and procedures for filling them are known among those skilled in drug formulations and manufacture. The encapsulating material should be highly soluble so that the particles are freed and rapidly dispersed in the stomach after the capsule is ingested. In certain embodiments, the pellets can be incorporated directly into food as sprinkles.

In certain embodiments, the present disclosure provides for a pyridostigmine bromide pellet comprising an inert core, a drug layer containing pyridostigmine bromide over the inert core, and a membrane over the drug layer, wherein the membrane comprises a water-insoluble lipophilic polymer and a water-soluble hydrophilic polymer, and wherein the pellet provides extended release, with minimized initial burst release, of pyridostigmine bromide, for at least about 14 hours. In certain embodiments, the water-insoluble lipophilic polymer of the pellet of the present disclosure is selected from the group consisting of an ethyl acrylate and methyl methacrylate copolymer, an ammonio methacrylate copolymer, ethylcellulose, cellulose acetate, polyvinyl acetate, and mixtures thereof. In certain embodiments, the water-soluble hydrophilic polymer of the pellet of the present disclosure is selected from the group consisting of polyethylene glycol, hydroxypropyl cellulose, hydroxymethylcellulose, carboxymethylcellulose, polyvinyl pyrolidone, methylcellulose, xanthan gum, guar gum, sodium alginate, starch, a copolymer of polyvinyl acetate and polyvinyl pyrolidone, a copolymer of ethylene glycol and propylene glycol, a copolymer of polyvinyl alcohol and polyethylene glycol, and mixtures thereof. In certain embodiments, the pellet of the present disclosure further comprises a seal coat between the drug layer and the membrane. In certain embodiments, the seal coat of the pellet of the present disclosure comprises a water-soluble polymer selected from the group consisting of a polyvinyl alcohol-based polymer, methyl cellulose, hydroxyethyl cellulose, hydroxypropyl cellulose, hydroxypropyl methylcellulose, and mixtures thereof. In certain embodiments, the water-soluble polymer of the pellet of the present disclosure is hypromellose, hydroxypropyl cellulose, or a mixture thereof.

In certain embodiments, the pellets can comprise from about 100 mg to about 250 mg, from about 150 mg to about 200 mg, or about 180 mg of pyridostigmine bromide in a pyridostigmine bromide containing core. In certain embodiments, the pellets can comprise a seal coat. In certain embodiments, the seal coat can comprise from about 5 mg to about 30 mg, from about 10 mg to about 20 mg, or about 15 mg of hydroxypropyl cellulose. In certain embodiments, the seal coat can further comprise from about 1 mg to about 10 mg, from about 2 mg to about 5 mg, or about 3 mg of talc. In certain embodiments, the pellets can further comprise a functional coat. The functional coat can comprise from about 10 mg to about 50 mg, from about 20 mg to about 40 mg, or from about 25 mg to about 35 mg of ethyl cellulose. In certain embodiments, the functional coat can further comprise from about 1 mg to about 10 mg, from about 2 mg to about 5 mg, or about 3 mg of triethyl citrate. In certain embodiments, the functional coat can further comprise from about 1 mg to about 10 mg, from about 2 mg to about 5 mg, or about 3 mg of talc. In certain embodiments, the functional coat can further comprise from about 1 mg to about 10 mg, from about 2 mg to about 5 mg, or about 3 mg of hydroxypropyl methylcellulose with a viscosity of between about 4 cp and 6 cp.

In certain embodiments, the present disclosure provides for a pyridostigmine bromide pellet comprising an inert core, a drug layer containing pyridostigmine bromide over the inert core, and a membrane over the drug layer, wherein the membrane comprises a water-insoluble lipophilic polymer and a water-soluble hydrophilic polymer, and wherein the pellet provides extended release, with minimized initial burst release, of pyridostigmine bromide, for at least about 14 hours. In certain embodiments, the water-insoluble lipophilic polymer of the pellet of the present disclosure is selected from the group consisting of an ethyl acrylate and methyl methacrylate copolymer, an ammonio methacrylate copolymer, ethylcellulose, cellulose acetate, polyvinyl acetate, and mixtures thereof. In certain embodiments, the water-soluble hydrophilic polymer of the pellet of the present disclosure is selected from the group consisting of polyethylene glycol, hydroxypropyl cellulose, hydroxymethylcellulose, carboxymethylcellulose, polyvinyl pyrolidone, methylcellulose, xanthan gum, guar gum, sodium alginate, starch, a copolymer of polyvinyl acetate and polyvinyl pyrolidone, a copolymer of ethylene glycol and propylene glycol, a copolymer of polyvinyl alcohol and polyethylene glycol, and mixtures thereof. In certain embodiments, the pellet of the present disclosure further comprises a seal coat between the drug layer and the membrane. In certain embodiments, the seal coat of the pellet of the present disclosure comprises a water-soluble polymer selected from the group consisting of a polyvinyl alcohol-based polymer, methyl cellulose, hydroxyethyl cellulose, hydroxypropyl cellulose, hydroxypropyl methylcellulose, and mixtures thereof. In certain embodiments, the water-soluble polymer of the pellet of the present disclosure is hypromellose, hydroxypropyl cellulose, or a mixture thereof.

In certain embodiments, the pellets can comprise from about 20 mg to about 150 mg, from about 50 mg to about 100 mg, or from about 70 mg to about 80 mg of pyridostigmine bromide granules in a pyridostigmine bromide containing core. In certain embodiments, the pellet can further comprise a drug layer. In certain embodiments, the drug layer can comprise from about 50 mg to about 200 mg, from about 75 mg to about 150 mg, or from about 95 mg to about 105 mg of pyridostigmine bromide. In certain embodiments, the drug layer can further comprise from about 10 mg to about 40 mg, from about 15 mg to about 30 mg, or from about 20 mg to about 25 mg of hydroxypropyl methylcellulose. In certain embodiments, the drug layer can further comprise from about 1 mg to about 10 mg, from about 2 mg to about 8 mg, or from about 3 mg to about 5 mg of talc. In certain embodiments, the pellets can further comprise a seal coat. In certain embodiments, the seal coat can comprise from about 5 mg to about 30 mg, from about 10 mg to about 25 mg, or from about 15 mg to about 20 mg of hydroxypropyl cellulose. In certain embodiments, the seal coat can further comprise from about 1 mg to about 10 mg, from about 2 mg to about 8 mg, or from about 3 mg to about 5 mg of talc. In certain embodiments, the pellets can further comprise a functional coat. In certain embodiments, the functional coat can comprise from about 10 mg to about 100 mg, from about 25 mg to about 80 mg, or from about 50 mg to about 75 mg of ethyl cellulose. In certain embodiments, the functional coat can further comprise from about 2 mg to about 15 mg, from about 2 mg to about 10 mg, or from about 5 mg to about 8 mg of triethyl citrate. In certain embodiments, the functional coat can further comprise from about 2 mg to about 15 mg, from about 2 mg to about 10 mg, or from about 5 mg to about 8 mg of talc.

In certain embodiments, the pellets can comprise a cellet core. In certain embodiments, the pellet comprises about 100 mg of cellet core. In certain embodiments, the pellets can further comprise a drug layer. In certain embodiments, the drug layer can comprise from about 100 mg to about 300 mg, from about 125 mg to about 250 mg, or from about 150 mg to about 200 mg of pyridostigmine bromide. In certain embodiments, the drug layer can further comprise from about 10 mg to about 60 mg, from about 20 mg to about 50 mg, or from about 30 to about 40 mg of ethyl cellulose. In certain embodiments, the drug layer can further comprise from about 1 mg to about 10 mg, from about 2 mg to about 7 mg, or from about 3 mg to about 5 mg of dibutyl sebacate. In certain embodiments, the drug layer can further comprise from about 1 mg to about 15 mg, from about 5 mg to about 10 mg, or about 6 mg of talc. In certain embodiments, the pellet can further comprise a seal coat. In certain embodiments, the seal coat can comprise from about 10 mg to about 100 mg, from about 10 mg to about 85 mg, from about 50 mg to about 75 mg, or from about 15 mg to about 20 mg of hydroxypropyl methylcellulose. In certain embodiments, the seal coat can further comprise from about 1 mg to about 10 mg, from about 2 mg to about 8 mg, or from about 3 mg to about 5 mg of talc. In certain embodiments, the pellet can further comprise a functional coat. In certain embodiments, the functional coat can comprise from about 20 mg to about 120 mg, from about 30 mg to about 100 mg, from about 45 to about 85 mg, or from about 50 mg to about 75 mg of ethylcellulose. In certain embodiments, the functional coat can further comprise from about 5 mg to about 30 mg, from about 10 mg to about 25 mg, or from about 12 mg to about 18 mg of dibutyl sebacate. In certain embodiments, the functional coat can further comprise from about 1 mg to about 20 mg, from about 5 mg to about 15 mg, or from about 7 mg to about 13 mg of talc. In certain embodiments, the functional coat can further comprise from about 0.5 mg to about 5 mg, from about 1 mg to about 4 mg, or from about 2 mg to about 3 mg of fumed silica. In certain embodiments, the functional coat can further optionally comprise from about 0.5 mg to about 15 mg, from about 1 mg to about 10 mg, or from about 1.5 mg to about 2.5 mg of hydroxypropyl methylcellulose. In certain embodiments, the functional coat can further optionally comprise from about 20 mg to about 150 mg, from about 50 mg to about 120 mg, or from about 75 mg to about 100 mg of cellulose acetate. In certain embodiments, the functional coat can further optionally comprise from about 5 mg to about 40 mg, from about 10 mg to about 25 mg, or from about 15 mg to about 20 mg of polyethylene glycol.

6.3. Methods of Making

In certain embodiments, the present disclosure provides extended release pyridostigmine compositions suitable for maintaining stable plasma concentrations, with minimized initial burst release/dose dumping, of pyridostigmine bromide. In certain embodiments, the compositions of the disclosure can provide extended release of pyridostigmine bromide for at least about 14 hours. The extended release pyridostigmine compositions of the disclosure can include matrix tablets, and pellets suitable for dosing in capsules, sachets, and as sprinkles on food. In certain embodiments, the pyridostigmine compositions can comprise gastroretentive tablet compositions providing extended release of pyridostigmine for at least about 14 hours. In certain embodiments, gastroretentive pyridostigmine compositions of the disclosure are suitable for once-daily administration.

In certain embodiments, the pyridostigmine compositions of the disclosure can be direct compression tablets. The tablets can be made by mixing pyridostigmine bromide, a water-insoluble lipophilic polymer, a filler, a lubricant, and a glidant into a uniform blend; compressing the blend into a tablet core; and coating the tablet core with a functional coat/membrane. In certain embodiments, there can be a seal coat between the tablet core and the functional coat. In certain embodiments, the pyridostigmine compositions of the disclosure can include pyridostigmine granules that are made by hot-melt extrusion. In certain embodiments, the hot-melt extruded pyridostigmine granules can be mixed with extragranular excipients into a uniform blend, and the uniform blend can be compressed into a tablet. In certain embodiments, the matrix tablets can be further coated with an IR drug layer comprising pyridostigmine bromide and a binder, using a perforated pan coater.

In certain embodiments, the pyridostigmine compositions of the disclosure can be gastroretentive tablets. The tablets can be made by mixing pyridostigmine bromide, one or more gas-generating agents, an acid, a wicking agent, a filler, and a glidant into a uniform blend; adding lubricant to the resulting blend and compressing the blend into a tablet core; coating the tablet core with a seal coat comprising aqueous dispersion of hydroxypropyl cellulose; coating the seal-coated tablets with a functional coat comprising a plasticizer, and at least one of ethyl acrylate and methyl methacrylate copolymer (EUDRAGIT® NE, EUDRAGIT® NM), and an ammonio methacrylate copolymer (EUDRAGIT® RL PO, EUDRAGIT® RS PO). In certain embodiments, the functional coat can comprise a plasticizer, and an ammonio methacrylate copolymer (EUDRAGIT® RL PO, EUDRAGIT® RS PO). In certain embodiments, the gastroretentive tablets can be further coated with an IR drug layer comprising pyridostigmine bromide and a binder, using a perforated pan coater.

In certain embodiments, the pyridostigmine compositions of the disclosure can comprise pyridostigmine pellets suitable for dosing in capsules, sachets, and as sprinkles on food. In certain embodiments, the pellets can comprise a pyridostigmine bromide core. In certain embodiments, the pellets can comprise a cellet. In certain embodiments, the pellet cores (e.g., pyridostigmine bromide cores or cellets) are further drug-layered with pyridostigmine bromide. In certain embodiments, the pellets are made by coating the pyridostigmine bromide core with a seal coat comprising a water-soluble hydrophilic polymer; coating the seal-coated pellets with a functional coat comprising a plasticizer, a water-insoluble lipophilic polymer that is insoluble in physiological fluids, and a pore former comprising a water-soluble hydrophilic polymer. In certain embodiments, the pyridostigmine bromide cores are further drug-layered with pyridostigmine bromide.

In certain embodiments, various solvents used in processes of the disclosure include, but are not limited to, water, methanol, ethanol, acetone, isopropyl alcohol, and mixtures thereof. In certain embodiments, the solvent is a mixture of acetone and water, a mixture of ethanol and isopropyl alcohol, a mixture of acetone and isopropyl alcohol, a mixture of isopropyl alcohol and water, or a mixture of water, ethanol, and isopropyl alcohol. In certain embodiments, the solvent is a mixture of acetone and water. In certain embodiments, the ratio of solvent and water ranges from about 70:30 to about 99:1. In certain embodiments, the ratio of acetone and water is about 70:30, about 75:25, about 80:20, about 85:15, about 90:10, about 95:5, or intermediate ranges therein.

6.4. Methods of Treatment

In certain embodiments, the disclosure provides a method for treating myasthenia gravis (MG), postoperative bowel bloating, and urinary retention in a patient. In certain embodiments, the disclosure provides a method for treating or preventing organophosphorus or nerve gas poisoning or injuries. In certain embodiments, the disclosure provides a method for treating dementia, including Alzheimer's disease. The methods comprise administering to a patient or a person in need thereof, an extended release pyridostigmine bromide dosage form of the disclosure. The dosage form is suitable for once- or twice-daily administration. In certain embodiments, the dosage forms of the present disclosure are administered QD as a single dosage unit. In certain embodiments, the compositions of the disclosure are administered QD as multiple dosage units (e.g., two, three, or four dosage units). In certain embodiments, the dose strength and dosing frequency is determined based on the condition being treated and the severity of the condition.

In certain embodiments, the disclosure provides a method for improving patient compliance by administering extended release pyridostigmine bromide dosage forms of the disclosure, wherein the compositions provide an extended release, with no initial dose dumping compared to marketed extended release pyridostigmine products. In certain embodiments, the extended release pyridostigmine dosage forms of the disclosure improve patient compliance by including an IR drug layer that provides a drug plasma concentration sufficient to overcome the lag time in pyridostigmine release seen without application of an IR layer, and sufficient to provide instant therapeutic effects, with reduced or eliminated GI side effects; the extended release component provides controlled extended release of the drug for a period of at least about 14 hours.

In certain embodiments, the disclosure provides a method for improving patient compliance by administering an extended release pyridostigmine bromide dosage forms of the disclosure, wherein the extended release dosage forms will allow for reduced frequency of administration of the composition. In certain embodiments, the dosage forms of the disclosure reduce initial burst release/minimize initial burst release while providing a therapeutically effective amount of pyridostigmine bromide for periods of about 12 hours to about 24 hours.

In certain embodiments, the disclosure provides methods for improving patient compliance by administering, to a patient or a subject in need thereof, an extended release pyridostigmine bromide dosage forms of the disclosure, reducing or minimizing initial burst release of pyridostigmine bromide, and providing the desired therapeutic effect with minimal side effects including nausea, vomiting, diarrhea, abdominal cramps, fasciculations, increased peristalsis, increased salivation, increased bronchial secretions, miosis, and diaphoresis. The methods comprise administering to the patient an extended release pyridostigmine bromide dosage form of the disclosure. The extended release dosage forms of the disclosure are suitable for once- or twice-daily administration.

In certain embodiments, the present disclosure provides for a therapeutic method for treating myasthenia gravis, comprising orally administering to a subject in need thereof a single QD gastroretentive pyridostigmine bromide tablet, wherein the tablet provides an extended release, with minimized initial burst release, of pyridostigmine bromide for up to about 24 hours, and wherein the minimized initial burst release comprises release of not more than 20% of pyridostigmine bromide within two hours of dissolution in a dissolution medium. In certain embodiments, the dissolution medium comprises 50 mM of pH 4.5 acetate buffer with 100 mM NaCl. In certain embodiments, the present disclosure provides for a method for reducing GI side effects in a patient consuming a pyridostigmine composition, the method comprising administering to the patient a gastroretentive pyridostigmine composition comprising an immediate release layer and an extended release component as a single tablet/day, wherein the composition provides an extended release, with a reduced initial burst release, of pyridostigmine bromide for at least about 14 hours, and wherein the reduced initial burst release comprises release of between 20% and 35% of pyridostigmine bromide within two hours of dissolution of the composition into a dissolution medium.

In certain embodiments, the present disclosure provides for a method for improving patient compliance in a patient consuming a pyridostigmine composition, the method comprising administering to the patient a gastroretentive pyridostigmine composition comprising an immediate release layer and an extended release component as a single tablet/day, wherein the composition provides an extended release, with a reduced initial burst release, of pyridostigmine bromide for at least about 14 hours.

7. EXAMPLES

The following examples illustrate the disclosure in a nonlimiting manner. Unless indicated to the contrary, the numerical parameters set forth herein can vary depending upon the desired properties sought to be obtained by the present disclosure.

Example 1

Pyridostigmine Bromide Matrix Tablet Compositions (180 mg)

The present example provides various formulations for pyridostigmine bromide tablets as outlined in Table 1 and Table 2. Seven different tablets were prepared.

TABLE 1

Formulation of Matrix Tablets

| Ingredients | Tablet 1 (mg) | Tablet 2 (mg) | Tablet 3 (mg) | Tablet 4 (mg) | Tablet 5 (mg) |
|---|---|---|---|---|---|
| Pyridostigmine bromide | 180.0 | 180.0 | 180.0 | 180.0 | 180.0 |
| Stearic acid | — | 180.0 | — | 20.00 | 20.00 |
| Carnauba wax | — | — | — | 160.00 | 80.00 |
| Ethylcellulose (ETHOCEL ™) | — | — | — | — | — |
| Silicon dioxide (SYLOID ® 244FP) | 180.0 | — | 180.0 | — | 80.00 |
| Fumed silica (CAB-O-SIL ®) | — | 20.00 | 20.00 | 20.00 | 20.00 |
| Mannitol (PARTECK ® M200 | 100.0 | 100.0 | 100.0 | 100.0 | 100.0 |
| Magnesium stearate | 5.00 | 5.00 | 5.00 | 5.00 | 5.00 |
| Core Tablet Weight | 465.0 | 485.0 | 485.0 | 485.0 | 485.0 |
| Functional Coat | | | | | |
| Cellulose acetate | 40.40 | 41.73 | 41.73 | 41.73 | 41.73 |
| Polyethylene glycol (PEG 3350) | 2.02 | 2.08 | 2.08 | 2.08 | 2.08 |
| Methylcellulose (METHOCEL ™ E5) | 4.004 | 4.173 | 4.173 | 4.173 | 4.173 |
| Solvent* acetone:water (95:5) q.s. | | | | | |
| Total Tablet Weight | 511.42 | 532.98 | 532.98 | 532.98 | 532.98 |

*Removed during process

TABLE 2

Formulation of Matrix Tablets

| Ingredients | Tablet 6** (mg) | Tablet 7 (mg) |
|---|---|---|
| Pyridostigmine bromide | 150.00 | 180.00 |
| Stearic acid | — | 90.00 |
| Ethylcellulose (ETHOCEL ™) | 100.00 | — |
| Silicon dioxide (SYLOID ® 244FP) | 20.00 | — |
| Fumed silica | — | 10.00 |

TABLE 2-continued

Formulation of Matrix Tablets

| Ingredients | Tablet 6** (mg) | Tablet 7 (mg) |
|---|---|---|
| (CAB-O-SIL ®) | | |
| Mannitol (PARTECK ®M200) | 100.00 | 100.00 |
| Magnesium stearate | 5.00 | 5.00 |
| Core Tablet Weight | 375.00 | 385.00 |
| Functional Coat | | |
| Cellulose acetate | 62.50 | 33.40 |
| Polyethylene glycol (PEG 3350) | 6.25 | 1.67 |
| Methylcellulose (METHOCEL™ E5) | 6.25 | 3.34 |
| Solvent* acetone:water (95:5) q.s. | | |
| Total Weight | 450.00 | 423.41 |

*Removed during process
**Tablet 6 can have an IR coat of 30 mg of pyridostigmine bromide Tablets 1-5 and Tablet 7 contain 180 mg of pyridostigmine bromide and include 10% coating weight gain of uncoated tablet. Tablets 1-5 and 6 do not contain ethylcellulose. Tablet 6 contains 150 mg of pyridostigmine bromide, ethylcellulose, and 20% coating weight gain of uncoated tablet. Tablets 1-7 were made according to the following general procedure.

Manufacturing Procedure:
1. A uniform blend of pyridostigmine, stearic acid, carnauba wax, ethylcellulose, silicon dioxide, fumed silica, mannitol, and magnesium stearate was made as per Tablets 1-7.
2. For each blend, the drug and the excipients were taken in a V-blender and mixed to obtain a uniform blend.
3. Magnesium stearate was sieved through sieve #30 and mixed with the uniform blend from step #2.
4. Required amount of blend was filled into the die and then compressed as tablet compositions.
5. Cellulose acetate and methylcellulose were added to a stainless steel container charged with an acetone and water mixture in a ratio of 95:5 and mixed to obtain a clear solution.
6. Polyethylene glycol 3350 was added to the solution from step #4 and mixed for not less than about 30 minutes.
7. The tablets from step #4 were taken in a coating pan and coated with the solution from step #6 until the target weight gain was attained.

FIG. 2 depicts a schematic representation of pyridostigmine matrix tablets, with and without an immediate release drug layer.

Example 2

Pyridostigmine Bromide Gastroretentive Tablet Compositions

The present Example provides various formulations for pyridostigmine bromide gastroretentive tablets as outlined in Table 3.

TABLE 3

Formulation of Pyridostigmine Bromide Tablets

| Ingredients | Tablet 8 (mg/dose) | Tablet 9 (mg/dose) | Tablet 10 (mg/dose) | Tablet 11 (mg/dose) | Tablet 12 (mg/dose) |
|---|---|---|---|---|---|
| Pyridostigmine bromide | 180.0 | 180.0 | 180.0 | 135.0 | 135.0 |
| Succinic acid, NF-micronized | 50.0 | 50.0 | 50.0 | 80.0 | 80.0 |
| Sodium bicarbonate | 50.00 | 50.0 | 50.0 | 55.0 | 55.0 |
| Calcium carbonate | 125.0 | 125.0 | 125.0 | 65.0 | 65.0 |
| Crospovidone | 100.0 | 100.0 | 100.0 | 200.0 | 100.0 |
| PARTECK ® M200 | 233.0 | 233.0 | 233.0 | 153.0 | 253.0 |
| BENECEL™ K4M PH DC | 200.0 | 300.0 | 200.0 | — | 100.0 |
| BENECEL™ K200M | — | — | 25.0 | — | — |
| METHOCEL™ K100 Prem LVCR | — | — | — | 300.0 | 200.0 |
| CAB-O-SIL ® | 4.00 | 4.00 | 4.00 | 4.00 | 4.00 |
| Magnesium stearate | 8.00 | 8.00 | 8.00 | 8.00 | 8.00 |
| Total weight | 950.0 | 1050.0 | 975.0 | 1000.0 | 1000.0 |
| Seal Coat | | | | | |
| Hydroxypropyl cellulose | 33.33 | 33.33 | 33.33 | — | — |
| Talc | 3.33 | 3.33 | 3.33 | — | — |
| Triethyl citrate | 3.33 | 3.33 | 3.33 | — | — |
| Solvent* acetone:water (95:5) | q.s. | q.s. | q.s. | q.s. | q.s. |
| Functional Coat | | | | | |
| EUDRAGIT ® RL PO | 148.15 | 148.15 | 148.15 | 148.15 | 148.15 |
| Triethyl citrate | 22.22 | 22.22 | 22.22 | 22.22 | 22.22 |
| Talc | 29.63 | 29.63 | 29.63 | 29.63 | 29.63 |
| Solvent* acetone:water (95:5) | q.s. | q.s. | q.s. | q.s. | q.s. |

TABLE 3-continued

Formulation of Pyridostigmine Bromide Tablets

| Ingredients | Tablet 8 (mg/dose) | Tablet 9 (mg/dose) | Tablet 10 (mg/dose) | Tablet 11 (mg/dose) | Tablet 12 (mg/dose |
|---|---|---|---|---|---|
| Over Coat | | | | | |
| OPADRY ® white | 15.00 | 15.00 | 15.00 | — | — |
| Solvent*Purified water, USP | q.s. | q.s. | q.s. | | |
| Total weight | 1205.00 | 1305.00 | 1230.00 | 1200.0 | 1200.0 |

*Removed during process

Tablets 8-10 contain 180 mg of pyridostigmine, 50 mg of succinic acid, 50 mg of sodium bicarbonate, 125 mg of calcium carbonate, and BENECEL™ K4M-DC. Tablet 10 further contains BENECEL™ 200M. Tablets 11-12 contain 135 mg of pyridostigmine bromide, and 80 mg of succinic acid, 55 mg of sodium bicarbonate, and 65 mg of calcium carbonate. Further, Tablet 11 contains METHOCEL™ K100 Premium LVCR and Tablet 12 contains a mixture of METHOCEL™ K100 Premium LVCR and BENECEL™ K4M PH DC. Tablets 8-12 were made according to the following general procedure.

Manufacturing Procedure:

A. Core Tablets
1. Pyridostigmine, succinic acid, sodium bicarbonate, calcium carbonate, crospovidone, PARTECK® M200, BENECEL™ K4M-DC, BENECEL™ K200M, METHOCEL™ K100 Premium LVCR, and CAB-O-SIL®, as per Tablets 8-12, were sieved through sieve #20 and mixed to obtain a uniform blend.
2. Magnesium stearate was sieved through sieve #30 and mixed with the uniform blend from step #1.
3. The resulting blend from step #2 was compressed to obtain pyridostigmine tablet cores.

B. Seal Coating
1. Hydroxypropyl cellulose, triethyl citrate, and talc were added to a mixture of acetone and water (95:5) in a stainless steel container and mixed to form a uniform dispersion.
2. Tablet cores 8-10 were seal coated using a perforated pan coater with an inlet air temperature of 25° C.-60° C. at a product temperature of 25-45° C.
3. The coated tablet cores were dried in the coating pan.

C. Functional Coating and Over Coat
1. EUDRAGIT® RL PO was added to acetone and water mixture (95:5) and mixed to obtain a clear solution.
2. To the solution from step #1, triethyl citrate was added and mixed for at least 45 minutes.
3. To the solution from step #2, talc was added and mixed for at least 60 minutes to obtain a homogeneous dispersion.
4. The homogeneous dispersion from step #3 was sprayed onto the seal coated tablet cores 8-10 and tablet cores without seal coat, e.g., Tablet cores 11-12.
5. The coated tablets from step #4 were dried in a coating pan.
6. An orifice was laser drilled in the coated tablets from step #5 such that the orifice passed through various coating layers.
7. Weighed quantity of opadry white was added into the required amount of purified water. The suspension was mixed until a uniform dispersion was formed.
8. The functional coated tablets from step #6 were further coated with the dispersion from step #7 in a perforated coating pan with inlet air temperature at 25°-45° C.
9. The coated tablets from step #8 were dried in a pan to a moisture content below 3.0%, as measured by loss on drying at 105° C.

FIG. 4 provides a comparison of dissolution profiles of pyridostigmine bromide gastroretentive Tablets 8, 9 and 10, using USP I-custom basket-dissolution apparatus, in pH 4.5 acetate buffer, at 100 RPM. FIG. 4 demonstrates that Tablets 8-10 provide extended release, with minimized initial burst release, of pyridostigmine bromide for a period of about 22 hours.

Example 3

Pyridostigmine Bromide Pellet Composition Comprising Pyridostigmine Bromide Granule Core The present Example provides for a pyridostigmine bromide pellet composition comprising a pyridostigmine bromide core as outlined in Table 4.

TABLE 4

Formulation of Pyridostigmine Bromide Pellet

| Ingredients | Pellet 1 mg/dose |
|---|---|
| Pyridostigmine bromide granules | 180.00 |
| Seal Coat | |
| Hydroxypropyl cellulose (KLUCEL ™) | 15.00 |
| Talc | 3.00 |
| Functional coat | |
| Ethyl cellulose (ETHOCEL ™ 20 cp) | 30.40 |
| Triethyl citrate | 3.00 |
| Talc | 3.00 |
| METHOCEL ™ E5 Premium LV | 3.00 |
| Solvent* ethanol:water (90:10) q.s. | |
| Total Weight | 237.40 |

*Removed during process

Pellet 1 contains pyridostigmine bromide granule as pellet core, and a functional coat comprising ETHOCEL™ 20 cp, METHOCEL™ E5 Premium LV, and triethyl citrate. Pellet 1 was made according to the following general procedure.

Manufacturing Procedure:

A. Seal Coating
1. Hydroxypropyl cellulose was added to dehydrated alcohol in a stainless steel container and mixed to form a uniform solution.

2. To the dispersion from step #1, the purified water was added and mixed until a clear solution formed.
3. To the solution from step #2, talc was added and mixed for not less than about 30 minutes to form a homogenous dispersion.
4. Pyridostigmine bromide granules were coated using a Wurster fluid bed coater with an inlet air temperature of 30-50° C., and sufficient air volume for fluidization. When the product temperature reached 30° C., the dispersion from step #3 was sprayed onto the granules while maintaining the product temperature of 25-35° C. and sufficient air volume for the fluidization, until the target coating weight gain was achieved.

B. Functional Coating
1. Ethyl cellulose and METHOCEL™ E5 Premium LV were added to dehydrated alcohol in a stainless steel container and mixed for about 1 hour to form a uniform dispersion.
2. To the dispersion from step #1, water was added and mixed to obtain a homogeneous dispersion.
3. To the dispersion from step #2, TEC was added and mixed for not less than about 15 minutes.
4. To the dispersion from step #3, talc was added and mixed for not less than about 30 minutes to obtain a uniform dispersion.
5. Seal coated pyridostigmine bromide granules (procedure A, above) were taken in a Wurster chamber and coated with the dispersion from step #4, until target coating weight gain was achieved.

Example 4

Pyridostigmine Bromide Pellet Composition Comprising Pyridostigmine Bromide Granule Core and Drug Layer containing Pyridostigmine Bromide The present Example provides for a pyridostigmine bromide pellet composition comprising a pyridostigmine bromide granule core and a drug layer containing pyridostigmine bromide. Two different pellets were prepared as outlined in Table 5.

TABLE 5

Formulation of Pyridostigmine Bromide Pellet

| Ingredients | Pellet 2 mg/dose | Pellet 3 mg/dose |
| --- | --- | --- |
| Pyridostigmine bromide granules | 78.16 | 78.16 |
| Drug Layer | | |
| Pyridostigmine bromide | 101.84 | 101.84 |
| METHOCEL ™ E5 Premium LV | 20.36 | 20.36 |
| Talc | 4.07 | 4.07 |
| Solvent* ethanol:water (85:15) q.s. | | |
| Seal Coat | | |
| Hydroxypropyl cellulose (KLUCEL ™ LF) | 17.04 | 17.04 |
| Talc | 3.40 | 3.40 |
| Solvent* acetone:water(95:5) q.s. | | |
| Functional Coat | | |
| Ethyl cellulose (ETHOCEL ™ 20 cp) | 56.20 | — |
| Ethyl cellulose (ETHOCEL ™ 45 cp) | — | 74.90 |
| Triethyl citrate | 5.60 | 7.50 |
| Talc | 5.60 | 7.50 |
| Solvent* ethanol:water (90:10) q.s. | | |
| Total Weight | 292.27 | 314.77 |

*Removed during process

Pellets 2 and 3 contain pyridostigmine bromide granules as pellet core and a pyridostigmine bromide drug layer over the pellet core. Pellet 2 contains 30 wt % functional coat, of the seal coated pellet core, and Pellet 3 contains 40 wt % functional coat, of the seal coated pellet core. Pellets 2 and 3 were made according to the following general procedure.

Manufacturing Procedure:

A. Drug Layering
1. Pyridostigmine bromide and METHOCEL™ E5 Premium LV were added to a mixture of ethanol and water (85:15) and mixed for not less than about 60 minutes to obtain a solution.
2. To the solution from step #1, talc was added and mixed for not less than about 30 minutes to obtain a uniform dispersion.
3. Pyridostigmine bromide granules were coated using a Wurster fluid bed coater, with an inlet air temperature of about 30-50° C., and sufficient air volume for fluidization.
4. When the product temperature reached 30° C., the dispersion from step #3 was sprayed onto the pyridostigmine bromide granules while maintaining the product temperature of 25-35° C. and sufficient air volume for the fluidization, until the target coating weight gain was achieved.

B. Seal Coating
1. Hydroxypropyl cellulose was added to acetone in a stainless steel container and mixed to form a uniform solution.
2. To the solution from step #1, the purified water was added and mixed until a clear solution was obtained.
3. To the solution from step #2, talc was added and mixed for not less than about 30 minutes to form a homogenous dispersion.
4. Pyridostigmine granules were coated using a Wurster fluid bed coater with an inlet air temperature of 30-50° C., and sufficient air volume for fluidization. When the product temperature reached 30° C., the dispersion from step #3 was sprayed onto the granules while maintaining the product temperature of 28-30° C. and sufficient air volume for the fluidization, until the target coating weight gain was achieved.

C. Functional Coating
1. ETHOCEL™ 20 cp/ETHOCEL™ 45 cp were added to dehydrated alcohol in a stainless steel container and mixed for not less than about 60 minutes to obtain a uniform dispersion.
2. To the dispersion from step #1, water was added and mixed for not less than about 30 minutes to obtain a homogeneous dispersion.
3. To the dispersion from step #2, TEC was added and mixed for not less than about 45 minutes.
4. To the dispersion from step #3, talc was added and mixed for not less than about 15 minutes to obtain a uniform dispersion.
5. Seal coated pyridostigmine granules (procedure B) were taken in a Wurster chamber and coated with the dispersion from step #4, until target coating weight gain was achieved.

FIG. 1 depicts a schematic representation of pyridostigmine pellets, with and without an immediate release drug layer.

FIG. 5 compares dissolution profiles of pyridostigmine bromide Pellets 2 and 3, using USP Apparatus II, in 50 mM of pH 6.8 phosphate buffer. FIG. 5 demonstrates that pellets containing pyridostigmine bromide granules as pellet core provide fast drug release, irrespective of their functional coat weight gain.

Example 5

Pyridostigmine Bromide Pellet Composition Comprising Cellet Core

The present Example provides for pyridostigmine bromide pellet compositions comprising cellet cores. Eight different pellets, as outlined in Tables 6, 7, and 8, were prepared.

TABLE 6

Formulation of Pyridostigmine Bromide Pellets

| Ingredients | Pellet 4 mg/dose | Pellet 5 mg/dose | Pellet 6 mg/dose |
| --- | --- | --- | --- |
| Cellet core (350 μm) | 100.00 | 100.00 | 100.00 |
| Drug Layer | | | |
| Pyridostigmine bromide | 150.00 | 150.00 | 150.00 |
| ETHOCEL ® Standard 20 Premium | 30.00 | 30.00 | 30.00 |
| Dibutyl Sebacate (DBS) | 3.00 | 3.00 | 3.00 |
| Talc | 6.00 | 6.00 | 6.00 |
| Solvent* ethanol:water (90:10) q.s. | | | |
| Seal coat | | | |
| METHOCEL ™ E5 Premium LV | 72.05 | 72.05 | 72.05 |
| Talc | 14.41 | 14.41 | 14.41 |
| Solvent* acetone:water (95:5) | NA | NA | NA |
| Functional coat | | | |
| ETHOCEL ® Standard 20 Premium | 44.90 | 112.2 | — |
| Dibutyl sebacate | 9.00 | 22.40 | — |
| Talc | 6.70 | 16.86 | — |
| CAB-O-SIL ® | 1.10 | 2.80 | — |
| Cellulose acetate (CA-398-10NF/EP) | — | — | 89.70 |
| PEG 3350 | — | — | 17.90 |
| METHOCEL ™ E5 Premium LV | — | — | 13.50 |
| Solvent* ethanol:water (90:10) | q.s. | q.s. | q.s. |
| Total Weight | 437.16 | 529.72 | 496.56 |

*Removed during process

TABLE 7

Formulation of Pyridostigmine Bromide Pellets

| Ingredients | Pellet 7 mg/dose | Pellet 8 mg/dose |
| --- | --- | --- |
| Cellet core (350 μm) | 100.00 | 100.00 |
| Drug Layer | | |
| Pyridostigmine bromide | 150.00 | 150.00 |
| ETHOCEL ® Standard 20 Premium | 30.00 | 30.00 |
| Dibutyl sebacate (DBS) | 3.00 | 3.00 |
| Talc | 6.00 | 6.00 |
| Solvent* ethanol:water (90:10) q.s. | | |
| Seal coat | | |
| METHOCEL ™ E5 Premium LV | 16.20 | 16.20 |
| Talc | 3.20 | 3.20 |
| Solvent* acetone:water (95:5) q.s. | | |
| Functional coat | | |
| ETHOCEL ® Standard 20 Premium | 52.30 | 83.60 |
| Dibutyl sebacate | 10.50 | 16.80 |
| Talc | 7.80 | 12.50 |

TABLE 7-continued

Formulation of Pyridostigmine Bromide Pellets

| Ingredients | Pellet 7 mg/dose | Pellet 8 mg/dose |
| --- | --- | --- |
| METHOCEL ™ E5 Premium LV | 5.20 | 8.40 |
| CAB-O-SIL ® | 1.30 | 3.10 |
| Solvent* Acetone:Water (90:10) q.s. | | |
| Total Weight | 385.50 | 432.80 |

*Removed during process

TABLE 8

Formulation of Pyridostigmine Bromide Pellets

| Ingredients | Pellet 9 mg/dose | Pellet 10 mg/dose | Pellet 11 mg/dose |
| --- | --- | --- | --- |
| Cellet core (350/500 μm) | 100.0 | 100.0 | 100.0 |
| Drug Layer | | | |
| Pyridostigmine bromide | 180.0 | 180.0 | 180.0 |
| ETHOCEL ® Standard 20 Premium | 36.00 | 36.00 | 36.00 |
| Talc | 7.20 | 7.20 | 7.20 |
| Dibutyl Sebacate (DBS) | 3.60 | 3.60 | 3.60 |
| Solvent* ethanol:water (90:10) q.s. | | | |
| Seal Coat | | | |
| METHOCEL ™ E5 Premium LV | 19.06 | 19.06 | 19.06 |
| Talc | 3.82 | 3.82 | 3.82 |
| Solvent* acetone:water (95:5) q.s. | | | |
| Functional Coat | | | |
| ETHOCEL ® Standard 20 Premium | 56.20 | 74.94 | 99.91 |
| Dibutyl Sebacate | 11.24 | 14.99 | 19.98 |
| Talc | 8.43 | 11.24 | 14.98 |
| METHOCEL ™ E5 Premium LV | 1.40 | 1.87 | 2.50 |
| CAB-O-SIL ® | 1.40 | 1.87 | 2.50 |
| Solvent* ethanol:water (90:10) q.s. | | | |
| Total Weight | 428.35 | 454.59 | 489.55 |

*Removed during process

Pellets 4-11 contain a cellet core coated with a drug layer containing pyridostigmine bromide and a functional coat over the drug layer; Pellets 4 and 5 contain a functional coat comprising ETHOCEL® Standard 20 Premium, dibutyl sebacate, talc, and CAB-O-SIL®; Pellet 6 contains a cellet core and a functional coat comprising cellulose acetate 398, polyethylene glycol, and METHOCEL™ E5 Premium LV; and Pellets 7-11 contain functional coat comprising ETHOCEL® Standard 20 Premium, dibutyl sebacate, talc, METHOCEL™ E5 Premium LV, and CAB-O-SIL®. Pellets 4-11 were made according to the following general procedure.

Manufacturing Procedure:

A. Drug Layering

1. Pyridostigmine bromide and ETHOCEL® Standard 20 Premium were added to a mixture of ethanol and water (90:10) and mixed for not less than about 60 minutes to obtain a solution, followed by addition of dibutyl sebacate.
2. To the solution from step #1, talc was added and mixed for not less than about 30 minutes to obtain a uniform dispersion.
3. Cellet core was coated using a Wurster fluid bed coater, with an inlet air temperature of about 25-50° C., and sufficient air volume for fluidization. When the product temperature reached 30° C., the dispersion from step #2 was sprayed onto the cellets while maintaining the product temperature of 25-30° C. and sufficient air volume for the fluidization, until the target coating weight gain was achieved.

B. Seal Coating

1. METHOCEL™ E5 Premium LV was added to a mixture of acetone and water (95:5) in a stainless steel container and mixed to form a uniform solution.
2. To the solution from step #2, talc was added and mixed for not less than about 30 minutes to obtain a homogeneous dispersion.
3. Pyridostigmine bromine drug-layered granules (procedure A) were coated using Wurster fluid bed coater with an inlet air temperature of 30-50° C., and sufficient air volume for fluidization. When the product temperature reached 30° C., the dispersion from step #2 was sprayed onto the drug-layered granules while maintaining the product temperature of about 28° C. and sufficient air volume for the fluidization, until the target coating weight gain was achieved.

C. Functional Coating

1. ETHOCEL® Standard 20 Premium or cellulose acetate 398 (as per Pellets 4-11) was added to dehydrated alcohol and water or acetone and water mixture in a stainless steel container and mixed for not less than about 60 minutes to obtain a uniform solution.
2. To the solution from step #1, METHOCEL™ E5 Premium LV, and DBS/PEG were added and mixed until a clear solution was formed.
3. To the dispersion from step #2, talc and CAB-O-SIL® were added, and mixed for not less than about 30 minutes to obtain a uniform dispersion.
4. Seal coated pyridostigmine pellets (Step B) were taken in a Wurster chamber and coated with the dispersion from step #3, until target coating weight gain was achieved.

FIG. 6 compares dissolution profiles of pyridostigmine bromide Pellets 9-11, using USP Apparatus II (Paddle), at about 50 rpm and about 37° C., in 50 mM of pH 6.8 phosphate buffer.

FIG. 6 demonstrates that Pellets 10 and 11, containing higher functional coat weight gain, provide better controlled release of pyridostigmine bromide for a period of about 22 hours.

Example 6

Effect of the Presence of Orifice in Functional Coat on Release Rate of Gastroretentive Pyridostigmine Compositions The present Example provides for comparison of dissolution profiles of tablets comprising pyridostigmine bromide. Three different tablets were prepared as outlined in Table 9. Tablets were made with and without an orifice in the functional coat to evaluate the effect an orifice has on dissolution profiles.

TABLE 9

Formulation of Pyridostigmine Bromide Gastroretentive Tablets

| Ingredients | Tablet 8 (mg/dose) | Tablet 13 (mg/dose) | Tablet 14 (mg/dose) |
|---|---|---|---|
| Tablet Core | | | |
| Pyridostigmine bromide | 180.0 | 135.0 | 135.0 |
| Succinic acid | 50.0 | 80.0 | 80.0 |
| Sodium bicarbonate | 50.0 | 55.0 | 55.0 |

TABLE 9-continued

Formulation of Pyridostigmine Bromide Gastroretentive Tablets

| Ingredients | Tablet 8 (mg/dose) | Tablet 13 (mg/dose) | Tablet 14 (mg/dose) |
|---|---|---|---|
| Calcium carbonate | 125.0 | 65.0 | 65.0 |
| Crospovidone | 100.0 | 100.0 | 100.0 |
| PARTECK® M200 (D-mannitol) | 233.0 | 253.0 | 253.0 |
| BENECEL™ K4M PH DC | 200.0 | — | 150.0 |
| METHOCEL™ K100 Prem LVCR | — | 300.0 | 150.0 |
| CAB-O-SIL® | 4.00 | 4.00 | 4.00 |
| Magnesium stearate | 8.00 | 8.00 | 8.00 |
| Total Weight | 950.0 | 1000.0 | 1000.0 |
| Seal Coat | | | |
| Hydroxypropyl cellulose | 33.33 | — | — |
| Talc | 3.33 | — | — |
| Triethyl citrate | 3.33 | — | — |
| Solvent* acetone:water (95:5) | q.s. | — | — |
| Functional Coat | | | |
| EUDRAGIT® RL PO | 148.15 | 148.15 | 148.15 |
| Triethyl citrate | 22.22 | 22.22 | 22.22 |
| Talc | 29.63 | 29.63 | 29.63 |
| Solvent* acetone:water (95:5) | q.s. | q.s. | q.s. |
| Over Coat | | | |
| OPADRY® white | 15.0 | — | — |
| Solvent*Purified water, USP | q.s. | — | — |
| Total Weight | 1205.0 | 1200.0 | 1200.0 |

*Removed during process

Tablet 8 contains 180 mg of pyridostigmine, 50 mg of succinic acid, 50 mg of sodium bicarbonate, 125 mg of calcium carbonate, and BENECEL™ K4M-DC. Tablets 13 and 14 contain 135 mg of pyridostigmine bromide, 80.0 mg of succinic acid, 55.0 mg of sodium bicarbonate, and 65.0 mg of calcium carbonate. Further, Tablet 13 contains METHOCEL™ K100 Prem LVCR and Tablet 14 contains a mixture of METHOCEL™ K100 Prem LVCR and BENECEL™ K4M-DC. Tablets 8, 13 and 14, each containing an orifice in fluid communication with the pull layer, were made according to the procedure as per Example 2, and without a seal coat step for Tablets 13 and 14. FIG. 7 compares dissolution profiles of Tablets 8, 13 and 14 in about 900 ml of pH 5.0 acetate buffer containing 150 mM NaCl, using USP Apparatus I (Custom Basket), at 100 rpm and 37° C. FIG. 7 shows that Tablets 13 and 14 provide 10-15% slower drug release compared to Tablet 8.

FIG. 8 compares dissolution profiles, of Tablets 13 and 14 containing an orifice/hole in the membrane/functional coat and Tablets 13 and 14 without orifice/hole in the membrane/functional coat. The dissolution testing was conducted in about 250 ml of pH 3.0 dissolution media containing about 100 mM NaCl, using USP Apparatus III (BIO-DIS), at 25 dpm and 37° C. FIG. 8 demonstrates that Tablets 13 and 14 without any orifice/hole in the functional coat provided reduced drug recovery compared to the Tablets 8, 13, and 14 containing an orifice/hole in the functional coat.

Example 7

Effect of Coating level of Functional Coat and Presence of Orifice/Hole in the Functional Coat on Release Rate of Gastroretentive Pyridostigmine Compositions The present Example provides for comparison of dissolution profiles of tablets comprising pyridostigmine bromide and various functional coating compositions. Three different tablets, as outlined in Table 10, were prepared. The tablets were tested with and without an orifice/in their functional coat.

TABLE 10

Formulation of Pyridostigmine Bromide Tablets

| Ingredients | Tablet 8 (mg/dose) | Tablet 14 (mg/dose) | Tablet 14A (mg/dose) |
|---|---|---|---|
| Tablet Core | | | |
| Pyridostigmine bromide | 180.0 | 135.0 | 135.0 |
| Succinic acid | 50.0 | 80.0 | 80.0 |
| Sodium bicarbonate | 50.0 | 55.0 | 55.0 |
| Calcium carbonate | 125.0 | 65.0 | 65.0 |
| Crospovidone | 100.0 | 100.0 | 100.0 |
| PARTECK ® M200 | 233.0 | 253.0 | 253.0 |
| BENECEL ™ K4M PH DC | 200.0 | — | 150.0 |
| METHOCEL ™ K100 Prem LVCR | — | 300.0 | 150.0 |
| CAB-O-SIL ® | 4.0 | 4.00 | 4.00 |
| Magnesium stearate | 8.0 | 8.00 | 8.00 |
| Total Weight | 950.0 | 1000.0 | 1000.0 |
| Seal Coat | | | |
| Hydroxypropyl Cellulose | 33.33 | — | — |
| Talc | 3.33 | — | — |
| Triethyl citrate | 3.33 | — | — |
| Solvent* acetone:water (95:5) | q.s. | — | — |
| Functional Coat | | | |
| EUDRAGIT ® RL PO | 148.15 | 148.15 | 185.18 |
| Triethyl citrate | 22.22 | 22.22 | 27.77 |
| Talc | 29.63 | 29.63 | 37.03 |
| Solvent* acetone:water (95:5) | q.s. | q.s. | q.s. |
| Total Weight | 1190.0 | 1200.0 | 1250.0 |

*Removed during process

Tablets 8 and 14 contain 200 mg coating weight gain of the functional coat and Tablet 14A contains 250 mg coating weight gain of the functional coat. Tablets 8, 14, and 14A were made according to the procedure as per Example 2 (and without a seal coat step for Tablets 14 and 14A). FIG. 9 compares dissolution profiles, of Tablets 8, 14, and 14A containing an orifice/hole in the functional coat and Tablets 14 and 14A without orifice/hole in the functional coat. The dissolution testing was conducted in about 900 ml of pH 5.0 acetate buffer containing 150 mM NaCl, using USP Apparatus I (Custom Basket), at 100 rpm and 37° C. FIG. 9 demonstrates that coating weight gain has no significant effect on release rate of the tablets. The figure further demonstrates that tablets with orifice/hole provided higher release rate compared to tablets without orifice/hole.

Example 8

Effect of Coating Level of Functional Coat and Presence of an Orifice/Hole in the Functional Coat on Floating Lag Time and Volume Expansion of Gastroretentive Pyridostigmine Compositions The present example provides for evaluation of floating lag time and volume expansion of various tablets comprising pyridostigmine bromide. Eight different tablets, as outlined in Tables 11 and 12, were prepared with various levels of functional coating. The tablets were tested with and without an orifice in their functional coats.

TABLE 11

Formulation of Pyridostigmine Bromide Tablets

| Ingredients | Tablet 8 (mg/dose) | Tablet 8A (mg/dose) | Tablet 11 (mg/dose) | Tablet 11A (mg/dose) |
|---|---|---|---|---|
| Tablet Core | | | | |
| Pyridostigmine bromide | 180.0 | 180.0 | 135.0 | 135.0 |
| Succinic acid | 50.0 | 50.0 | 80.0 | 80.0 |
| Sodium bicarbonate | 50.0 | 50.0 | 55.0 | 55.0 |
| Calcium carbonate | 125.0 | 125.0 | 65.0 | 65.0 |
| Crospovidone | 100.0 | 100.0 | 200.0 | 200.0 |
| PARTECK ® M200 | 233.0 | 233.0 | 153.0 | 253.0 |
| BENECEL ™ K4M PH DC | 200.0 | 200.0 | — | 150.0 |
| METHOCEL ™ K100 PREM LVCR | — | — | 300.0 | 150.0 |
| CAB-O-SIL ® | 4.00 | 4.00 | 4.00 | 4.00 |
| Magnesium stearate | 8.00 | 8.00 | 8.00 | 8.00 |
| Total Weight | 950.0 | 950.0 | 1000.0 | 1000.0 |
| Seal Coat | | | | |
| Hydroxypropyl cellulose | 33.33 | 33.33 | — | — |
| Talc | 3.33 | 3.33 | — | — |
| Triethyl citrate | 3.33 | 3.33 | — | — |
| Solvent* acetone:water (95:5) | q.s. | q.s. | — | — |
| Functional Coat | | | | |
| EUDRAGIT ® RL PO | 148.15 | 185.18 | 148.15 | 185.18 |
| Triethyl citrate | 22.22 | 27.77 | 22.22 | 27.77 |
| Talc | 29.63 | 37.03 | 29.63 | 37.03 |
| Solvent* acetone:water (95:5) | q.s. | q.s. | q.s. | q.s. |
| Over Coat | | | | |
| Opadry white | 15.0 | 15.0 | — | — |
| Total Weight | 1205.0 | 1255.0 | 1200.0 | 1250.0 |

*Removed during process

TABLE 12

Formulation of Pyridostigmine Bromide Tablets

| Ingredients | Tablet 13 (mg/dose) | Tablet 13A (mg/dose) | Tablet 15 (mg/dose) | Tablet 15A (mg/dose) |
|---|---|---|---|---|
| Tablet Core | | | | |
| Pyridostigmine bromide | 135.0.0 | 135.0 | 135.0 | 135.0 |
| Succinic acid | 80.0 | 80.0 | 125.0 | 125.0 |
| Sodium bicarbonate | 55.0 | 55.0 | 75.0 | 75.0 |
| Calcium carbonate | 65.0 | 65.0 | 100.0 | 100.0 |
| Crospovidone | 100.0 | 100.0 | 200.0 | 200.0 |
| PARTECK ® M200 | 253.0 | 253.0 | 153.0 | 153.0 |
| BENECEL ™ K4M PH DC | — | — | 100.0 | 100.0 |
| METHOCEL ™ K100 Prem LVCR | 300.0 | 300.0 | 100.0 | 100.0 |
| CAB-O-SIL ® | 4.00 | 4.00 | 4.00 | 4.00 |
| Magnesium stearate | 8.00 | 8.00 | 8.00 | 8.00 |
| Total Weight | 1000.0 | 1000.0 | 1000.0 | 1000.0 |
| Functional Coat | | | | |
| EUDRAGIT ® RL PO | 148.15 | 185.18 | 148.15 | 185.18 |
| Triethyl citrate | 22.22 | 27.77 | 22.22 | 27.77 |
| Talc | 29.63 | 37.03 | 29.63 | 37.03 |
| Solvent* acetone:water (95:5) | q.s. | q.s. | q.s. | q.s. |
| Total Weight | 1200.0 | 1250.0 | 1200.0 | 1250.0 |

*Removed during process

Tablets 8 and 8A contain 180 mg of pyridostigmine bromide, 50 mg of succinic acid, 50 mg of sodium bicarbonate, 125 mg of calcium carbonate, and a seal coat. Tablets 11 and 11A contain 135 mg of pyridostigmine bromide, 80 mg of succinic acid, 55 mg of sodium bicarbonate, and 65 mg of calcium carbonate. Tablets 13 and 13A contain 135 mg of pyridostigmine bromide, 80 mg of succinic acid, 55 mg of sodium bicarbonate, and 65 mg of calcium carbonate. Tablets 15 and 15A contain 135 mg of pyridostigmine bromide, 125 mg of succinic acid, 75 mg of sodium bicarbonate, and 100 mg of calcium carbonate. Tablets 8/8A and Tablets 13/13A contain 100 mg of crospovidone, and Tablets 11/11A and tablets 15/15A contain 200 mg of crospovidone. Tablets 8, 8A, 11, 11A, 13, 13A, 15, and 15A were made according to the procedure as per Example 2 (and without a seal coat step for Tablets 11, 11A, 13, 13A, 15, and 15A). FIG. 10 compares floating lag time of Tablets 8, 11, 13, and 15, with and without orifice/hole, at 200 mg functional coating weight gain, and Tablets 8A, 11A, 13A, and 15A, with and without orifice/hole, at 250 mg functional coating weight gain. The flotation studies were performed, using Rotating Bottle method at 5 rpm and 37° C., in 200 ml of a dissolution medium with pH 4.5 acetate buffer containing 100 mM NaCl. The figure demonstrates that tablets with 200 mg functional coating weight gain exhibit shorter lag time compared to tablets with 250 mg functional coating weight gain. The figure further demonstrates that Tablets 8/8A containing a seal coat exhibit longer floating lag time compared to tablets without a seal coat (Tablets 11/11A, 13/13A, and 15/15A).

FIG. 11 compares volumetric expansion at flotation of Tablets 8, 11, 13, and 15, with and without orifice/hole, at 200 mg functional coating weight gain, and Tablets 8A, 11A, 13A, and 15A, with and without orifice/hole, at 250 mg functional coating weight gain. The volume expansion studies were performed, using Rotating Bottle method at 5 rpm and 37° C., in 200 ml of pH 4.5 acetate buffer containing 10 mM of NaCl. The figure demonstrates that tablets without orifice/hole exhibit higher volume expansion compared to tablets with orifice/hole.

FIG. 12 compares volumetric expansion, at 90 minutes and at one hour, of Tablets 8, 11, 13, and 15, with and without orifice/hole, at 200 mg functional coating weight gain, and Tablets 8A, 11A, 13A, and 15A, with and without orifice/hole, at 250 mg functional coating weight gain. The volume expansion studies were performed, using Rotating Bottle method, at 5 rpm and 37° C., in 200 ml of pH 4.5 acetate buffer containing 10 mM of NaCl. The figure demonstrates that tablets without orifice/hole exhibit higher volume expansion compared to tablets with orifice/hole. The figure further demonstrates that the difference in volume expansion between tablets with and without a hole is more prominent in tablets with 200 mg coating weight gain (Tablets 8, 11, 13, 15) compared to tablets with 250 mg coating weight gain (Tablets 8A, 11A, 13A, 15A).

FIG. 13 compares volumetric expansion and weight gain at 24 hours, of Tablets 8, 11, 13, and 15, with orifice/hole and without orifice/hole, at 200 mg functional coating weight gain. The volume expansion and weight gain studies were performed, using Rotating Bottle method at 5 rpm and 37° C., in 200 ml of pH 4.5 acetate buffer containing 100 mM of NaCl. FIG. 13 demonstrates that tablets containing 200 mg of crospovidone (e.g., Tablets 11/11-H and 15/15-H) exhibit higher weight upon drying compared with tablets containing 100 mg of crospovidone (e.g., Tablets 8/8-H and 13/13-H).

Example 9

Dissolution Profiles of Gastroretentive Pyridostigmine Compositions Using BIO-DIS Method The present Example provides for measurements of dissolution profiles of various gastroretentive pyridostigmine compositions. Five compositions, as outlined in Table 13, were prepared, and tested using BIO-DIS method.

TABLE 13

Formulation of Pyridostigmine Bromide Tablets

| Ingredients | Tablet 8 (mg/dose) | Tablet 8B (mg/dose) | Tablet 15 (mg/dose) | Tablet 16 (mg/dose) | Tablet 17 (mg/dose) |
|---|---|---|---|---|---|
| Tablet Core | | | | | |
| Pyridostigmine bromide | 180.0 | 180.0 | 135.0 | 135.0 | 135.0 |
| Succinic acid | 50.0 | 50.0 | 125.0 | 125.0 | 85.0 |
| Sodium bicarbonate | 50.0 | 50.0 | 75.0 | 75.0 | 56.0 |
| Calcium carbonate | 125.0 | 125.0 | 100.0 | 100.0 | 67.0 |
| Crospovidone | 100.0 | 100.0 | 200.0 | 200.0 | 200.0 |
| PARTECK ® M200 | 233.0 | 233.0 | 153.0 | 153.0 | 45.0 |
| BENECEL ™ K4M PH DC | 200.0 | 200.0 | 100.0 | — | — |
| METHOCEL ™ K100 Prem LVCR | — | — | 100.0 | 200.0 | 400.0 |
| CAB-O-SIL ® | 4.00 | 4.00 | 4.00 | 4.00 | 4.00 |
| Magnesium stearate | 8.00 | 8.00 | 8.00 | 8.00 | 8.00 |
| Total Weight | 950.0 | 950.0 | 1000.0 | 1000.0 | 1000.0 |
| Seal Coat | | | | | |
| Hydroxypropyl cellulose | 33.33 | 33.33 | — | — | — |
| Talc | 3.33 | 3.33 | — | — | — |
| Triethyl citrate | 3.33 | 3.33 | — | — | — |
| Solvent* acetone:water (95:5) | q.s. | q.s. | — | — | — |
| Functional Coat | | | | | |
| EUDRAGIT ® RL PO | 148.15 | 296.3 | 148.15 | 148.15 | 148.15 |
| Triethyl citrate | 22.22 | 44.44 | 22.22 | 22.22 | 22.22 |
| Talc | 29.63 | 59.26 | 29.63 | 29.63 | 29.63 |
| Solvent* acetone:water (95:5) | q.s. | q.s. | q.s. | q.s. | q.s. |
| Over Coat | | | | | |
| OPADRY ® white | 15.0 | 15.0 | — | — | — |
| Solvent*Purified water, USP | q.s. | q.s. | — | — | — |
| Total Weight | 1205.0 | 1405.0 | 1200.0 | 1200.0 | 1200.0 |

*Removed during process

Tablets 8, 15, 16, and 17 contain 200 mg functional coating weight gain and Tablet 8B contains 400 mg functional coating weight gain. Tablets 8, 8B, 15, 16, and 17 were made according to the procedure as per Example 2 (and without the seal coat step for Tablets 15-17). FIG. 14 compares dissolution profiles of Tablets 8B, 15, 16, and 17 without an orifice/hole and Tablets 8, 8B, 15, 16, and 17 with an orifice/hole. Dissolution studies were performed using BIO-DIS method at 20 dpm and 37° C., in 250 ml of pH 3.0 dissolution medium containing 100 mM NaCl. FIG. 14 demonstrates that tablets without an orifice/hole exhibit slower drug release compared to tablets with an orifice/hole.

Example 10

Dissolution Profiles of Gastroretentive Pyridostigmine Compositions Using USP-I Method The present Example provides for measurements of dissolution profiles of various gastroretentive pyridostigmine compositions. Three compositions were prepared as outlined in Table 14 and tested using USP-I method.

TABLE 14

Formulation of Pyridostigmine Bromide Tablets

| Ingredients | Tablet 8 (mg/dose) | Tablet 18 (mg/dose) | Tablet 19 (mg/dose) |
|---|---|---|---|
| Tablet Core | | | |
| Pyridostigmine bromide | 180.0 | 180.0 | 180.0 |
| Succinic acid | 50.0 | 125.0 | 125.0 |
| Sodium bicarbonate | 50.0 | 75.0 | 75.0 |
| Calcium carbonate | 125.0 | 100.0 | 100.0 |
| Crospovidone | 100.0 | 200.0 | 200.0 |
| PARTECK ® M200 | 233.0 | 108.0 | 108.0 |
| BENECEL ® K4M PH DC | 200.0 | — | 100.0 |
| METHOCEL ® K100 Premium LVCR | — | 200.0 | 100.0 |

TABLE 14-continued

Formulation of Pyridostigmine Bromide Tablets

| Ingredients | Tablet 8 (mg/dose) | Tablet 18 (mg/dose) | Tablet 19 (mg/dose) |
|---|---|---|---|
| CAB-O-SIL ® | 4.00 | 4.00 | 4.00 |
| Magnesium stearate | 8.00 | 8.00 | 8.00 |
| Total Weight | 950.0 | 1000.0 | 1000.0 |
| *Seal Coat* | | | |
| Hydroxypropyl cellulose | 33.33 | — | — |
| Talc | 3.33 | — | — |
| Triethyl citrate | 3.33 | — | — |
| Solvent* acetone:water (95:5) | q.s. | q.s. | q.s. |
| *Functional Coat* | | | |
| EUDRAGIT ® RL PO | 148.15 | 107.15 | 107.15 |
| Triethyl citrate | 22.22 | 21.42 | 21.42 |
| Talc | 29.63 | 21.42 | 21.42 |
| Solvent* acetone:water (95:5) | q.s. | q.s. | q.s. |
| *Over Coat* | | | |
| OPADRY ® white | 15.0 | — | — |
| Solvent*Purified water, USP | q.s. | | |
| Total Weight | 1205.0 | 1150.0 | 1150.0 |

*Removed during process

Tablet 8 contains 200 mg of BENECEL® K4M PH DC and 100 mg of crospovidone, Tablet 18 contains 200 mg of METHOCEL™ and 200 mg of crospovidone, and Tablet 19 contains a mixture of 100 mg of METHOCEL™ K100 Premium LVCR, and 100 mg of BENECEL® K4M PH DC, and 200 mg of crospovidone. Tablets 8, 18, and 19 were made according to the procedure as per Example 2 (and without a seal coat step for Tablets 18 and 19). Tablets 8, 18, and 19 were tested for dissolution in about 900 ml of pH 5 acetate buffer, containing 150 mM of NaCl, 30 mM of sodium acetate, and 17 mM of acetic acid, using USP Apparatus I (Custom Basket), at 100 rpm and 37° C. FIG. 15 demonstrates that tablets containing 200 mg of crospovidone (Tablets 18 and 19) exhibit faster drug release and better drug recovery compared to Tablet 8 containing 100 mg of crospovidone.

Example 11

Dissolution Profiles of Gastroretentive Pyridostigmine Compositions Using USP-I Method The present Example provides for measurements of dissolution profiles of various gastroretentive pyridostigmine compositions. Three compositions, as outlined in Table 15, were prepared and tested using USP-I method.

TABLE 15

Formulation of Pyridostigmine Bromide Tablets

| Ingredients | Tablet 8 (mg/dose) | Tablet 20 (mg/dose) | Tablet 21 (mg/dose) |
|---|---|---|---|
| *Tablet Core* | | | |
| Pyridostigmine bromide | 180.0 | 305.0 | 255.0 |
| Succinic acid | 50.0 | 80.0 | 80.0 |
| Sodium bicarbonate | 50.0 | 55.0 | 55.0 |

TABLE 15-continued

Formulation of Pyridostigmine Bromide Tablets

| Ingredients | Tablet 8 (mg/dose) | Tablet 20 (mg/dose) | Tablet 21 (mg/dose) |
|---|---|---|---|
| Calcium carbonate | 125.0 | 65.0 | 65.0 |
| Crospovidone | 100.0 | 100.0 | 100.0 |
| PARTECK ® M200 | 233.0 | 73.0.0 | 123.0 |
| BENECEL ® K4M PH DC | 200.0 | 150.0 | 150.0 |
| METHOCEL ® K100 Prem LVCR | — | 150.0 | 150.0 |
| CAB-O-SIL ® | 4.00 | 10.00 | 10.00 |
| Magnesium stearate | 8.00 | 12.00 | 12.00 |
| Total Weight | 950.0 | 1000.0 | 1000.0 |
| *Seal Coat* | | | |
| Hydroxypropyl cellulose | 33.33 | — | — |
| Talc | 3.33 | — | — |
| Triethyl citrate | 3.33 | — | — |
| Solvent* acetone:water (95:5) | q.s. | q.s. | q.s. |
| *Functional Coat* | | | |
| EUDRAGIT ® RL PO | 148.15 | 148.15 | 148.15 |
| Triethyl citrate | 22.22 | 22.22 | 22.22 |
| Talc | 29.63 | 29.63 | 29.63 |
| Solvent* acetone:water (95:5) | q.s. | q.s. | q.s. |
| *Over Coat* | | | |
| OPADRY ® white | 15.0 | — | — |
| Solvent*Purified water, USP | q.s. | — | — |
| Total Weight | 1205.0 | 1200.0 | 1200.0 |

*Removed during process

Tablet 8 contains 200 mg of BENECEL™, Tablets 20 and 21 contain 150 mg each of BENECEL™ and METHOCEL™. Tablets 8, 20, and 21 were made according to the procedure as per Example 2 (and without a seal coat step for Tablets 20 and 21). Tablets 8, 20, and 21 were tested for dissolution in about 900 ml of pH 5.0 acetate buffer containing 150 mM NaCl, using USP Apparatus I (Custom Basket), at 100 rpm and 37° C. FIG. 16 demonstrates that tablets containing a mixture of 150 mg each of BENECEL™ and METHOCEL™ (Tablets 20 and 21) provide more controlled release compared to Tablet 8 containing 200 mg of BENECEL™.

Example 12

Dissolution Profiles of Gastroretentive Pyridostigmine Compositions Using USP-I Method The present Example provides for measurements of dissolution profiles of various gastroretentive pyridostigmine compositions. Three compositions were prepared as outlined in Table 15 and tested using USP-I method.

TABLE 16

Formulation of Pyridostigmine Bromide Tablets

| Ingredients | Tablet 8 (mg/dose) | Tablet 22 (mg/dose) | Tablet23 (mg/dose) |
|---|---|---|---|
| *Tablet Core* | | | |
| Pyridostigmine bromide | 180.0 | 135.0 | 135.0 |

TABLE 16-continued

Formulation of Pyridostigmine Bromide Tablets

| Ingredients | Tablet 8 (mg/dose) | Tablet 22 (mg/dose) | Tablet 23 (mg/dose) |
|---|---|---|---|
| Succinic acid | 50.0 | 80.0 | 80.0 |
| Sodium bicarbonate | 50.0 | 55.0 | 55.0 |
| Calcium carbonate | 125.0 | 65.0 | 65.0 |
| Crospovidone | 100.0 | 100.0 | 100.0 |
| PARTECK ® M200 | 233.0 | 249.0 | 299.0 |
| Oxide Pigment Black | — | — | 12.0 |
| BENECEL ® K4M PH DC | 200.0 | 150.0 | 150.0 |
| METHOCEL ® K100 Prem LVCR | — | 150.0 | 150.0 |
| CAB-O-SIL ® | 4.00 | 10.00 | 10.00 |
| Magnesium stearate | 8.00 | 12.00 | 12.00 |
| Total Weight | 950.0 | 1006.0 | 1068.0 |
| Seal Coat-1 | | | |
| Hydroxypropyl cellulose | 33.33 | — | — |
| Talc | 3.33 | — | — |
| Triethyl citrate | 3.33 | — | — |
| Solvent* acetone:water (95:5) | q.s. | — | — |
| Functional Coat | | | |
| EUDRAGIT ® RL PO | 148.15 | 148.15 | 148.15 |
| Triethyl citrate | 22.22 | 22.22 | 22.22 |
| Talc | 29.63 | 29.63 | 29.63 |
| Solvent* acetone:water (95:5) | q.s. | q.s. | q.s. |
| Seal Coat-2 | | | |
| OPADRY ® II, Clear | — | — | 10.0 |
| Solvent*Purified water, USP | — | — | q.s. |
| Drug Layer | | | |
| Pyridostigmine bromide | — | — | 45.0 |
| Hydroxypropyl cellulose | — | — | 9.0 |
| Solvent*Dehydrated alcohol, | — | — | q.s. |
| Over Coat | | | |
| OPADRY ® white | 15.0 | — | 40.0 |
| Solvent*Purified water, USP | q.s. | — | q.s. |
| Total Weight | 1205.0 | 1206.0 | 1372.0 |

*Removed during process

Tablet 23 contains an immediate release drug layer. Tablet 8 contains 200 mg of BENECEL® K4M PH DC, Tablets 22 and 23 contain 150 mg each of BENECEL® K4M PH DC and METHOCEL® K100 Prem LVCR. Tablets 8, 22, and 23 were made according to the procedure as per Example 2, with the following variations: Tablet 22 and Tablet 23 do not include a seal coat between the tablet core and the functional coat, and Tablet 23 was further coated with a seal coat (over the functional coat), an IR drug layer coat, and an over coat as follows:

D. Seal Coat
1. OPADRY® Clear was added to purified water in a stainless steel container and mixed to form a uniform dispersion.
2. Tablet core 23 with a functional coat was seal coated with the dispersion from Step 1, using a perforated pan coater with an inlet air temperature of 25° C.-60° C. at a product temperature of 30-45° C.

E. IR Drug Layer
1. Seal coated pyridostigmine bromide tablets from Step D were further coated with a solution of pyridostigmine bromide, hydroxypropyl cellulose in dehydrated alcohol, using a perforated pan coater with an inlet air temperature of 25° C.-60° C. at a product temperature of 30-45° C.

F. Over Coat
1. Weighed quantity of OPADRY® white was added to a required amount of purified water and mixed to obtain a uniform dispersion.
2. The tablets with IR drug layer from Step E were further coated with the dispersion from step #1 in a perforated coating pan with inlet air temperature at 25° C.-45° C.
3. The coated tablets from step #2 were dried in the coating pan to a moisture content of below 1.5%.

Tablets 8, 22, and 23 were tested for dissolution in about 900 ml of pH 5.0 acetate buffer containing 150 mM of NaCl, using USP Apparatus I (Custom Basket), at 100 rpm and 37° C. FIG. 17 demonstrates that the tablet containing an immediate release drug layer (Tablet 23) eliminates lag time compared to tablets that do not contain an immediate release drug layer (Tablets 8 and 22).

Example 13

Additional Gastroretentive Pyridostigmine Compositions

The present Example provides for various gastroretentive pyridostigmine compositions. Ten different compositions were prepared as outlined in Tables 17 and 18.

TABLE 17

Formulation of Pyridostigmine Bromide Tablets

| Ingredients | Tablet 24 (mg/dose) | Tablet 25 (mg/dose) | Tablet 26 (mg/dose) | Tablet 27 (mg/dose) | Tablet 28 (mg/dose) |
|---|---|---|---|---|---|
| Tablet Core | | | | | |
| Pyridostigmine bromide | 305.0 | 305.0 | 305.0 | 255.0 | 255.0 |
| Succinic acid | 80.0 | 80.0 | 80.0 | 80.0 | 80.0 |
| Sodium bicarbonate | 55.0 | 55.0 | 55.0 | 55.0 | 55.0 |
| Calcium carbonate | 65.0 | 65.0 | 65.0 | 65.0 | 65.0 |
| Crospovidone | 100.0 | 100.0 | 100.0 | 100.0 | 100.0 |
| PARTECK ® M200 | 73.0 | — | — | 123.0 | — |

TABLE 17-continued

Formulation of Pyridostigmine Bromide Tablets

| Ingredients | Tablet 24 (mg/dose) | Tablet 25 (mg/dose) | Tablet 26 (mg/dose) | Tablet 27 (mg/dose) | Tablet 28 (mg/dose) |
|---|---|---|---|---|---|
| BENECEL ® K4M PH DC | 150.0 | 186.5.0 | 236.5 | 150.0 | 211.5 |
| METHOCEL ® K100 Prem LVCR | 150.0 | 186.5 | 236.5 | 150.0 | 211.5 |
| CAB-O-SIL ® | 10.00 | 10.00 | 10.00 | 10.00 | 10.00 |
| Magnesium stearate | 12.00 | 12.00 | 12.00 | 12.00 | 12.00 |
| Total Weight | 1000.0 | 1000.0 | 1100.0 | 1000.0 | 1000.0 |
| Functional Coat | | | | | |
| EUDRAGIT ® RL PO | 148.15 | 148.15 | 148.15 | 148.15 | 148.15 |
| Triethyl citrate | 22.22 | 22.22 | 22.22 | 22.22 | 22.22 |
| Talc | 29.63 | 29.63 | 29.63 | 29.63 | 29.63 |
| Solvent* acetone:water (95:5) | q.s. | q.s. | q.s. | q.s. | q.s. |
| Total Weight | 1200.0 | 1200.0 | 1300.0 | 1200.0 | 1200.0 |

TABLE 18

Formulation of Pyridostigmine Bromide Tablets

| Ingredients | Tablet 29 (mg/dose) | Tablet 30 (mg/dose) | Tablet 31 (mg/dose) | Tablet 32 (mg/dose) | Tablet 33 (mg/dose) |
|---|---|---|---|---|---|
| Tablet Core | | | | | |
| Pyridostigmine bromide | 70.0 | 155.0 | 205.0 | 305.0 | 100.0 |
| Succinic acid | 80.0 | 80.0 | 80.0 | 80.0 | 80.0 |
| Sodium bicarbonate | 55.0 | 55.0 | 55.0 | 55.0 | 55.0 |
| Calcium carbonate | 65.0 | 65.0 | 65.0 | 65.0 | 65.0 |
| Crospovidone | 100.0 | 100.0 | 100.0 | 100.0 | 100.0 |
| PARTECK ® M200 | 308.0 | 223.0 | 173.0 | — | 278.0 |
| BENECEL ® K4M PH DC | 150.0 | 150.0 | 150.0 | 150.0 | 150.0 |
| METHOCEL ® K100 Prem LVCR | 150.0 | 150.5 | 150.0 | 223.0 | 150.0 |
| CAB-O-SIL ® | 10.00 | 10.00 | 10.00 | 10.00 | 10.0 |
| Magnesium stearate | 12.00 | 12.00 | 12.00 | 12.00 | 12.0 |
| Total Weight | 1000.0 | 1000.5 | 1000.0 | 1000.0 | 1000.0 |
| Functional Coat | | | | | |
| EUDRAGIT ® REPO | 148.15 | 148.15 | 148.15 | 148.15 | 148.15 |
| Triethyl citrate | 22.22 | 22.22 | 22.22 | 22.22 | 22.22 |
| Talc | 29.63 | 29.63 | 29.63 | 29.63 | 29.63 |
| Solvent* acetone:water (95:5) | q.s. | q.s. | q.s. | q.s. | q.s. |
| Total Weight | 1200.0 | 1200.5 | 1200.0 | 1200.0 | 1200.0 |

*Removed during process

Tablets 24-26, and 32 contain 305 mg of pyridostigmine bromide; Tablets 27 and 28 contain 255 mg of pyridostigmine bromide, Tablet 29 contains 70 mg of pyridostigmine bromide, Tablet 30 contains 155 mg of pyridostigmine bromide, Tablet 31 contains 205 mg of pyridostigmine bromide, and Tablet 33 contains 100 mg of pyridostigmine bromide. Tablets 24, 27, 29-31, and Tablet 33 contain 150 mg each of BENECEL® K4M PH DC and METHOCEL® K100 Premium LVCR, Tablet 25 contains 186.5 mg each of BENECEL® K4M PH DC and METHOCEL® K100 Premium LVCR, Tablet 26 contains 236.5 mg each of BENECEL® K4M PH DC and METHOCEL® K100 Premium LVCR, Tablet 28 contains 211.5 mg each of BENECEL® K4M PH DC and METHOCEL® K100 Premium LVCR, and Tablet 32 contains 150.0 mg of BENECEL® K4M PH DC and 223.0 mg of METHOCEL® K100 Premium LVCR. Tablets 24-32 were made according to the procedure as per Example 2. Tablet 33 is made according to the procedure as per Example 2.

Example 14

Gastroretentive Pyridostigmine Compositions with IR Drug Layer

The present Example provides for gastroretentive pyridostigmine compositions that comprise an immediate release drug layer. Four different compositions were prepared as outlined in Table 19.

Tablets 34 and 35 contain an immediate release drug layer containing 45 mg of pyridostigmine bromide and an extended release component/tablet core containing 135 mg of pyridostigmine bromide. Tablet 36 contains an immediate release drug layer containing 30 mg of pyridostigmine bromide and an extended release component/tablet core containing 70 mg of pyridostigmine bromide. Tablet 37 contains an immediate release drug layer containing 20 mg of pyridostigmine bromide and an extended release component/tablet core containing 160 mg of pyridostigmine bromide. Tablets 34-37 contain 150 mg each of BENECEL® K4M PH DC and METHOCEL® K100 Prem LVCR. Tablets 34, 36, and 37 contain a laser drilled hole in the functional coat and Tablet 35 is without a hole. Tablets 34, 35, and 37 were made as per Tablet 23 in Example 12. Tablet 36 is made as per Tablet 23 in Example 12.

TABLE 19

Formulation of Pyridostigmine Bromide Tablets

| Ingredients | Tablet 34 (with hole) | Tablet 35 | Tablet 36 | Tablet 37 |
|---|---|---|---|---|
| Tablet Core | | | | |
| Pyridostigmine bromide | 135.0 | 135.0 | 70.00 | 160.0 |
| Succinic acid | 80.0 | 80.0 | 80.0 | 80.0 |
| Sodium bicarbonate | 55.0 | 55.0 | 55.0 | 55.0 |
| Calcium carbonate | 65.0 | 65.0 | 65.0 | 65.0 |
| Crospovidone | 100.0 | 100.0 | 100.0 | 100.0 |
| PARTECK ® M200 | 235.5 | 231.0 | 278.0 | 218.0 |
| Oxide Pigment Black | 7.5 | 12.0 | 12.0 | 0 |
| BENECEL ® K4M PH DC | 150.0 | 150.0 | 150.0 | 150.0 |
| METHOCEL ® K100 Prem LVCR | 150.0 | 150.0 | 150.0 | 150.0 |
| CAB-O-SIL ® | 10.00 | 10.00 | 10.0 | 10.0 |
| Magnesium stearate | 12.00 | 12.00 | 12.0 | 12.0 |
| Total Weight | 1000.0 | 1000.0 | 982.0 | 1000.0 |
| Functional Coat | | | | |
| EUDRAGIT ® RL PO | 148.15 | 148.15 | 148.15 | 148.15 |
| Triethyl citrate | 22.22 | 22.22 | 22.22 | 22.22 |
| Talc | 29.63 | 29.63 | 29.63 | 29.63 |
| Solvent* acetone:water (95:5) | q.s. | q.s. | q.s. | q.s. |
| Seal Coat | | | | |
| OPADRY ® II, Clear | 10.0 | 10.0 | 10.0 | 10.0 |
| Solvent*Purified water, USP | q.s. | q.s. | q.s. | q.s. |
| Drug Layer | | | | |
| Pyridostigmine bromide | 45.0 | 45.0 | 30.0 | 20.0 |
| Hydroxypropyl cellulose | 9.0 | 9.0 | 9.0 | 4.0 |
| Solvent*Dehydrated alcohol, USP | q.s. | q.s. | q.s. | q.s. |
| Over Coat | | | | |
| OPADRY ® White | 40.0 | 40.0 | 40.0 | 40.0 |
| Solvent*Purified water, USP | q.s. | q.s. | q.s. | |
| Total Weight | 1304.0 | 1304.0 | 1271.0 | 1274.0 |

*Removed during process

Example 15

Oral Bioavailability of Pyridostigmine for Tablet 34 (Gastroretentive Dosage Form with Hole)

A single dose pharmacokinetic (PK) study was conducted in healthy volunteers under fed conditions to evaluate the PK performance of extended release compositions of the disclosure using Tablet 34. An open-label, balanced, non-randomized, single-dose, two-treatment, one-way crossover, comparative bioavailability study was conducted in 15 normal, healthy, adult, human subjects under high-fat high-calorie breakfast conditions and under low fat-low calorie conditions.

Pharmacokinetic parameters for pyridostigmine are summarized in Table 20.

TABLE 20

Pharmacokinetics Results of Pyridostigmine

| Pharmacokinetic parameters (units) | LF-LC (Condition I) Mean ± SD (CV %) (N = 15) | HF-HC (Condition II) Mean ± SD (CV %) (N = 15) |
|---|---|---|
| $C_{max}$ (ng/mL) | 42.178 ± 9.890 (23.448) | 45.073 ± 6.094 (13.520) |
| $AUC_{0-t}$ (ng · hr/mL) | 670.921 ± 287.971 (42.922) | 735.1391 ± 173.317 (23.576) |
| AUC0-inf (ng · hr/mL) | 684.726 ± 292.086 (42.657) | 749.674 ± 174.634 (23.295) |
| $T_{max}$ (hr)* | 7.10 ± 3.80 (53.55) | 11.0 ± 2.77 (25.19) |
| $K_{el}$ (hr−1) | 0.15 ± 0.03 (18.90) | 0.15 ± 0.03 (22.02) |
| $t_{1/2}$ (hr) | 4.77 ± 1.03 (21.65) | 4.70 ± 1.06 (22.52) |
| AUC Extrapolated (%) | 2.209 ± 1.383 (62.610) | 2.084 ± 1.657 (79.549) |

The data from this study (Table 20/FIG. 20) demonstrates that Tablet 34 provides a therapeutic plasma concentration of pyridostigmine for at least about 22 hours.

Example 16

Oral Bioavailability of Pyridostigmine for Tablet 35 (Gastroretentive Dosage Form without Hole)

A single dose pharmacokinetic (PK) study was conducted in healthy volunteers under fed conditions to evaluate the PK performance of extended release compositions of the disclosure using Tablet 35. An open-label, balanced, non-randomized, single-dose, two-treatment, one-way crossover, comparative bioavailability study was conducted in 15 normal, healthy, adult, human subjects under high-fat high-calorie breakfast conditions and under low fat-low calorie conditions.

Pharmacokinetic parameters for pyridostigmine are summarized in Table 21.

TABLE 21

Pharmacokinetics Results of Pyridostigmine

| Pharmacokinetic parameters (units) | LF-LC (Condition I) Mean ± SD (CV %) (N = 15) | HF-HC (Condition II) Mean ± SD (CV %) (N = 15) |
|---|---|---|
| $C_{max}$ (ng/mL) | 47.444 ± 12.070 (25.440) | 43.204 ± 13.455 (31.144) |
| $AUC_{0-t}$ (ng · hr/mL) | 628.282 ± 322.601 (51.346) | 761.807 ± 297.513 (39.054) |
| AUC0-inf (ng · hr/mL) | 635.600 ± 336.928 (53.009) | 643.820 ± 161.166 (25.033) |
| $T_{max}$ (hr)* | 8.10 ± 6.25 (77.14) | 15.44 ± 4.92 (31.85) |
| $K_{el}$ (hr−1) | 0.14 ± 0.04 (27.80) | 0.15 ± 0.05 (31.12) |
| $t_{1/2}$ (hr) | 5.23 ± 1.61 (30.77) | 5.20 ± 2.03 (39.15) |
| AUC Extrapolated (%) | 2.654 ± 2.429 (91.528) | 3.621 ± 4.396 (121.392) |

The data from this study (Table 21/FIG. 21) demonstrate that Tablet 35 provides a therapeutic plasma concentration of pyridostigmine for at least about 22 hours.

Example 17

Volume Expansion and Texture Analysis/Compressibility for Tablet 34 (Gastroretentive Dosage Form with Hole)

Tablet 34 was tested for volume expansion and texture analysis/compressibility. The volume expansion studies were performed using Rotating Bottle method, at 5 rpm and 37° C., in 200 ml of 0.001 N HCL containing 10 mM NaCl. FIG. 25A demonstrates that Tablet 34 exhibits 100% volume gain at about 30 minutes, 200% volume gain at about 1 hour, and 300% volume gain at 8 about hours post-administration of the tablet into the dissolution medium. Tablet 34 was simultaneously tested for its texture/compressibility at various time points using TA.XT$^{Plus}$ apparatus. FIG. 25B demonstrates that the compression force required to squeeze out the matrix core at 2 hours post-administration, at about 200% volume gain, was 30 N; at 8 hours post-administration, at about 300% volume gain, was 18.3 N; and at 24 hours post-administration, at about 250% volume gain, was 4.1 N. It was observed that the tablet maintained its GRS attributes of floatation and expansion for at least about 14 hours, e.g., about 24 hours. The experiment demonstrates that Tablet 34, in its expanded state, e.g., between about 250% and about 300% volume gain, can withstand forces of about 10 N until 14 hours, and the matrix core can be subsequently squeezed thereafter even with force less than 5 N, after at least about 20 hours, e.g., about 24 hours, post-administration.

What is claimed is:

1. A gastroretentive dosage form comprising an immediate release layer and an extended release component;
wherein the immediate release layer comprises between about 10 mg and about 60 mg pyridostigmine bromide; and the extended release component comprises a core and a permeable elastic membrane surrounding the core,
wherein the core comprises between about 50 mg and about 400 mg pyridostigmine bromide, hypromellose in an amount of between about 5 wt % and about 35 wt %, based on the total weight of the core, succinic acid, a carbonate salt, and a bicarbonate salt, wherein the permeable elastic membrane comprises a plasticizer in an amount of between about 5 wt % and about 25 wt % of the membrane, and a copolymer based on ethyl acrylate, methyl methacrylate, and trimethylammonioethyl methacrylate chloride in powder form (1:2:0.2), in an amount of between about 75 wt % and about 95 wt % of the membrane, and wherein the dosage form provides an extended release of pyridostigmine bromide for at least about 14 hours.

2. The dosage form of claim 1, wherein the dosage form provides an in vitro release of between about 20% and about 35% of the pyridostigmine bromide within about 2 hours of dissolution in a dissolution medium comprising pH 4.5 acetate buffer with 100 mM NaCl.

3. The dosage form of claim 1, wherein the dosage form floats in about 40 minutes or less in a dissolution medium comprising pH 4.5 acetate buffer with 100 mM NaCl.

4. The dosage form of claim 1, wherein the dosage form, when in contact with gastric fluid, swells in about 60 minutes or less to a size that prevents its passage through pyloric sphincter.

5. The dosage form of claim 4, wherein the dosage form maintains its integrity in a swollen state for a period of at least about 14 hours.

6. The dosage form of claim 1, wherein the core further includes crospovidone as a wicking agent.

7. The dosage form of claim 1, wherein the carbonate and bicarbonate salts comprise $CaCO_3$ and $NaHCO_3$, respectively.

8. The dosage form of claim 1, wherein the plasticizer is triethyl citrate.

9. The dosage form of claim 1, wherein the dosage form further includes a seal coat between the permeable elastic membrane and the immediate release layer.

10. The dosage form of claim 9, wherein the dosage form does not include a seal coat between the core and the permeable elastic membrane.

11. The dosage form of claim 9, wherein the dosage form further includes an orifice passing through the permeable elastic membrane and the seal coat.

12. The dosage form of claim 1, wherein the dosage form is a tablet.

13. The dosage form of claim 12, wherein the dosage form is suitable for once daily administration and is administered as a single tablet/day.

14. The dosage form of claim 1, wherein the hypromellose is a mixture of a low viscosity hypromellose and a high viscosity hypromellose.

15. The dosage form of claim 14, wherein the low viscosity hypromellose has a viscosity of between about 80 mPa·s and about 120 mPa·s.

16. The dosage form of claim 14, wherein the high viscosity hypromellose has a viscosity of between about, 2,700 mPa·s and about 5,040 mPa·s.

17. The dosage form of claim 1, wherein the hypromellose is a high viscosity hypromellose having a viscosity of between about 2,700 mPa·s and about 5,040 mPa·s.

18. A gastroretentive dosage form comprising an immediate release layer and an extended release component;

wherein the immediate release layer comprises between about 10 mg and about 60 mg pyridostigmine bromide; and the extended release component comprises a core and a permeable elastic membrane surrounding the core, wherein the core comprises between about 50 mg and about 400 mg pyridostigmine bromide, a high viscosity hypromellose in an amount of between about 5 wt % and about 35 wt %, based on the total weight of the core, succinic acid, a carbonate salt, and a bicarbonate salt, wherein the high viscosity hypromellose has a viscosity of between about, 2,700 mPa·s and about 5,040 mPa·s, wherein each of sodium bicarbonate and calcium carbonate is present in equimolar amounts with respect to succinic acid, wherein each of sodium bicarbonate, calcium carbonate, and succinic acid is present in an amount of between about 1 wt % and about 10 wt %, based on the total weight of the core, wherein the permeable elastic membrane comprises a plasticizer in an amount of between about 5 wt % and about 25 wt % of the membrane composition, and a copolymer based on ethyl acrylate, methyl methacrylate, and trimethylammonioethyl methacrylate chloride in powder form (1:2:0.2), in an amount of between about 75 wt % and about 95 wt % of the membrane composition, and wherein the dosage form floats in about 40 minutes or less in pH 4.5 acetate buffer with 100 mM NaCl.

19. A gastroretentive dosage form comprising a core and a permeable elastic membrane surrounding the core, wherein the core comprises between about 50 mg and about 400 mg pyridostigmine bromide, hypromellose in an amount of between about 5 wt % and about 35 wt %, based on the total weight of the core, succinic acid, a carbonate salt, and a bicarbonate salt, wherein the hypromellose has a viscosity of between about, 2,700 mPa·s and about 5,040 mPa·s, wherein each of sodium bicarbonate and calcium carbonate is present in equimolar amounts with respect to succinic acid, wherein each of sodium bicarbonate, calcium carbonate, and succinic acid is present in an amount of between about 1 wt % and about 10 wt %, based on the total weight of the core, wherein the permeable elastic membrane comprises a plasticizer in an amount of between about 5 wt % and about 25 wt % of the membrane composition, and a copolymer based on ethyl acrylate, methyl methacrylate, and trimethylammonioethyl methacrylate chloride in powder form (1:2:0.2), in an amount of between about 75 wt % and about 95 wt % of the membrane composition, wherein the dosage form floats in about 40 minutes or less in pH 4.5 acetate buffer with 100 mM NaCl, and wherein the dosage form provides an extended release of pyridostigmine bromide for at least about 14 hours.

* * * * *